(12) United States Patent
Huang et al.

(10) Patent No.: US 11,560,574 B2
(45) Date of Patent: *Jan. 24, 2023

(54) METHODS AND COMPOSITIONS FOR SELECTIVE REGULATION OF PROTEIN EXPRESSION

(71) Applicant: Monsanto Technology LLC, St. Louis, MO (US)

(72) Inventors: Jintai Huang, Chesterfield, MO (US); Sergey Ivashuta, Ballwin, MO (US); Youlin Qi, Chesterfield, MO (US); Barbara Elizabeth Wiggins, Chesterfield, MO (US); Yuanji Zhang, Weldon Spring, MO (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 10 days.

This patent is subject to a terminal disclaimer.

(21) Appl. No.: 16/845,907

(22) Filed: Apr. 10, 2020

(65) Prior Publication Data

US 2020/0340010 A1    Oct. 29, 2020

Related U.S. Application Data

(60) Continuation of application No. 15/726,363, filed on Oct. 5, 2017, now Pat. No. 10,689,667, which is a division of application No. 14/720,052, filed on May 22, 2015, now Pat. No. 9,816,106, which is a continuation of application No. 13/538,670, filed on Jun. 29, 2012, now Pat. No. 9,139,838.

(60) Provisional application No. 61/504,102, filed on Jul. 1, 2011.

(51) Int. Cl.
    *C12N 15/82* (2006.01)

(52) U.S. Cl.
    CPC ..... *C12N 15/8289* (2013.01); *C12N 15/8218* (2013.01); *C12N 15/8275* (2013.01)

(58) Field of Classification Search
    None
    See application file for complete search history.

(56) References Cited

U.S. PATENT DOCUMENTS

| | | | |
|---|---|---|---|
| 676,234 A | 6/1901 | Humpaga et al. |
| 4,535,060 A | 8/1985 | Comai |
| 4,735,649 A | 4/1988 | Dhingra et al. |
| 4,761,373 A | 8/1988 | Anderson et al. |
| 4,769,061 A | 9/1988 | Comai |
| 4,940,835 A | 7/1990 | Shah et al. |
| 4,971,908 A | 11/1990 | Kishore et al. |
| 5,034,322 A | 7/1991 | Rogers et al. |
| 5,068,193 A | 11/1991 | Comai |
| 5,094,945 A | 3/1992 | Comai |
| 5,188,642 A | 2/1993 | Shah et al. |
| 5,356,799 A | 10/1994 | Fabijanski et al. |
| 5,436,389 A | 7/1995 | Pfund |
| 5,484,956 A | 1/1996 | Lundquist et al. |
| 5,489,520 A | 2/1996 | Adams et al. |
| 5,554,798 A | 9/1996 | Lundquist et al. |
| 5,583,210 A | 12/1996 | Neill et al. |
| 5,627,061 A | 5/1997 | Barry et al. |
| 5,633,435 A | 5/1997 | Barry et al. |
| 5,641,664 A | 6/1997 | D'Halluin et al. |
| 5,641,876 A | 6/1997 | McElroy et al. |
| 5,668,297 A | 9/1997 | Broer et al. |
| 6,040,497 A | 3/2000 | Spencer et al. |
| 6,046,382 A | 4/2000 | Mariam et al. |
| 6,057,496 A | 5/2000 | Conner |
| 6,072,102 A | 6/2000 | Cigan et al. |
| 6,072,110 A | 6/2000 | Henson |
| 6,255,564 B1 | 7/2001 | Fabijanski et al. |
| 6,384,304 B1 | 5/2002 | Quandt et al. |
| 6,448,476 B1 | 9/2002 | Barry |
| 6,476,291 B1 | 11/2002 | Conner |
| 6,646,186 B1 | 11/2003 | Stine et al. |
| 6,750,377 B1 | 6/2004 | Kaster, Jr. et al. |
| 6,825,400 B2 | 11/2004 | Behr et al. |
| 7,230,168 B2 | 6/2007 | Huang et al. |
| 7,306,909 B2 | 12/2007 | Krieb et al. |
| 7,314,970 B2 | 1/2008 | Spencer et al. |
| 7,355,096 B2 | 4/2008 | Spangenberg et al. |
| 7,491,813 B2 | 2/2009 | Wu et al. |
| 7,554,012 B2 | 6/2009 | Barry |
| 7,615,678 B2 | 11/2009 | Flasinski |
| 7,750,207 B2 | 7/2010 | Wu et al. |

(Continued)

FOREIGN PATENT DOCUMENTS

| CL | 1891-1995 | 7/1996 |
|---|---|---|
| CL | 1704-2000 | 6/2001 |

(Continued)

OTHER PUBLICATIONS

Grant-Downtown et al, 2012, Biomolecules, 2:608-621.*
Omidvar et al, 2015, BMC Genomics, 1-16.*
Li et al, 2017, BMC Genomics, 18:1-18.*
Chuck et al, 2007, Nature Genetics, 39:544-549.*
Alexandrov et al, 2009, Plant Mol Biol, 69:179-194.*
Yang, et al. 2018 Endogenous tassel-specific small RNAs-mediated RNA interference enables a novel glyphosate inducible male sterility system for commercial production of hybrid seed in *Zea mays* PLOS One 13(8):e0202921.

(Continued)

*Primary Examiner* — Jason Deveau Rosen
(74) *Attorney, Agent, or Firm* — Dentons US LLP; Elizabeth Millard, Esq.

(57) ABSTRACT

The invention provides methods and compositions for selectively suppressing the expression of a recombinant protein in a male reproductive tissue of a transgenic plant. The invention also provides methods and compositions for inducing male sterility in a transgenic plant. Plants, plant cells, plant parts, seeds, and commodity products including such compositions are aspects of the invention.

27 Claims, 14 Drawing Sheets

Specification includes a Sequence Listing.

(56) References Cited

U.S. PATENT DOCUMENTS

| | | |
|---|---|---|
| 7,919,321 B2 | 4/2011 | Flasinski |
| 7,939,709 B2 | 5/2011 | Hawkes et al. |
| 8,158,850 B2 | 4/2012 | Feng et al. |
| 8,212,113 B2 | 7/2012 | Beazley et al. |
| 8,217,227 B2 | 7/2012 | Allen et al. |
| 8,334,430 B2 | 12/2012 | Allen et al. |
| 8,344,211 B2 | 1/2013 | Alexandrov et al. |
| 8,466,270 B2 | 6/2013 | Flasinski |
| 8,618,358 B2 | 12/2013 | Feng et al. |
| 9,139,838 B2* | 9/2015 | Huang .................. A01N 65/44 |
| 9,816,106 B2* | 11/2017 | Huang .............. C12N 15/8289 |
| 10,561,083 B2 | 2/2020 | Feng et al. |
| 10,689,667 B2* | 6/2020 | Huang .................. A01N 65/44 |
| 10,704,057 B2 | 7/2020 | Huang et al. |
| 10,920,239 B2 | 2/2021 | Ellis et al. |
| 11,441,155 B2 | 9/2022 | Feng et al. |
| 2001/0023501 A1 | 9/2001 | Johal et al. |
| 2002/0062499 A1 | 5/2002 | Conner et al. |
| 2003/0106096 A1 | 6/2003 | Barry |
| 2004/0034888 A1 | 2/2004 | Liu et al. |
| 2005/0150013 A1 | 7/2005 | Hawkes et al. |
| 2006/0059581 A1 | 3/2006 | Spencer et al. |
| 2006/0200878 A1 | 9/2006 | Lutfiyya et al. |
| 2007/0011775 A1 | 1/2007 | Allen et al. |
| 2007/0083947 A1 | 4/2007 | Huang et al. |
| 2007/0083949 A1 | 4/2007 | Huang et al. |
| 2007/0083950 A1 | 4/2007 | Huang et al. |
| 2007/0083951 A1 | 4/2007 | Huang et al. |
| 2007/0083952 A1 | 4/2007 | Huang et al. |
| 2007/0089184 A1 | 4/2007 | Huang et al. |
| 2007/0089185 A1 | 4/2007 | Juang et al. |
| 2007/0089186 A1 | 4/2007 | Huang et al. |
| 2007/0089187 A1 | 4/2007 | Huang et al. |
| 2007/0089188 A1 | 4/2007 | Huang et al. |
| 2007/0089189 A1 | 4/2007 | Huang et al. |
| 2007/0089190 A1 | 4/2007 | Huang et al. |
| 2007/0089191 A1 | 4/2007 | Huang et al. |
| 2007/0089192 A1 | 4/2007 | Huang et al. |
| 2007/0089193 A1 | 4/2007 | Huang et al. |
| 2007/0089194 A1 | 4/2007 | Huang et al. |
| 2007/0089195 A1 | 4/2007 | Huang et al. |
| 2007/0089196 A1 | 4/2007 | Huang et al. |
| 2007/0094748 A1 | 4/2007 | Huang et al. |
| 2007/0113301 A1 | 5/2007 | Huang et al. |
| 2007/0113302 A1 | 5/2007 | Huang et al. |
| 2007/0118917 A1 | 5/2007 | Huang et al. |
| 2007/0118918 A1 | 5/2007 | Huang et al. |
| 2007/0130645 A1 | 6/2007 | Wu et al. |
| 2007/0199095 A1* | 8/2007 | Allen ................. C12N 15/8289 800/278 |
| 2007/0209085 A1 | 9/2007 | Wu et al. |
| 2007/0300329 A1 | 12/2007 | Allen et al. |
| 2008/0229456 A1 | 9/2008 | Huang et al. |
| 2009/0013434 A1 | 1/2009 | Huang et al. |
| 2009/0165166 A1 | 6/2009 | Feng et al. |
| 2009/0293148 A1 | 11/2009 | Ren et al. |
| 2010/0223694 A1 | 9/2010 | Lutfiyya et al. |
| 2011/0035838 A1 | 2/2011 | Lutfiyya et al. |
| 2011/0126310 A1 | 5/2011 | Feng et al. |
| 2011/0150832 A1 | 6/2011 | Nemunaitis et al. |
| 2011/0167513 A1 | 7/2011 | Gils et al. |
| 2011/0271399 A1 | 11/2011 | Cerny et al. |
| 2012/0317680 A1 | 12/2012 | Feng et al. |
| 2013/0007908 A1 | 1/2013 | Huang et al. |
| 2013/0074213 A1 | 3/2013 | Allen et al. |
| 2013/0291138 A1 | 10/2013 | Feng et al. |
| 2014/0007288 A1 | 1/2014 | Flasinski |
| 2014/0109250 A1 | 4/2014 | Feng et al. |
| 2017/0029841 A1 | 2/2017 | Huang et al. |
| 2020/0205361 A1 | 7/2020 | Feng et al. |
| 2020/0283790 A1 | 9/2020 | Huang et al. |

FOREIGN PATENT DOCUMENTS

| | | |
|---|---|---|
| CL | 1652-06 | 2/2007 |
| DE | 4126414 A1 | 2/1993 |
| EA | 6761 B1 | 4/2006 |
| EP | 0218571 A2 | 4/1987 |
| EP | 0242236 A1 | 10/1987 |
| EP | 0242246 A1 | 10/1987 |
| EP | 0242246 B1 | 10/1987 |
| EP | 0290395 A2 | 11/1988 |
| EP | 0329308 A2 | 8/1989 |
| EP | 0348348 A2 | 12/1989 |
| EP | 0353908 A2 | 2/1990 |
| EP | 0360750 A2 | 3/1990 |
| EP | 0242236 B1 | 10/1990 |
| EP | 0426641 A2 | 5/1991 |
| EP | 0469273 A1 | 2/1992 |
| EP | 0218571 | 2/1993 |
| EP | 0290395 B1 | 1/1994 |
| EP | 0353908 B1 | 5/1995 |
| EP | 0348348 B1 | 8/2000 |
| EP | 0426641 B1 | 9/2000 |
| EP | 0329308 B1 | 10/2001 |
| EP | 0469273 B1 | 12/2003 |
| EP | 0975778 B1 | 6/2007 |
| FR | 2661421 A1 | 10/1991 |
| RU | 2380411 C2 | 1/2010 |
| WO | WO 87/05629 A1 | 9/1987 |
| WO | WO 90/08828 A2 | 8/1990 |
| WO | WO 91/02071 A2 | 2/1991 |
| WO | WO 91/09948 A1 | 7/1991 |
| WO | WO 91/10725 A1 | 7/1991 |
| WO | WO 92/04449 A1 | 3/1992 |
| WO | WO 95/06128 A2 | 3/1995 |
| WO | WO 97/04103 A2 | 2/1997 |
| WO | WO 97/04114 A2 | 2/1997 |
| WO | WO 97/06269 A1 | 2/1997 |
| WO | WO 1997/006269 | 2/1997 |
| WO | WO 97/23634 A2 | 7/1997 |
| WO | WO 97/46690 A1 | 12/1997 |
| WO | WO 99/46396 A2 | 9/1999 |
| WO | WO 99/46396 A3 | 10/1999 |
| WO | WO 01/44457 A2 | 6/2001 |
| WO | WO 2001/073087 | 10/2001 |
| WO | WO 02/06995 A1 | 4/2002 |
| WO | WO 02/078427 A2 | 10/2002 |
| WO | WO 02078427 | 10/2002 |
| WO | WO 2004/009779 A2 | 1/2004 |
| WO | WO 2005/035769 A2 | 4/2005 |
| WO | WO 2006/014678 | 2/2006 |
| WO | WO 2006/073727 A2 | 7/2006 |
| WO | WO 2006/074400 A2 | 7/2006 |
| WO | WO 2006/111512 A1 | 10/2006 |
| WO | WO 2007/047016 | 4/2007 |
| WO | WO 2007/047016 A2 | 4/2007 |
| WO | WO 2007/047016 A3 | 2/2008 |
| WO | WO 2009/085982 A1 | 7/2009 |
| WO | WO 2010/099084 A2 | 9/2010 |
| WO | WO 2010/117735 A1 | 10/2010 |
| WO | WO 2010/117737 A8 | 6/2011 |

OTHER PUBLICATIONS

U.S. Appl. No. 16/737,870, filed Jan. 8, 2020, Feng et al.
Axtell et al., "Antiquity of MicroRNAs and Their Targets in Land Plants," *The Plant Cell*, 17:1658-1673 (2005).
Achard et al., "Modulation of floral development by a gibberellin-regulated microRNA," *Development*, 131:3357-3365 (2004).
Advisory Action dated Mar. 27, 2015, in U.S. Appl. No. 13/677,607 (3 pgs.).
Allen et al., "Evolution of microRNA genes by inverted duplication of target gene sequences in *Arabidopsis thaliana*," *Nature Genetics*, 36(12):1282-1290 (2004).
Amrhein, et al., "Biochemical basis for glyphosate-tolerance in a bacterium and a plant tissue culture," *FEBS*,157(1):191-196 (1983).
Anderson, "Spread of Perennial Weeds," Weed Science, 13-15 (1983).
Appeal Brief filed Jan. 30, 2012, in U.S. Appl. No. 12/089,891 (23 pgs.).

(56) References Cited

OTHER PUBLICATIONS

Ashton, et al., "Mode of Action of Herbicides," *John Wiley & Sons*, vii-viii (1981).
Balthazor et al., "Glyphosate-Degrading Microorganisms from Industrial Activated Sludge," *Applied Environ. Microbiol.*, 51(2):432-434 (1986).
Bishop, "Two Teams Place Genes Into Corn," *The Wall Street Journal*, B1 (1990).
Chasan, "Transforming Maize Transformation," *The Plant Cell*, 4:1463-1464 (1992).
Chen et al., "Expression of CP4 EPSPS in microspores and tapetum cells of cotton (Gossypium hirsutum) is critical for male reproductive development in response to late-stage glyphosate applications," *Plant Biotech. J.*, 4:477-487 (2006).
Christou et al., "Stable Transformation of Soybean Callus by DNA-Coated Gold Particles," *Plant Physiol*, 87:671-674 (1988).
Christou, "Genetic transformation of crop plants using microprojectile bombardment," *The Plant Journal*, 2(3):275-281 (1992).
Clark, "Biotech Advance in Corn," *AG Consultant*, 12 (1990).
Cocking et al., "Gene Transfer in Cereals," *Science Mag.*, 236:1259-1262 (1987).
Comai et al., "An Altered aroA Gene Product Confers Resistance to the Herbicide Glyphosate," 221:370-371 (1983).
Comai et al., "Expression in plants of a mutant aroA gene from *Salmonella typhimurium* confers tolerance to glyphosate," *Nature*, 317:741-744 (1985).
Communication pursuant to Article 94(3) EPC dated Apr. 24, 2014, in European Patent Application No. 06 815 113.3 (4 pgs.).
Communication pursuant to Article 94(3) EPC dated Aug. 5, 2010, in European Patent Application No. 06 815 113.3 (4 pgs.).
Communication pursuant to Article 94(3) EPC dated Dec. 23, 2014, in European Patent Application No. 06 815 113.3 (4 pgs.).
Communication pursuant to Article 94(3) EPC dated Nov. 11, 2011, in European Patent Application No. 06 815 113.3 (4 pgs.).
Communication pursuant to Article 94(3) EPC dated Nov. 12, 2012, in European Patent Application No. 06 815 113.3 (4 pgs.).
D'Amato et al., "Subcellular localization of chorismate-mutase isoenzymes in protoplasts from mesophyll and suspension-cultured cells of *Nicotiana Silvestris*," *Planta*, 162:104-108 (1984).
D'Halluin et al., "Transgenic Maize Plants by Tissue Electroporation," *The Plant Cell*, 4:1495-1505(1992).
De Block et al., "Engineering herbicide resistance in plants by expression of a detoxifying enzyme," *The EMBO Journal*, 6(9):2513-2518 (1987).
De Block et al., "Transformation of *Brassica napus* and *Brassica oleracea* Using Agrobacterium tumefaciens and the Expression of the bar and neo Genes in the Transgenic Plants," *Plant Physiol.*, 91:694-701 (1989).
Devine, "Why are there not more herbicide-tolerant crops?" *Pest Manag. Sci.*, 61:312-317 (2005).
EMBL Online Database Accession No. BZ797057, "PUGBJ25TD ZM_0.6_1.0_KB *Zea mays* genomic clone ZMMBTa329F02, DNA sequence," pp. 1 (2003).
Esquela-Kerscher et al., "The age of high-throughput microRNA profiling," *Nature Methods*, 1(2): 106-107 (2004).
Evans, "Somaclonal Variation—Genetic Basis and Breeding Applications," *Trends in Genetics*, 5:46-50 (1989).
Examiner's Report dated Aug. 5, 2010, as received in Australian Patent Application No. 2006302969 (2 pgs.).
Extended European Search Report dated Feb. 18, 2015, in European Patent Application No. 12 80 7530.6 (8 pgs.).
Extended European Search Report dated Jul. 29, 2009, in European Patent Application No. 06 81 5113.3 (8 pgs.).
Final Office Action dated Jan. 2, 2015, in U.S. Appl. No. 13/677,607 (23 pgs.).
Final Office Action dated Mar. 11, 2010 in U.S. Appl. No. 11/524,564 (11 pgs.).
Final Office Action dated Mar. 29, 2011, in U.S. Appl. No. 12/089,891 (18 pgs.).

First Office Action dated Oct. 12, 2010, as received in Chinese Patent Application No. 200680046237.7 (17 pgs.).
Fraley et al., "Expression of bacterial genes in plant cells," *PNAS*, 80:4803-4807 (1983).
Fransz et al., Isozymes as biochemical and cytochemical markers in embryogenic callus cultures of maize (*Zea mays* L.), *Plant Cell Reports*, 8:67-70 (1989).
Frascaroli et al., "Variability of pollen and plant responses to glyphosate in maize," *J Genet. & Breed*, 46:4-56 (1992).
Fromm et al., "Inheritance and Expression of Chimeric Genes in the Progeny of Transgenic Maize Plants," *Biotechnology*, 8:833-839 (1990).
Fromm, "Gene guns succeed in altering corn," *Biotechnology*, 10(11):2-3 (1990).
Fujiyama, GenBank Accession No. AG057893, pp. 1-2 (2001).
Gandikota et al., "The miRNA 156/157 recognition element in the 3'UTR of the *Arabidopsis* SMP box gene SPL3 prevents early flowering by translational inhibition in seedling," *The Plant Journal*, 49:683-693 (2007).
Goodman et al., "Gene Transfer in Crop Improvement," *Science*, 236(4797):48-54 (1987).
Gordon-Kamm et al., "Transformation of Maize Cells and Regeneration of Fertile Transgenic Plants," *The Plant Cell*, 2:603-618 (1990).
Guilley et al., "Transcription of Cauliflower Mosaic Virus DNA: Detection of Promoter Sequences, and Characterization of Transcripts," *Cell*, 30:763-773 (1982).
Gunset, "Corn Farmers See Economic, Environmental Gold In Designer Genes," *Chicago Tribune*, (1991).
Gunset, "Genetic Advance May Transform Corn," *Chicago Tribune*, (1990).
Hallas et al., "Characterization of microbial traits associated with glyphosat biodegradation in industrial activated sludge," *J Industrial Microbial.*, 3:377-385 (1988).
Hamilton et al., "Two classes of short interfering RNA in RNA silencing," *The EMBO Journal*, 21 (17):4671-4679 (2002).
Han et al., "Relationship between small antisense RNAs and aberrant RNAs associated with sense transgene mediated gene silencing in tomato," *The Plant Journal*, 29(4):509-519 (2002).
Hansen et al., "Recent advances in the transformation of plants," *Trends in Plant Science*, 4(6)226-231 (1999).
International Search Report dated Oct. 19, 2007, in International Patent Appln. No. PCT/US2006/036847 (7 pgs.).
International Search Report dated Sep. 28, 2012, in International Patent Appln. No. PCT/US2012/045040 (10 pgs.).
Jacob et al., "Metabolism o glyphosate in *Pseudomonas* sp. Strain LBr.," *Applied Environ. Microbiol.*, 54(12):2953-2958 (1988).
Jensen, "The shikimate/arogenate pathway: Link between carbohydrate metabolism and secondary metabolism," *Physiol Plant*, 66:164-168 (1985).
Johnson et al., "CSRDB: a small RNA integrated database and browser resource for cereals," *Nucleic Acids Research, Database Issue*:D1-D5 (2006).
Keystone Crops, "Ecogen and Evans Biocontrol: The Failure of a "Low-Risk" Strategy," *Agricultural Genetics Report*, 9:2-3 (1990).
Kidner et al., "Spatially restricted microRNA directs leaf polarity through ARGONAUTE1," *Nature*, 428:81-84 (2004).
Klahre et al., "High molecular weight RNAs and small interfering RNAs induce systemic posttranscriptional gene silencing in plants," *PNAS*, 99(18):11981-11986 (2002).
Klein et al., "Applications of the Particle Gun in Plant Biology," *Progress in plant, papers*, 56-66 (1990).
Klein et al., "Genetic Transformation of Maize Cells by Particle Bombardment," *Plant Physiol.*, 91:440-444 (1989).
Klein et al., "Genetic Transformation of Maize Cells by Particle Bombardment and the Influence of Methylation on Foreign-Gene Expression," *Pletnum Press*, 265-288 (1990).
Kumpatla et al., "Genome intruder scanning and modulation systems and transgene silencing," *Trends in Plant Science*, 3(3):97-104 (1998).
Leemans, "Genetic engineering for fertility control," *In Vitro Cellular & Develop. Biol.*, 28(3):51A(1992).

(56) References Cited

OTHER PUBLICATIONS

Lemaux et al., "Selection of Stable Transformants from Maize Suspension Cultures using the Herbicide Bialaphos," *J Cellular Biochem.*, 44(14E):304 (1990).

Liu et al., "Degradation of the Herbicide Glyphosate by Members of the Family Rhizobiaceae," *Applied Environ. Microbiol.*, 57(6):1799-1804 (1991).

Mallory et al., "MicroRNA-Directed Regulation of *Arabidopsis* Auxin Response FACTOR17 is Essential for Proper Development and Modulates Expression of Early Auxin Response Genes," *The Plant Cell*, 17:1360-1375 (2005).

Mansoor et al., "Engineering novel traits in plants through RNA interference," *Trends Plant Sci.*, 11(11):559-565 (2006).

Marshall et al., "Studies on the Mode of Action of Asulam, Aminotriazole and Glyphosate in *Equisetum arvense* L. (Field Horsetail). II: The Metabolism of [$^{14}$C]Asulam, [$^{14}$C]Aminotriazole and [$^{14}$C]Glyphosate," *Pestic. Sci.*, 18:65-77 (1987).

McElroy et al., "Isolation of an Efficient Actin Promoter for Use in Rice Transformation," *The Plant Cell*, 2:163-171 (1990).

Meyer, "Understanding and controlling transgene expression," *Trends in Biotech.*, 13(9):332-337 (1995).

Millar et al., "The *Arabidopsis* GAMYB-Like Genes, MYB33 and MYB65, Are MicroRNA-Regulated Genes That Redundantly Facilitate Anther Development," *The Plant Cell*, 17:705-721 (2005).

miRBASE Online Database Accession No. MI0001773, "Stem-loop sequence gma-MIR159a," undated.

Moffat, "Corn Transformed," *Science*, 249:630 (1990).

Molnar et al., "Silencing signals in plants: a long journey for small RNAs," Genome Biology, 12:215, pp. 1-8 (2011).

Mousdale et al., "Subcellular localization of the common shikimate-pathway enzymes in *Pisum sativum* L.," *Planta*, 163:241-249 (1985).

Murakami et al., "The bialaphos biosynthetic genes of Streptomyces hygroscopicus: Molecular cloning and characterization of the gene cluster," *Mol Gen Genet*, 205:42-50 (1986).

Murray et al., "Codon usage in plant genes," *Nucleic Acids Research*, 17(2):477-498 (1989).

Nafziger et al., "Selection and Characterization of a Carrot Cell Line Tolerant to Glyphosate," *Plant. Physiol.*, 76:571-574 (1984).

Netzer, "A tobacco plant that has been induced to regenerate in a flask," *Biotechnology*, 2(11):937-944 (1984).

Nobuta et al., "Distinct size distribution of endogeneous siRNAs in maize: Evidence from deep sequencing in the mop1-1 mutant," *PNAS*, 105(39):14958-14963 (2008).

Non-Final Office Action dated Apr. 20, 2012, in U.S. Appl. No. 12/089,891 (19 pgs.).

Non-Final Office Action dated Aug. 18, 2009, in U.S. Appl. No. 11/303,745 (8 pgs.).

Non-Final Office Action dated Jul. 1, 2009, in U.S. Appl. No. 11/524,564 (15 pgs.).

Non-Final Office Action dated Jul. 29, 2010, in U.S. Appl. No. 12/089,891 (17 pgs.).

Non-Final Office Action dated Jul. 3, 2014, in U.S. Appl. No. 13/677,607 (17 pgs.).

Non-Final Office Action dated Nov. 28, 2008, in U.S. Appl. No. 11/303,745 (28 pgs.).

Notice of Non-Compliant Amendment dated Oct. 13, 2010, in U.S. Appl. No. 12/089,891 (2 pgs.).

Notice of Reexamination dated Apr. 9, 2015, as received in Chinese Patent Application No. 200680046237.7 (11 pgs.).

Notification dated Apr. 28, 2015, as received in Eurasian Patent Application No. 200801074 (3 pgs.).

Nuovo et al., "A methodology for the combined in situ analyses of the precursor and mature forms of microRNAs and correlation with their putative targets," *Nat Protoc.*, 4(1):107-115 (2009).

Office Action dated Oct. 12, 2010, as received in Ukrainian Patent Application No. 200806024 (7 pgs.).

Office Action dated Feb. 13, 2012, as received in Canadian Patent Application No. 2,625,031 (3 pgs.).

Office Action dated Jul. 30, 2014, as received in Canadian Patent Application No. 2,625,031 (2 pgs.).

Office Action dated Mar. 26, 2013, as received in Canadian Patent Application No. 2,625,031 (2 pgs.).

Official Action dated Mar. 16, 2010, as received in Eurasian Patent Application No. 200801074 (6 pgs.).

Omirulleh et al., "Activity of a chimeric promoter with the doubled CaMV 35S enhancer element in protoplast-derived cells and transgenic plants in maize," *Plant Molecular Biology*, 21:415-428(1993).

Oommen et al., "The Elicitor-Inducible Alfalfa Isoflavone Reductase Promoter Confers Different Patterns of Developmental Expression in Homologous and Heterologous Transgenic Plants," *The Plant Cell*, 6:1789-1803 (1994).

Padgette et al., "New Weed Control Opportunities: Development of Soybeans with a Roundup Ready Gene," *Herbicide-Resistant Crops*, 4:53-84 (1996).

Pang et al., "Nontarget DNA sequences reduce the transgene length necessary for RNA-mediated tospovirus resistance in transgenic plants," *Proc. Natl. Acad. Sci.*, 94:8261-8266 (1997).

Parizotto et al., "In vivo investigation of the transcription, processing, endonucleolytic activity, and functional relevance of the spatial distribution of a plant miRNA," *Genes Dev.*, 18:2237-2242 (2004).

Phillips et al., "Cell/tissue Culture and In Vitro Manipulation," *Corn and Corn Improvement*, 345-387 (1988).

Pipke et al., "Degradation of the Phosphonate Herbicide Glyphosate by Arthrobacter atrocyaneus ATCC 13752," *Applied Environ. Microbiol.*, 54(5):1293-1296 (1988).

Privalle et al., "Development of an Agricultural Biotechnology Crop Product: Testing from Discovery to Commercialization," *J Agric. Food Chem.*, 60:10179-10187 (2012).

Puchta et al., "From centiMorgans to base pairs: homologous recombination in plants," *Trends in Plant Science*, 1(10):340-348 (1996).

Record of Interview, Preliminary Amendment and Supplemental Response to Restriction Requirement filed Apr. 24, 2009, in U.S. Appl. No. 11/524,564 (29 pgs.).

Response to Notice of Non-Compliant Reply and Amendment filed Feb. 14, 2011, in U.S. Appl. No. 12/089,891 (17 pgs.).

Response to Office Action and Amendment filed Dec. 1, 2009, in U.S. Appl. No. 11/524,564 (16 pgs.).

Response to Office Action and Amendment filed Jul. 20, 2012, in U.S. Appl. No. 12/089,891 (7 pgs.).

Response to Office Action and Amendment filed Oct. 3, 2014, in U.S. Appl. No. 13/677,607 (17 pgs.).

Response to Restriction Requirement dated Feb. 10, 2009 filed Apr. 10, 2009, in U.S. Appl. No. 11/524,564 (5 pgs.).

Restriction Requirement dated Feb. 10, 2009, in U.S. Appl. No. 11/524,564 (6 pgs.).

Rogers et al., "Amplification of the aroA gene from *Escherichia coli* results in tolerance to the herbicide glyphosate," *Applied Environ. Microbiol.*, 46(1):37-43 (1983).

Ross et al., "Transient and Stable Transgenic Cells and Calli of Tobacco and Maize following Microprojectile Bombardment," *J Cellular Biochem.*, 41(13D):268 (1989).

Rothe et al., "Evidence for an intra- and extraplastidic pre-chorismate pathway," Planta, 157:358-366 (1983).

Rubin et al., "Enzymological Basis for Herbicidal Action of Glyphosate," *Plant Physiol.*, 70:833-839 (1982).

Rubin et al., "Glyphosate Inhibition of 5-Enolpyruvylshikimate 3-Phosphate Synthase from Suspension-Cultured Cells of Nicotiana Silvestris," *Plant Physiol.*, 75:839-845 (1984).

Saijo et al., "Some properties of the Initial Four Enzymes Involved in Shikimic Acid Biosynthesis in Tea Plant," *Agric. Biol. Chem.*, 43(7):1427-1432 (1979).

Schmidt et al., "Rapid degradation of unassembled ribulose 1,5-bisphosphate carboxylase small subunits in chloroplasts," *PNAS*, 80:2632-2636 (1983).

Schowanek et al., "Phosphonate utilization by bacterial cultures and enrichments from environmental samples," *Appl. Environ. Microbiol.*, 56(4):895-903 (1990).

Second Office Action dated Mar. 19, 2012, as received in Chinese Patent Application No. 200680046237.7 (17 pgs.).

(56) References Cited

OTHER PUBLICATIONS

Second Preliminary Amendment filed Aug. 2, 2010, in U.S. Appl. No. 12/089,891 (7 pgs.).
Shah et al., "Engineering Herbicide Tolerance in Transgenic Plants," *Science*, 233:478-481 (1986).
Simon et al., "Small RNA-mediated epigenetic modifications in plants," Current Opinion in *Plant Biology*, 14:148-155 (2011).
Singh et al., "Chorismate Mutase Isoenzymes from Sorghum bicolor: Purification and Properties," *Archives of Biochem. & Biophysics*, 243(2):374-384 (1985).
Smart et al., "Selective Overproduction of 5-enol-Pyruvylshikimic Acid 3-Phosphate Synthase in a Plant Cell Culture Which Tolerates High Doses of the Herbicide Glyphosate," *J Biol. Chem.*, 260(30):16338-16346 (1985).
Spencer et al., "Bialaphos selection of stable transformants from maize cell culture," *Theor Appl Genet*, 79:625-631 (1990).
Spencer et al., "Segregation of transgenes in maize," *Plant Molecular Biol.*, 18:201 210 (1992).
Stalker et al., "A Single Amino Acid Substitution in the Enzyme 5-Enolpyruvylshikimate-3-phospate Synthase Confers Resistance to the Herbicide Glyphosate," *J Biol. Chem.*, 260(8):4724-4728 (1985).
Sun, "Engineering Crops to Resist Weed Killers," *Science*, 231:1360-1361 (1986).
Thierry et al., "Sequence homology requirements for transcriptional silencing of 35S transgenes and post-transcriptional silencing of nitrite reductase (trans)genes by the tobacco 271 locus", *Plant Molecular Biol.*, 32:1075-1083 (1996).
Third Office Action dated Nov. 16, 2012, as received in Chinese Patent Application No. 200680046237.7 (14 pgs.).
Thomas et al., "Size constraints for targeting post-transcriptional gene silencing and for RNA-directed methylation in Nicotiana benthamiana using a potato virus X vector," *The Plant Journal*, 25(4):417-425 (2001).
Thompson et al., "Characterization of the herbicide-resistance gene bar from Streptomyces hygroscopicus," *The EMBO Journal*, 6(9):2519-2523 (1987).
Torres, "Practical and Applied Biotechnology: How to Make a Transgenic Plant," Bioreactorcrc, WordPress, pp. 1-22 (2008) <https://bioreactorcrc.wordpress.com/2008/02/02/comosehaceunaplantatransgenica/>.
Valoczi et al., "Spatio-temporal accumulation of mircoRNAs is highly coordinated in developing plant tissues," *The Plant Journal*, 47:140-151 (2006).
Van Den Broek et al., "Targeting of a foreign protein to chloroplasts by fusion to the transit peptide from the small subunit of ribulose 1,5-biphosphate carboxylase," *Nature*, 313:358-363 (1985).
Wan et al., "Generation of Large Numbers of Independently Transformed Fertile Barley Plants," *Plant Physiol.*, 104:37-48 (1994).

Wang et al., "Control of Root Cap Formation by MicroRNA-Targeted Auxin Response Factors in *Arabidopsis*," *The Plant Cell*, 17:2204-2216 (2005).
Wang et al., "Development and validation of vectors containing multiple siRNA expression cassettes for maximizing the efficiency of gene silencing," *BMS Biotech.*, 6:50 (2006).
Weidhase et al., "Utilization of Glyphosate by *Pseudomonas* spec. GS," *Zentralbl. Mikroblol.*, 145:433-438 (1990).
Weising et el., "Foreign Genes In Plants: Transfer, Structure, Expression, and Applications," *Annu. Rev. Genet.*, 22:421-477 (1988).
White et al., "A cassette containing the bar gene of *Streptomyces hygroscopicus*: a selectable marker for plant transformation," *Nucleic Acids Research*, 18(4):1062 (1990).
Wu et al., "Temporal regulation of Shoot Development in *Arabidopsis thaliana* by Mir156 and Its Target SPL3," *Development*, 133(18):3539-3547 (2006).
Xie et al., "Expression of *Arabidopsis* MIRNA Genes," *Plant Phys.*, 138:2145-2154 (2005).
Johnson et al., "CSRDB: a small RNA integrated database and browser resource for cereals," *Nucleic Acids Research*, 35:D829-D833, 2007.
Chilean Office Action regarding Application No. 3776-2013, dated Jul. 12, 2016.
Chuck et al., Nature Genetics, 39:544-549 (2007).
Howe et al. Molecular Breeding, 10:153-164 (2002).
Grant-Downton et al., *Biomolecules*, 2:608-621 (2012).
Omidvar et al., BMC Genomics, 1-16 (2015).
Li et al., BMC Genomics, 18:1-18 (2017).
Office Action regarding Russian Application No. 2014103436, dated Dec. 26, 2017.
Tarantul V.Z. Biotechnological definition dictionary Russian-English, 2009, Moscow, sheets 936 (p. 396).
Chellapan et al., "siRNAs from miRNA sites mediate DNA methylation of target genes," *Nucleic Acids Research* 38:6883-6894, 2010.
GenBank Accession No. EU974548, dated Dec. 5, 2008.
U.S. Appl. No. 16/844,949, filed Apr. 9, 2020, Huang et al.
USPTO: Restriction Requirement regarding U.S. Appl. No. 16/844,949, dated Dec. 9, 2021.
USPTO: Response to Restriction Requirement regarding U.S. Appl. No. 16/844,949, filed Feb. 7, 2022.
USPTO: Response to Non-Final Office Action regarding U.S. Appl. No. 16/844,949, filed Jul. 11, 2022.
USPTO: Non-Final Office Action regarding U.S. Appl. No. 16/844,949, dated Apr. 15, 2022.
U.S. Appl. No. 17/816,905, filed Aug. 2, 2022, Feng et al.
USPTO: Non-Final Office Action regarding U.S. Appl. No. 16/844,949, dated Oct. 21, 2022.

\* cited by examiner

| Sample # | LMW sample name |
|---|---|
| 1 | 91DUA6 Young tassel |
| 2 | 01DKD2 Young tassel |
| 3 | LH244 Young tassel |
| 4 | 91DUA6 Old tassel |
| 5 | 01DKD2 Old tassel |
| 6 | LH244 Old tassel |
| 7 | 91DUA6 Leaf |
| 8 | 01DKD2 Leaf |
| 9 | LH244 Leaf |
| 10 | 91DUA6 Ear |
| 11 | 01DKD2 Ear |
| 12 | LH244 Ear |
| 13 | 91DUA6 Root |
| 14 | 01DKD2 Root |
| 15 | LH244 Root |

| Lane | Inbred |
|---|---|
| 1 | C3SUD402 |
| 2 | HIQA202 |
| 3 | BEBE788 |
| 4 | BIQA207 |
| 5 | DIDA404 |
| 6 | 5DA92 |
| 7 | DIDA406 |
| 8 | 80DJD5 |
| 9 | JEDO115 |
| 10 | FIDA240 |
| 11 | BIQA347 |
| 12 | HOQA203 |
| 13 | 91DUA6 |
| 14 | BIDA345 |
| 15 | 01DKD2 |
| 16 | DIDA403 |
| 17 | 64DJD1 |
| 18 | DIQA423 |
| 19 | BIQA208 |
| 20 | LH244 |
| 21 | BIQA208 - leaf |
| 22 | LH244- leaf |
| 23 | BIQA208 - ear |
| 24 | LH244 -ear |

Construct 3

Construct 4

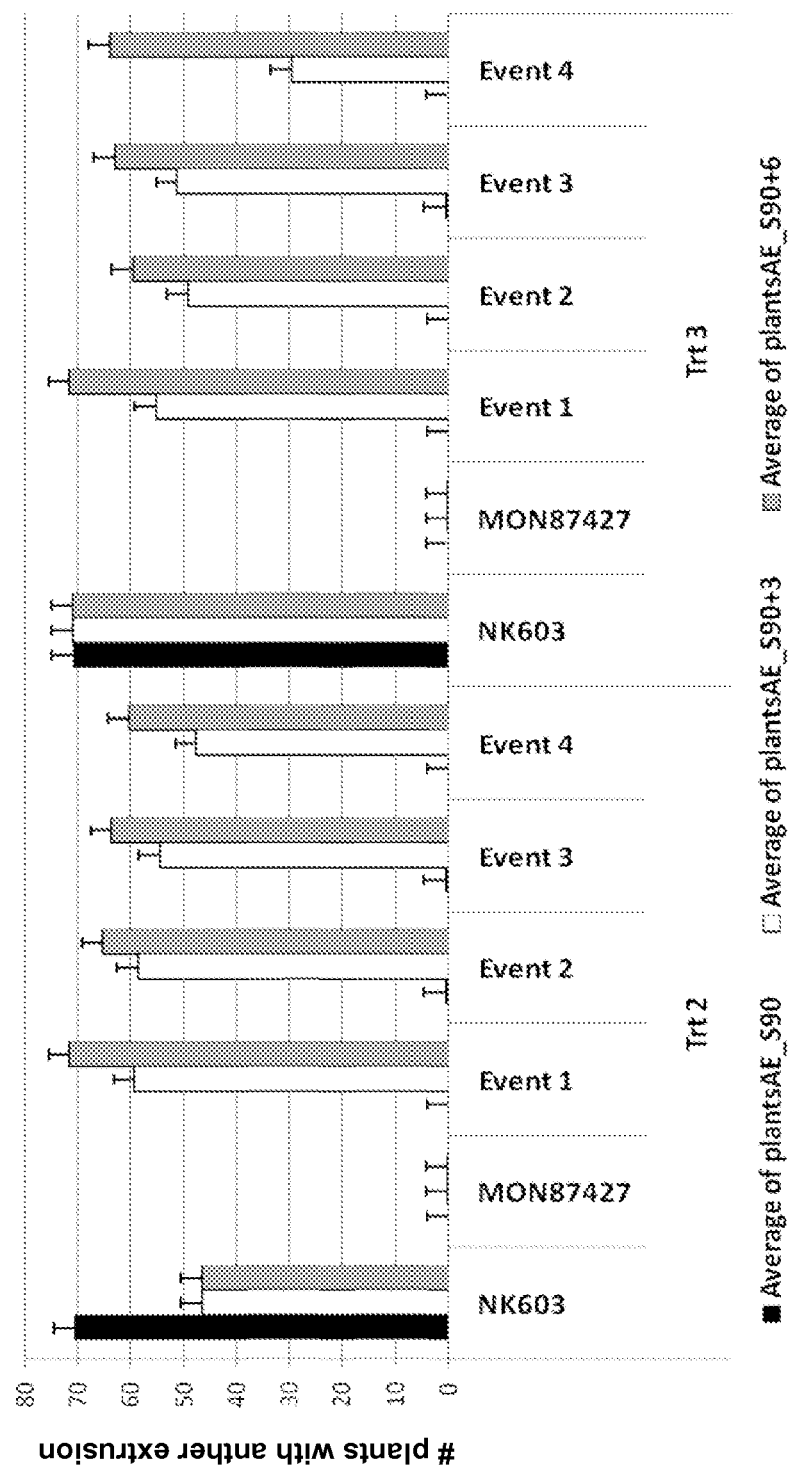

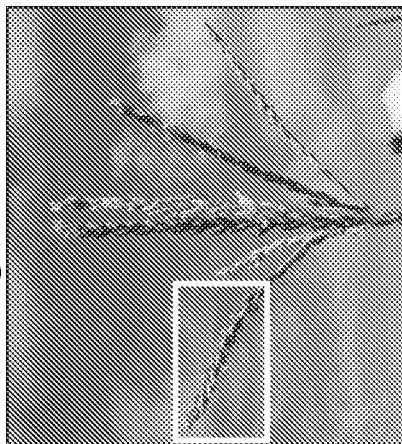
Figure 10A
Figure 10B
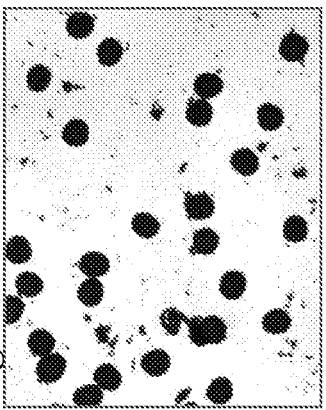
Figure 10D
Non-sprayed:
Pollen viable
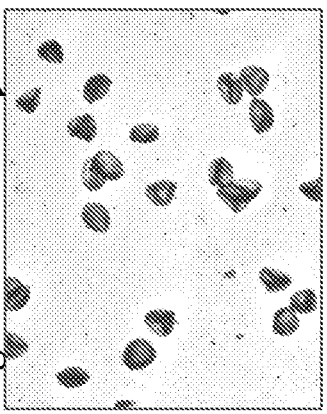
Figure 10C
Sprayed:
Pollen not viable Figure 13
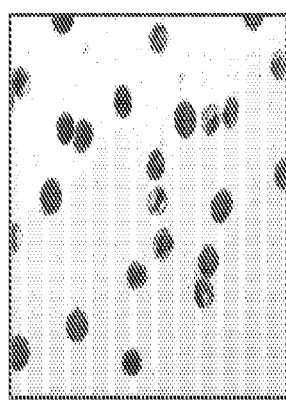 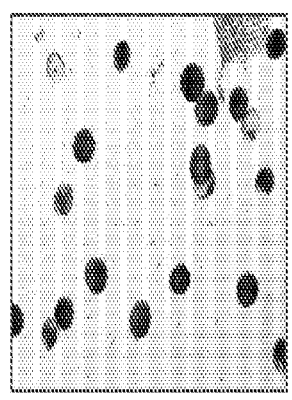 
Null x MON88017   MON87427 x MON88017   Event 3 x MON88017

Figure 14

| promoter | protein-coding sequence | mts-siRNA element* | 3' UTR |

*one or more selected from SEQ ID NOs:57-94 and 96-104

| promoter | intron | transit peptide | SEQ ID NO:95 | SEQ ID NO:81 | 3' UTR |

SEQUENCE LISTING

<160> NUMBER OF SEQ ID NOS: 154

<210> SEQ ID NO 1
<211> LENGTH: 23
<212> TYPE: DNA
<213> ORGANISM: Zea mays

<400> SEQUENCE: 1
catgcactgg tgagtcactg ttg                                           23

<210> SEQ ID NO 2
<211> LENGTH: 20
<212> TYPE: DNA
<213> ORGANISM: Zea mays

<400> SEQUENCE: 2
acagtgactc accagtgcat                                               20

<210> SEQ ID NO 3
<211> LENGTH: 23
<212> TYPE: DNA
<213> ORGANISM: Zea mays

<400> SEQUENCE: 3
ggcctccctt ccctatggta gcc                                           23

<210> SEQ ID NO 4
<211> LENGTH: 24
<212> TYPE: DNA
<213> ORGANISM: Zea mays

<400> SEQUENCE: 4
aagctattga ttccctaagt gcca                                          24

<210> SEQ ID NO 5
<211> LENGTH: 18
<212> TYPE: DNA
<213> ORGANISM: Zea mays

<400> SEQUENCE: 5
aggcctccct tccctatg                                                 18

<210> SEQ ID NO 6
<211> LENGTH: 24
<212> TYPE: DNA
<213> ORGANISM: Zea mays

<400> SEQUENCE: 6
acagtgactc accagtgcat gcac                                          24

<210> SEQ ID NO 7
<211> LENGTH: 20
<212> TYPE: DNA
<213> ORGANISM: Zea mays

<400> SEQUENCE: 7
catccgccca ttcttcagtc                                               20

<210> SEQ ID NO 8
<211> LENGTH: 21
<212> TYPE: DNA
<213> ORGANISM: Zea mays

<400> SEQUENCE: 8

```
acagtgactc accagtgcat g                                          21

<210> SEQ ID NO 9
<211> LENGTH: 23
<212> TYPE: DNA
<213> ORGANISM: Zea mays

<400> SEQUENCE: 9
aaggcaagaa ggtgcttgtt gtc                                        23

<210> SEQ ID NO 10
<211> LENGTH: 24
<212> TYPE: DNA
<213> ORGANISM: Zea mays

<400> SEQUENCE: 10
gcatgcactg gtgagtcact gttg                                       24

<210> SEQ ID NO 11
<211> LENGTH: 21
<212> TYPE: DNA
<213> ORGANISM: Zea mays

<400> SEQUENCE: 11
atcaacgact acaacggtga a                                          21

<210> SEQ ID NO 12
<211> LENGTH: 23
<212> TYPE: DNA
<213> ORGANISM: Zea mays

<400> SEQUENCE: 12
gcatgcactg gtgagtcact gtt                                        23

<210> SEQ ID NO 13
<211> LENGTH: 25
<212> TYPE: DNA
<213> ORGANISM: Zea mays

<400> SEQUENCE: 13
caaggcaaga aggtgcttgt tgtcc                                      25

<210> SEQ ID NO 14
<211> LENGTH: 22
<212> TYPE: DNA
<213> ORGANISM: Zea mays

<400> SEQUENCE: 14
catcaacgac tacaacggtg aa                                         22

<210> SEQ ID NO 15
<211> LENGTH: 24
<212> TYPE: DNA
<213> ORGANISM: Zea mays

<400> SEQUENCE: 15
accatcaacg actacaacgg tgaa                                       24

<210> SEQ ID NO 16
<211> LENGTH: 24
<212> TYPE: DNA
<213> ORGANISM: Zea mays
```

```
<400> SEQUENCE: 16
aggcctccct tccctatggt agcc                                          24

<210> SEQ ID NO 17
<211> LENGTH: 22
<212> TYPE: DNA
<213> ORGANISM: Zea mays

<400> SEQUENCE: 17
gcatgcactg gtgagtcact gt                                            22

<210> SEQ ID NO 18
<211> LENGTH: 19
<212> TYPE: DNA
<213> ORGANISM: Zea mays

<400> SEQUENCE: 18
aaggcctccc ttccctatg                                                19

<210> SEQ ID NO 19
<211> LENGTH: 18
<212> TYPE: DNA
<213> ORGANISM: Zea mays

<400> SEQUENCE: 19
caaggcaaga aggtgctt                                                 18

<210> SEQ ID NO 20
<211> LENGTH: 24
<212> TYPE: DNA
<213> ORGANISM: Zea mays

<400> SEQUENCE: 20
aaggcaagaa ggtgcttgtt gtcc                                          24

<210> SEQ ID NO 21
<211> LENGTH: 25
<212> TYPE: DNA
<213> ORGANISM: Zea mays

<400> SEQUENCE: 21
aaggcctccc ttccctatgg tagcc                                         25

<210> SEQ ID NO 22
<211> LENGTH: 21
<212> TYPE: DNA
<213> ORGANISM: Zea mays

<400> SEQUENCE: 22
ctattgattc cctaagtgcc a                                             21

<210> SEQ ID NO 23
<211> LENGTH: 18
<212> TYPE: DNA
<213> ORGANISM: Zea mays

<400> SEQUENCE: 23
aagaaggtgc ttgttgtc                                                 18

<210> SEQ ID NO 24
<211> LENGTH: 23
<212> TYPE: DNA
<213> ORGANISM: Zea mays
```

```
<400> SEQUENCE: 24
aacaagcacc ttcttgcctt gca                                           23

<210> SEQ ID NO 25
<211> LENGTH: 23
<212> TYPE: DNA
<213> ORGANISM: Zea mays

<400> SEQUENCE: 25
caaggcaaga aggtgcttgt tgt                                           23

<210> SEQ ID NO 26
<211> LENGTH: 24
<212> TYPE: DNA
<213> ORGANISM: Zea mays

<400> SEQUENCE: 26
caaggcaaga aggtgcttgt tgtc                                          24

<210> SEQ ID NO 27
<211> LENGTH: 24
<212> TYPE: DNA
<213> ORGANISM: Zea mays

<400> SEQUENCE: 27
accaaggatg tcgtcaccac caat                                          24

<210> SEQ ID NO 28
<211> LENGTH: 24
<212> TYPE: DNA
<213> ORGANISM: Zea mays

<400> SEQUENCE: 28
caacaagcac cttcttgcct tgca                                          24

<210> SEQ ID NO 29
<211> LENGTH: 21
<212> TYPE: DNA
<213> ORGANISM: Zea mays

<400> SEQUENCE: 29
accatcaacg actacaacgg t                                             21

<210> SEQ ID NO 30
<211> LENGTH: 21
<212> TYPE: DNA
<213> ORGANISM: Zea mays

<400> SEQUENCE: 30
aagctatcga ttccctaagt g                                             21

<210> SEQ ID NO 31
<211> LENGTH: 23
<212> TYPE: DNA
<213> ORGANISM: Zea mays

<400> SEQUENCE: 31
agctatcgat tccctaagtg cca                                           23

<210> SEQ ID NO 32
<211> LENGTH: 25
<212> TYPE: DNA
```

```
<213> ORGANISM: Zea mays

<400> SEQUENCE: 32
aaagctatcg attccctaag tgcca                                    25

<210> SEQ ID NO 33
<211> LENGTH: 24
<212> TYPE: DNA
<213> ORGANISM: Zea mays

<400> SEQUENCE: 33
aagctatcga ttccctaagt gcca                                     24

<210> SEQ ID NO 34
<211> LENGTH: 24
<212> TYPE: DNA
<213> ORGANISM: Zea mays

<400> SEQUENCE: 34
aggcaagaaa gtgcttgttg tcgg                                     24

<210> SEQ ID NO 35
<211> LENGTH: 24
<212> TYPE: DNA
<213> ORGANISM: Zea mays

<400> SEQUENCE: 35
tggctaattg ttgccaccag agag                                     24

<210> SEQ ID NO 36
<211> LENGTH: 25
<212> TYPE: DNA
<213> ORGANISM: Zea mays

<400> SEQUENCE: 36
aagctattga ttcccgtaag tgcca                                    25

<210> SEQ ID NO 37
<211> LENGTH: 24
<212> TYPE: DNA
<213> ORGANISM: Zea mays

<400> SEQUENCE: 37
caaggcaaga aagtgcttgt tgtc                                     24

<210> SEQ ID NO 38
<211> LENGTH: 22
<212> TYPE: DNA
<213> ORGANISM: Zea mays

<400> SEQUENCE: 38
aagctatcga ttcactaagt gc                                       22

<210> SEQ ID NO 39
<211> LENGTH: 24
<212> TYPE: DNA
<213> ORGANISM: Zea mays

<400> SEQUENCE: 39
caaggcaaga aggttcttgt tgtc                                     24

<210> SEQ ID NO 40
<211> LENGTH: 25
```

<212> TYPE: DNA
<213> ORGANISM: Zea mays

<400> SEQUENCE: 40
caaggcgaag aaggtgcttg ttgtc                                    25

<210> SEQ ID NO 41
<211> LENGTH: 20
<212> TYPE: DNA
<213> ORGANISM: Zea mays

<400> SEQUENCE: 41
caaggatttc atcaccacca                                          20

<210> SEQ ID NO 42
<211> LENGTH: 18
<212> TYPE: DNA
<213> ORGANISM: Zea mays

<400> SEQUENCE: 42
cgaagaaggt gcttgttg                                            18

<210> SEQ ID NO 43
<211> LENGTH: 22
<212> TYPE: DNA
<213> ORGANISM: Zea mays

<400> SEQUENCE: 43
aagctatcga ttccctaagt gc                                       22

<210> SEQ ID NO 44
<211> LENGTH: 23
<212> TYPE: DNA
<213> ORGANISM: Zea mays

<400> SEQUENCE: 44
ttaatgtcat tgccgccgag tac                                      23

<210> SEQ ID NO 45
<211> LENGTH: 23
<212> TYPE: DNA
<213> ORGANISM: Zea mays

<400> SEQUENCE: 45
aatgactcat tgttgccacc aga                                      23

<210> SEQ ID NO 46
<211> LENGTH: 20
<212> TYPE: DNA
<213> ORGANISM: Zea mays

<400> SEQUENCE: 46
tggtggtgat gaaatccttg                                          20

<210> SEQ ID NO 47
<211> LENGTH: 24
<212> TYPE: DNA
<213> ORGANISM: Zea mays

<400> SEQUENCE: 47
gcatgcactg gtgattcact gttg                                     24

<210> SEQ ID NO 48

```
<211> LENGTH: 24
<212> TYPE: DNA
<213> ORGANISM: Zea mays

<400> SEQUENCE: 48
aatgactcat tgttgccacc agag                                               24

<210> SEQ ID NO 49
<211> LENGTH: 25
<212> TYPE: DNA
<213> ORGANISM: Zea mays

<400> SEQUENCE: 49
caaggcaaga aaggtgcttg ttgtc                                              25

<210> SEQ ID NO 50
<211> LENGTH: 23
<212> TYPE: DNA
<213> ORGANISM: Zea mays

<400> SEQUENCE: 50
aaggtaagaa ggtgcttgtt gtc                                                23

<210> SEQ ID NO 51
<211> LENGTH: 25
<212> TYPE: DNA
<213> ORGANISM: Zea mays

<400> SEQUENCE: 51
aggcctccct tccctactgg tagcc                                              25

<210> SEQ ID NO 52
<211> LENGTH: 24
<212> TYPE: DNA
<213> ORGANISM: Zea mays

<400> SEQUENCE: 52
caaggcaaga agctgcttgt tgtc                                               24

<210> SEQ ID NO 53
<211> LENGTH: 24
<212> TYPE: DNA
<213> ORGANISM: Zea mays

<400> SEQUENCE: 53
caaggcaaga agttgcttgt tgtc                                               24

<210> SEQ ID NO 54
<211> LENGTH: 19
<212> TYPE: DNA
<213> ORGANISM: Zea mays

<400> SEQUENCE: 54
catcaacgac tacaatggt                                                     19

<210> SEQ ID NO 55
<211> LENGTH: 22
<212> TYPE: DNA
<213> ORGANISM: Zea mays

<400> SEQUENCE: 55
gcacggtcgt tgtctggggt tc                                                 22
```

```
<210> SEQ ID NO 56
<211> LENGTH: 22
<212> TYPE: DNA
<213> ORGANISM: Zea mays

<400> SEQUENCE: 56
tagactagct aagtgtctgt gc                                              22

<210> SEQ ID NO 57
<211> LENGTH: 451
<212> TYPE: DNA
<213> ORGANISM: Zea mays

<400> SEQUENCE: 57
atccgctgca ggcagccaag caaagatctt tgggacaggt atatagctaa gatctttggc     60
gcttgctaga attttcggaa tagccagctg gctcgggcat ctccttgcca agatctttgg    120
gacaggtgac caccagttgc atgggtgaat cccagacgac gaccacatct gatgagacat    180
acacaacgtc gtcgtctttg tcatcattct acctgacagt tgagaagacg acgaccacaa    240
ctgatcagat gtacacagcg ccaccgtctt taccatcatt gtaccttaca cccaaggaga    300
cgctgaacaa tggtgtcatt tcgataagca actacaacac tgatgaagca ccttcgccgc    360
aacctgtatc gttggtatct gatgagatag acatttctga atcatcacct ccgccatctc    420
cgtcgccaca tacagtggat gagatggaca a                                   451

<210> SEQ ID NO 58
<211> LENGTH: 441
<212> TYPE: DNA
<213> ORGANISM: Zea mays

<400> SEQUENCE: 58
ctgtttgcta gaattttcgg aataggctgg ctccggcatc tccttgccaa gatctttggg     60
gcaggtgacg agttgcacgg tggtgaatcc cagacgacgg ccacatctga tgagacatac    120
acaatgccgt cgtctttgtc atcattctac ctgacagttg agaagacgat gaccacatat    180
gatgagatct acacagtgcc atcgtcttag tcatcattgt acctgacacc cgaggagacg    240
ccgaacaatg gtgccatttc gataagcaac tacgacactg atgaaccacc ttcgccgcca    300
catgtatcgt tggtatctga tgagataaac atttctgaat catcacctcc gccatctccg    360 tcgcccacata cagcggatga gatggacaac tctgaggcgt caccttcacc tttgtctcac    420
accatagaac tccaaatgtt t                                              441

<210> SEQ ID NO 59
<211> LENGTH: 321
<212> TYPE: DNA
<213> ORGANISM: Zea mays

<400> SEQUENCE: 59
aataaaccgg ctccaacacc tacttgcaaa gatatttgga accggtgacc agctgcacga     60
cgatgaatcc tacaagacga ccatgtaata cacagtgtcg tcctcttcgt tctactactc    120
aacagagcag tcgccgacca ataacgaatg gagtattatc tctgtccttc accttacacc    180
atattcacac catagaactg caaatgtccg aggtaccaac taacatcggt acctttggca    240
tgaatgatga atgaagagga cggcgatgac tatattagag aatgggaaag tgaataactg    300
ctcgatctgt cactaacaat t                                              321

<210> SEQ ID NO 60
```

<211> LENGTH: 501
<212> TYPE: DNA
<213> ORGANISM: Zea mays

<400> SEQUENCE: 60

```
aaactcaaac tctatgattt atatgttttc gctaacctac taattgattt atactcttca    60
cactaattta gattattaac caagagaact agctatcacc atttctaaat ccactatttt   120
tttactttga aaactcaatg ttgaaaagag atcaacagag acgacatcta tggcaactta   180
tgtgttcttc tgcagatgta atacgtgctc acgttcggca cccaaatgct cgtagaccat   240
ggtcaaggtg agggacgacg tgaaccttcc catctatcag ggtgacaaca tcaatggcaa   300
gacatttgac gagaagagtc atgtttggac ccatacaaga tgctttcgga gtacacccaa   360
tccgctgtca tgctcaacct actctacgcc ttctccaccg gtggctactc aacattcagc   420
gcgtcacgca gtggaaactt gatgtcaccg aacatagcaa gtagggtgac atgtgaaata   480
aaatcttcca ttcactgagt t                                             501
```

<210> SEQ ID NO 61
<211> LENGTH: 241
<212> TYPE: DNA
<213> ORGANISM: Zea mays

<400> SEQUENCE: 61

```
agcagacacc acttcacaag caggatggca atgaactctg gttgttgttt tgccagggtc    60
ccagccctat gaaagcgcgt tacgtttacg cagtgctctt tctactggcc aacttgtgtg   120
cgtggctcat gcgagagaac cgtatatcat attacttagc gcagcggggc aacgcccgct   180
gtcacggtga ccagggctgt ctcgcggctc agagcgtgct gacaattagc cagactttct   240
g                                                                   241
```

<210> SEQ ID NO 62
<211> LENGTH: 401
<212> TYPE: DNA
<213> ORGANISM: Zea mays

<400> SEQUENCE: 62

```
tcaccaaact tggaaataga ccggttcata taacaaccat caaaatccaa tatcttgatt    60
cgttatcttc tttccttacc atgcaaacac taaatacatg tagacctacg acaaaggccc   120
ccacattttt ctaggcaacc aaaatccgtg acatatacag ggatacgaag tgtcttcggt   180
tatatacagt gataacttct atgctggctg gttgagacgg acacgcttga cacatggtgc   240
ttccactcat ccacgactcc atagtcactg tcaggtcggg atcgagccat ctagacccat   300
gagaagcaag gatgcgaagg actcttcaac aattatttaa ttggacttgc tagatttagt   360
tacttatatt caatcccagt tgctctctat attaatttgg t                       401
```

<210> SEQ ID NO 63
<211> LENGTH: 466
<212> TYPE: DNA
<213> ORGANISM: Zea mays

<400> SEQUENCE: 63

```
tatttctagc cacacggtca cgtttggacg accaataata ggcttgcaac ccttcaaatt    60
gtgtccatca gcttcccaac gtgcatatcg ccatcctctg cttcgtgtcc catgtcacca   120
cccccactct tcctctttac atgcaatgca aataaagcag atccaacgtg gatgagggtg   180
aatcggatgt tgaggtgggg tctgctaaat ctcccaaata atcaaatggc ggctgcaaca   240
```

```
acacgaggga atgtcattgg tcgatgagtt ggaggcgtca aatgcagata aagctacaac    300
ttccatgtgg aggatgactg cgacgttgtg gcagactcat ccactacagt gagagtctag    360
gaaagcatga agccgattgt ggacatcgat gtcggtgtca aggacttata gatgtcatgt    420
tgggagagca accatggcac gatagttaag gcgcaagggg atctgt                   466

<210> SEQ ID NO 64
<211> LENGTH: 381
<212> TYPE: DNA
<213> ORGANISM: Zea mays

<400> SEQUENCE: 64
gcaaaatgta taggaactag ccaccatcac cactttttcta gatttggttt caggttatct    60
atgatgttct tgctccaatt tggtgtccgc aagagtcatc ccttccttgc ttcaaacaag    120
tgcaaatgtt tagcagattt acaattttttt atttgcttct ataaccatag ggaatctgct   180
ctcataataa gtgatccaga aattcaataa ttattacgag agtcgtcgtg ttagcatggg    240
attattaagg ggctctgcaa aaaatgaggc tgagcttctg gatctcgaga aaaatataaa    300
ggtctatcaa tatatgtata gtatgtatgc ttgtcaccat ttggagtcat ataatttcg     360 ccaggtgtat gtgtggttgt c                                              381

<210> SEQ ID NO 65
<211> LENGTH: 441
<212> TYPE: DNA
<213> ORGANISM: Zea mays

<400> SEQUENCE: 65
cagaagacga cgtaccatat ggcttagtac caagcagaaa gaatgccaaa ggcctagggc    60
aaattaaggg tggcaattac tagagccccg gccaggacgt gtctctgttc ttggaaagcc   120
cgaagaacgc cctctcaacg gcctgattcc cgttctaacg ctgcatcaga ttaacatcca   180
cagcacggga tgcagcggca ccatgggatg tgagcaaagc gtgtaaccaa ggcgaagaca   240
actcgaacac cattgtccgg catcctcatc aaagaacaaa gagctagcta gcgagcagcg   300
aggtatcaca gtgcaaatgc aatacagacg gacatctgaa tcggccacgt tgcatgcatg   360
tatcggacga cggggagacg agaagcacta tttagaacag gacagacac catagcttct   420 agctctgtat cgcttgggag c                                              441

<210> SEQ ID NO 66
<211> LENGTH: 451
<212> TYPE: DNA
<213> ORGANISM: Zea mays

<400> SEQUENCE: 66
tctgcaggca gccaagctag cgaagcacgg acgacaataa tgaactgtgt cttctcctgc    60
cagggcctca gccctatgaa cgtcagatac ctgtatgcgg ctatcttcct cgtggcgaac   120
ctgtctgcgt ggttcgcacg agagaacacc gtatcgtatt acctgaagca gcgactcagc   180
ggcgcctgtc agggtgaccg gggttgtctc gcggctgaaa gcgtgctcgt ggcgagccat   240
gccttctttg tatcctacag tttaaacaac attgttttttt atctaacaat tttctgtatt   300
atgattgctc tgaccttaac aaatcgtcca gctctttttt atggccatgt tcttctccac    360
tgtacgcacc ggcaaggtga atgagttgag aaattcatgg cactgcgggt ggtggccagt   420
gaagattgcc ctcttcatgg tctgttctct c                                   451
```

<210> SEQ ID NO 67
<211> LENGTH: 511
<212> TYPE: DNA
<213> ORGANISM: Zea mays

<400> SEQUENCE: 67

| ggagtgaacc aaatgagctt atgttcttat atgactacta gctagaagtt agagcctaga | 60 |
| tgatggctgc ttctgttggc gtgaaagctc gagtgctcct aaatggtcgt cgtattagct | 120 |
| gatacgacat ctacccgatg caatagataa tattgtttac acgcgtgagt ccaaaattgt | 180 |
| tggctttggg tcggagcagt taatgcgaga agtgtatttt atcacttctg agtgcaacct | 240 |
| ttttttttatt attttttccga gcttctgcct cttgcatatg ttgtagattc tcgccgagaa | 300 |
| gggagtagta gtattacctg atatctatgc taattcaggt ggtgtggtcg ttagctactt | 360 |
| taattgagtg ggttcagaac attcaaggtt tcatgtgggc cgaggagaaa gtggacgatg | 420 |
| aactagaaaa ggacatgagc agtgcttttc aacacatgaa ggccatgtgc aaatctttgg | 480 |
| tgctgccgaa gtgtgtcgtg acattggaat t | 511 |

<210> SEQ ID NO 68
<211> LENGTH: 351
<212> TYPE: DNA
<213> ORGANISM: Zea mays

<400> SEQUENCE: 68

| tatgaccatg ttcttctcca ctgtacgcac cggcaaggtg aatgagttga gaaattcatg | 60 |
| gcactccggg tggtggccag tgaagattgc cctcttcatg gtctgttctc tcatctctgt | 120 |
| cttggctcca tcctggtgga tccaaatcta tgttatgaaa cattgtagag tcagaagacg | 180 |
| acgtatcata tgggtatggc ttttttccatt tcgccttcgc ggcgggctcc atgtacgtca | 240 |
| ggatggtgtt tgtcggctgg gacacacatc atacaatgaa gcaatggagc gtggatattg | 300 |
| ggtggatgag cacgtgggtt catatcgcca atgaggctct cgtagtagta t | 351 |

<210> SEQ ID NO 69
<211> LENGTH: 431
<212> TYPE: DNA
<213> ORGANISM: Zea mays

<400> SEQUENCE: 69

| taggactgta cttgtgttgg actctaggct taagctatgt atatatatgc tagcattagg | 60 |
| acctcatatt ataataagta ttatttcaag acgaccatcc gattagtgtg gctacgtcga | 120 |
| acgcccgcgc catgattgca acattctagt ggccaatgtt gttgacttca ggcaaatcac | 180 |
| ggtggagatg ctctctcgac tagagctcgg gacgacaggg ctcaagaccc tcacgcgcga | 240 |
| ggtgatggac gtgctcatcg acaagcccaa gcatgtgaca ctcggcaggt ggaaaagacg | 300 |
| ttcttttggc ccccacaggt ctagtacgtc gttgttgatg tctatgagtt ctacaaggtt | 360 |
| ggttgtctgt tgttcatgac agagcgcacg cacagctgat ggaaggacgc cgccgtctat | 420 |
| ttgcatggag a | 431 |

<210> SEQ ID NO 70
<211> LENGTH: 461
<212> TYPE: DNA
<213> ORGANISM: Zea mays

<400> SEQUENCE: 70

| gtcggaggaa gctgctgaaa aaggttaact ttatctatgg gactaagctt caattcggca | 60 |

-continued

```
tcctcccatt cttcagtctt aatgtcgttg ccgccgagta caacagtgac tcaccagtgc      120
atgcacacca aggatgtcgt caccaccaat accatcaacg actacaacgg tgaagagttt      180
gtcttctact ctccatggga gtacggtgcc aaaacaaact caataataga ctaccacacc      240
aaccaaaatg actcattgtt gccaccagag agaatgtata gcctattatg tctggcactt      300
agggaatcga tagctttaag gtgaagtcat ccactcaagt ggctaccata gggaagggag      360
gccttgcaag gcaagaaggt gcttgttgtc cgttgtgata caccttttc aacaataatg       420 ttcataccta cattgttcgt tcgtcgttgg gtaaaaacat t                          461
```

<210> SEQ ID NO 71
<211> LENGTH: 361
<212> TYPE: DNA
<213> ORGANISM: Zea mays

<400> SEQUENCE: 71

```
tgaggatgaa gtaggtgttg cagttgctgg agtacccaaa cctgacgtag ctggagacga      60
cgctcaagac gatcgaggcc ttgctgccga tcgtctttgc tagggagaca cgacacttga      120
atgagtgcct cgtcgatacc gtcatgggtc gtgccttcct cttctagggt gacaactaag      180
ctgaaagctt caaagagttc aacatcgaca acatatgtgg caccatctgc gtcctcctac      240
agatatttgt cgtgctcacg ttcggtaccc aaatgcccgt gaaccgtggt caagatalccc     300 catctacacc atgagcagag acaacacgca aaatgagatt cctttcgctt ttgatcaaac      360
a                                                                     361
```

<210> SEQ ID NO 72
<211> LENGTH: 481
<212> TYPE: DNA
<213> ORGANISM: Zea mays

<400> SEQUENCE: 72

```
tttacaattg gatgttggtg aaagctgaaa ttacgtagag gtgtcctagt aatggaattt      60
caaagtttgg taaaaaacta ggagtcaaca tagtaaatga aatatttat gttggaatat       120 attatataca tggacacagt gatccaaccg ctatgtagtg tggttttgaac tacacaacta     180 aagtagctaa aagaatgcaa atagggggttg cgcaaaccgg cttggtggca ctttgttggt     240
ctccatgatc caagatatac tttctgggta ctgcgaaaca ccttctccta caatcaactt      300
gagatatcga gggcaagtgg gccgttcaaa gatgtattaa tgttgatatt ggtgccagtc      360
gatctactga tggtgacgat gatgaaagtg ttgacacctt tcgtcttcag gagcaacccc      420
gttcgacaag aaaatcgttg attctaaaga tctcaacgac gtttaccctg actacaacac      480
a                                                                     481
```

<210> SEQ ID NO 73
<211> LENGTH: 451
<212> TYPE: DNA
<213> ORGANISM: Zea mays

<400> SEQUENCE: 73

```
agtgatgaca agttcagaag tgtgaggagg cgtaggaaaa atacttggtt cacttcaaga      60
acatatgatg gcaagaggcg caactctaca gatatttaca acagacgcat gcatgtattc      120
tacaatgaac taactacgta tattaggttt ctccaataat gtcgacctca agatttcact      180
acaatctttt cctagcgagg tcctccgggg gcgagatcca ggtccaacca agggctctct      240
```

| | |
|---|---|
| acgcaatcac ggacaatcca ccaccctacc gtggacgatc cggtgaccta ttgcggacag | 300 |
| accaatgacc tatcgtgaac cattcaacac ctcgccaagc cgaacctaag gttttgctca | 360 |
| tcatgaggag accatagggc tcattgctat ttgaccctaa taagacttca tcatagaggt | 420 |
| ggaattcaag accatattgc aggtagtgtt a | 451 |

<210> SEQ ID NO 74
<211> LENGTH: 361
<212> TYPE: DNA
<213> ORGANISM: Zea mays

<400> SEQUENCE: 74

| | |
|---|---|
| tcagaggaag ctgctgaaaa aggttaactt tatctctggg gctaagcttc aattcggcat | 60 |
| ctgcccattc ttcagtctta atgtcattgc tgccgagtac aacagtgact caccggtgca | 120 |
| tgcacaccaa ggatgtcatc actaccagca ccatcaacga ctacaatagt gaagagttag | 180 |
| tcttctactc tacacgggag taccacacca accaaaatgg ctcattgttg ccaccaaaca | 240 |
| gaatgtatag cctattatgt ctggcactta gggactcgat agctttaagg gcaagttatg | 300 |
| cactcaagtg actatcatag ggaagggagg ccttccaagg aaagaaggtg cttgttgtcg | 360 |
| g | 361 |

<210> SEQ ID NO 75
<211> LENGTH: 371
<212> TYPE: DNA
<213> ORGANISM: Zea mays

<400> SEQUENCE: 75

| | |
|---|---|
| ggagtgaacc aaatgagctt atgttcctat atgactatta gctagaagtt agagcctaga | 60 |
| tgatggctgc ttctgttggc gtgaaagctc gagtgctcct aaatggtcgt tgtattagct | 120 |
| gatacgacat cgacccgatg caatagataa tattgtttac acgcgcgagt ccaaaattgt | 180 |
| tggctttgag tcggagcagt taacacgaga agtgtatttt atcacttctg agtgcaacct | 240 |
| ttttttttatt attttttccga gcttctgcct cttgcatatg ttgtagattc tcgtcgagaa | 300 |
| gggagtagta gtattacctg atatctatgc taattcaggt ggtgtggtcg ttagctactt | 360 |
| taattgagtg a | 371 |

<210> SEQ ID NO 76
<211> LENGTH: 191
<212> TYPE: DNA
<213> ORGANISM: Zea mays

<400> SEQUENCE: 76

| | |
|---|---|
| catgagcagt gcttttcaac acatgaaggc catgtgcaaa tctttggtgc tgccgaagtg | 60 |
| tgccgtgaca ttggaattgc gggtctagaa aagcaagctc attagatttc tgaaaaaaca | 120 |
| ttaggagtta ttagattggt agcattttttt taagatttaa aattttatag aagtcatcat | 180 |
| tttcgtttat t | 191 |

<210> SEQ ID NO 77
<211> LENGTH: 241
<212> TYPE: DNA
<213> ORGANISM: Zea mays

<400> SEQUENCE: 77

| | |
|---|---|
| tgcaggccgc caagcaaatc acggatgacg atgaactgtg tcttctcctg ccactgtcag | 60 |
| ggcctcagcc ctatgaatgt cagataccctg tatgcggcta tcttcctcct ggcgaacctg | 120 |

```
tctgcgtggt tcgcacgaga gaacaccgta tcatatcacc tgaagcagcg actcagcgga      180
tgtcagggtg accggggttg tctcgcggtt gaaagcgtgc tcgtggcaag ccatgctctt      240
t                                                                      241

<210> SEQ ID NO 78
<211> LENGTH: 431
<212> TYPE: DNA
<213> ORGANISM: Zea mays

<400> SEQUENCE: 78
tctttggaac agatgaccag ctgcacggcg atgaatccca tacgacgacc gtgcatggtg       60
atgaagccga gacgacgacc gtgcatggtg atcaagccga gacgacgacc gtgcatgttg      120
atgaagccga gacgacgacc gtgcatggtg atcaagccga gacgacgact gtgcatggtg      180
atgaatccga gactacgacc gtgcatggtg atgaatccga gacgacgacc gtgcatggtg      240
atgaatcaca gacgacgaac acgcatgtca catcgccgtc ctctttgtat cacacagcgt      300
cgccctcttc gctctactac tcccccgagc atcaccgacc aataacattg accatcaacc      360
tcctccgtcg ccgccgcgtt caccgtcctc ccctcacacc atagaactgc aaatgtccga      420
gataccaaat a                                                           431

<210> SEQ ID NO 79
<211> LENGTH: 471
<212> TYPE: DNA
<213> ORGANISM: Zea mays

<400> SEQUENCE: 79
acttgttgct agaattttcg gaataggctt gctccgacat ctccttgcca agatcttcgg       60
gacaggtgac cgattgcata gtggtgaatc ccagacgacg accacacatc tgatgagatg      120
tacacaacgt cgtcgtcttt ttcatcattc taccgaacaa ctgaggagac gatgaccaca      180
tccgatgaga tgtacacaac accgtcatct ttgtcatcat tgtacctaac acccgaggag      240
acgctgaaca atgatgccat ttcgataagc aactacgaca ctgatgatcc accttcgccg      300
ccacctgtat cgttggtatc tgatgacgta gacatttctg aaccatcacc tccgccatct      360
ccgccgccac atagagtgga tgagatggac aactctgagg catcctttgt cccacaccat      420
atagctccaa atgtttgagg taccaattac ctcaggcaat aatgaggagg a               471

<210> SEQ ID NO 80
<211> LENGTH: 298
<212> TYPE: DNA
<213> ORGANISM: Zea mays

<400> SEQUENCE: 80
cgacaacaag cactttcttg ccttggaagg cctcccttcc ctattgtagt cactcgagtg       60
cataacttgc ccttaaagct atcgattcac taagtgccag acataatagg ctatacattc      120
tctctggtgg caacaattag ccatttggt tggtgtggta ctctattatt gagttttttg       180
gcacgatact tctgtgtaga gtagaagaca aactcttcac cattgtagtc gttgatggtg      240
ctggtggtga tgaaatcctt gctgtgcatg caccggggaa tcactattgt attcggca       298

<210> SEQ ID NO 81
<211> LENGTH: 300
<212> TYPE: DNA
<213> ORGANISM: Zea mays
```

<400> SEQUENCE: 81

```
ggacaacaag caccttcttg ccttgcaagg cctcccttcc ctatggtagc cacttgagtg      60
gatgacttca ccttaaagct atcgattccc taagtgccag acataatagg ctatacattc     120
tctctggtgg caacaatgag tcattttggt tggtgtggta gtctattatt gagtttgttt     180
tggcaccgta ctcccatgga gagtacaaga caaactcttc accgttgtag tcgttgatgg     240
tattggtggt gacgacatcc ttggtgtgca tgcactggtg agtcactgtt gtactcggcg     300
```

<210> SEQ ID NO 82
<211> LENGTH: 300
<212> TYPE: DNA
<213> ORGANISM: Zea mays

<400> SEQUENCE: 82

```
ggacaacaag caccttcttg ccttgcaagg cctcccttcc ctatggtagc cacttgagtg      60
gatgacttca ccttaaagct atcgattccc taagtgccag acataatagg ctatacattc     120
tctctggtgg caacaatgag tcattttggt tggtgtggta gtctattatt gagtttgttt     180
tggcaccgta ctcccatgga gagtagaaga caaactcttc accgttgtag tcgttgatgg     240
tattggtggt gacgacatcc ttggtgtgca tgcactggtg agtcactgtt gtactcggcg     300
```

<210> SEQ ID NO 83
<211> LENGTH: 298
<212> TYPE: DNA
<213> ORGANISM: Zea mays

<400> SEQUENCE: 83

```
cgacaacgag cactttcttg ccttggaagg cctcccttcc ctattgtagt cactctagtg      60
cataacttgc ccttaaagct atcgattcac taagtgccag acataatagg ctatacattc     120
tctctagtgg caacaattag ccatttggt tggtgtggta ctctattatt gagttttttg     180
gcacggtact tccttgtaga gtagaagaca aactcttcac cattgtagtc gttgatgggg     240
ctggtggtga tgaaatcctt ggtgtggatg caccggggaa tcactattgt actcggcg      298
```

<210> SEQ ID NO 84
<211> LENGTH: 297
<212> TYPE: DNA
<213> ORGANISM: Zea mays

<400> SEQUENCE: 84

```
cgacaacgag cactttcttg ccttggaagg cctcccttcc ctattgtagt cactcgagtg      60
cataacttgc ccttaaagct atcgattcac taagtgccag acaaaatagg ctatacattc     120
tctctagtgg caacaattag ccatttggt tggtgtggta ctctattatt gagttttgg      180
cacggtactt ccttgtagag tagaagacaa actcttcacc attgtagtcg ttgatggggc     240
tagtggtgat gaaatccttg gtgtggatgc accggggaat cactattgta ctcggcg       297
```

<210> SEQ ID NO 85
<211> LENGTH: 592
<212> TYPE: DNA
<213> ORGANISM: Zea mays

<400> SEQUENCE: 85

```
gagaccagga ttgttccaac ttcatataga ccatagttag tgacagcatt aaagtttgag      60
atgttgaatg ctaaaaaaca attagtcaca atattgttta gataaaaatt tgagatgtcg     120
gaggaagctg ctgaaaaagg ttaactttat ctatgggact aagcttcaat tcggcatccg     180
```

```
cccattcttc agtcttaatg tcgttgccgc cgagtacaac agtgactcac cagtgcatgc    240
acaccaagga tgtcgtcacc accaatacca tcaacgacta caacggtgaa gagtttgtct    300
tctactctcc atgggagtac ggtgccaaaa caaactcaat aatagactac cacaccaacc    360
aaaatggctc attgttgcca ccagagagaa tgtatagcct attatgtctg gcacttaggg    420
aatcgatagc tttaaggtga agtcatccac tcaagtggct accataggga agggaggcct    480
tgcaaggcaa gaaggtgctt gttgtccgtt gtgataacac cttttcaaca ataatgttca    540
tacctacatt gtttgttcgt cgttgggtaa aaacattgct atatctattt at            592
```

<210> SEQ ID NO 86
<211> LENGTH: 338
<212> TYPE: DNA
<213> ORGANISM: Zea mays

<400> SEQUENCE: 86

```
ggacaacaag caccttcttg ccttgcaagg cctcccttcc ctatggtagc cacttgagtg     60
gatgacttca ccttaaagct attgattccc taagtgccag acataatagg ctatacattc    120
tctctggtgg caacaatgag ccatttttggt tggtgtggta gtctattatt gagttttttt    180
tggcaccgta ctcccatgga gagtagaaga caaactcttc accgttgtag tcgttgatgg    240
tattggtggt gacgacatcc ttggtgtgca tgcactggtg agtcactgtt gtactcggcg    300
gcaacgacat taagactgaa gaatgggcgg atgccgaa                            338
```

<210> SEQ ID NO 87
<211> LENGTH: 300
<212> TYPE: DNA
<213> ORGANISM: Zea mays

<400> SEQUENCE: 87

```
ggacaacaag caccttcttg ccttgcaagg cctcccttcc ctatggtagc cacttgagtg     60
gatgacttca ccttaaagct attgattccc taagtgccag acataatagg ctatacattc    120
tctctggtgg caacaatgag ccatttttggt tggtgtggta gtctattatt gagttttttt    180
tggcaccgta ctcccatgga gagtagaaga caaactcttc accgttgtag tcgttgatgg    240
tattggtggt gacgacatcc ttggtgtgca tgcactggtg agtcactgtt gtactcggcg    300
```

<210> SEQ ID NO 88
<211> LENGTH: 104
<212> TYPE: DNA
<213> ORGANISM: Zea mays

<400> SEQUENCE: 88

```
ggacaacaag caccttcttg ccttgcaagg cctcccttcc ctatggtagc cacttgagtg     60
gatgacttca ccttaaagct atcgattccc taagtgccag acat                     104
```

<210> SEQ ID NO 89
<211> LENGTH: 80
<212> TYPE: DNA
<213> ORGANISM: Zea mays

<400> SEQUENCE: 89

```
ctcttcaccg ttgtagtcgt tgatggtatt ggtggtgacg acatccttgg tgtgcatgca     60
ctggtgagtc actgttgtac                                                 80
```

<210> SEQ ID NO 90

<211> LENGTH: 184
<212> TYPE: DNA
<213> ORGANISM: Artificial Sequence
<220> FEATURE:
<223> OTHER INFORMATION: Synthetic DNA element

<400> SEQUENCE: 90
ggacaacaag caccttcttg ccttgcaagg cctcccttcc ctatggtagc cacttgagtg    60
gatgacttca ccttaaagct atcgattccc taagtgccag acatctcttc accgttgtag   120
tcgttgatgg tattggtggt gacgacatcc ttggtgtgca tgcactggtg agtcactgtt   180
gtac                                                                184

<210> SEQ ID NO 91
<211> LENGTH: 184
<212> TYPE: DNA
<213> ORGANISM: Artificial Sequence
<220> FEATURE:
<223> OTHER INFORMATION: Synthetic DNA element

<400> SEQUENCE: 91
ctcttcaccg ttgtagtcgt tgatggtatt ggtggtgacg acatccttgg tgtgcatgca    60
ctggtgagtc actgttgtac ggacaacaag caccttcttg ccttgcaagg cctcccttcc   120
ctatggtagc cacttgagtg gatgacttca ccttaaagct atcgattccc taagtgccag   180
acat                                                                184

<210> SEQ ID NO 92
<211> LENGTH: 80
<212> TYPE: DNA
<213> ORGANISM: Artificial Sequence
<220> FEATURE:
<223> OTHER INFORMATION: Synthetic DNA element

<400> SEQUENCE: 92
ggacaacaag caccttcttg ccttgcagta ttggtggtga cgacatcctt ggtgtgcatg    60
cactggtgag tcactgttgt                                                80

<210> SEQ ID NO 93
<211> LENGTH: 76
<212> TYPE: DNA
<213> ORGANISM: Artificial Sequence
<220> FEATURE:
<223> OTHER INFORMATION: Synthetic DNA element

<400> SEQUENCE: 93
tacaacagtg actcaccagt gcatgctctg gcacttaggg aatcgatagc tttaccatag    60
ggaagggagg ccttgc                                                    76

<210> SEQ ID NO 94
<211> LENGTH: 81
<212> TYPE: DNA
<213> ORGANISM: Artificial Sequence
<220> FEATURE:
<223> OTHER INFORMATION: Synthetic DNA element

<400> SEQUENCE: 94
ggacaacaag caccttcttg ccttgcatac aacagtgact caccagtgca tgctctggca    60
cttagggaat cgatagcttt a                                              81

<210> SEQ ID NO 95
<211> LENGTH: 1368

<212> TYPE: DNA
<213> ORGANISM: Agrobacterium sp. strain CP4

<400> SEQUENCE: 95

```
atgcttcatg gagcttcatc taggccagct actgccagga agtctagcgg gctcagtggc    60
accgtgcgca tccctggcga taaaagtatt tcacacagga gcttcatgtt cggaggactt   120
gctagtggag agacgagaat cactggtttg cttgagggcg aagatgttat caacaccggt   180
aaggcgatgc aagcaatggg tgccagaatc cgaaaagagg gcgatacgtg gatcatcgac   240
ggtgttggta acggaggatt gctcgctccc gaagcgccac ttgactttgg aacgcagct    300
acggggtgcc gtcttactat gggactggta ggcgtgtatg actttgactc taccttcatc   360
ggtgacgcga gcctcactaa gagaccaatg ggacgagtgc tgaatcccct gagggagatg   420
ggtgtccagg tgaaatctga ggatggtgat cgtcttccgg ttactctgcg aggccccaag   480
accccacgc caatcacgta cagggttccg atggcgtcag cacaggtcaa gtcagcggta   540
ctcctggcgg gcctcaacac acctggaatc acaaccgtga ttgaacccat catgactaga   600
gaccacacgg agaagatgtt gcagggtttc ggcgctaatc taacggtcga accgacgcc   660
gacggcgtga ggacaatccg cttggagggc agaggtaaac tgactggcca agtcatcgat   720
gtgcctggag atccctcgtc cacagcgttt ccccctcgtag ctgcgttgct cgtccctgga   780
tctgatgtga cgatcctgaa tgtcctcatg aatccaacta gaaccggcct catcctcaca   840
ttgcaggaga tgggtgctga catcgaggtt atcaatccta ggttggcagg tggagaggat   900
gtggccgatc tgcgcgtgcg ttctagtaca ctcaaaggcg tgaccgtccc tgaggatcgc   960
gctccatcca tgatcgacga gtaccccatt ctcgccgttg ctgctgcgtt tgccgagggc  1020
gcaactgtaa tgaacggcct tgaggagttg agggttaagg agagtgacag gctgtccgcg  1080
gtggcgaatg gcctgaagct aaacggcgtg gactgcgacg aaggtgaaac gtcccttgta  1140
gtccgtggtc gcccagacgg gaaggggttg gggaatgctt cgggagctgc tgtggcgacg  1200
caccttgatc atagaatcgc catgtcattt ctggtgatgg gacttgtctc cgagaatccg  1260
gtgaccgttg acgatgctac catgatcgcc acctcctttc ctgagttcat ggacctcatg  1320
gcaggcttgg gggccaagat cgagctgtct gatactaagg ccgcttga               1368
```

<210> SEQ ID NO 96
<211> LENGTH: 300
<212> TYPE: DNA
<213> ORGANISM: artificial sequence
<220> FEATURE:
<223> OTHER INFORMATION: Synthetic DNA element

<400> SEQUENCE: 96

```
ggacaacaag caccttcttg ccttgcaagg cctcccttcc ctatggtagc cacttgagtg    60
gatgacttca ccttaaagct atcgattccc taagtgccag acataatagg ctatacattc   120
tctctggtgg caacaatgag tcattttggt tggtgtggta gtctattatt gagtttgttt   180
tggcaccgta ctcccatgga gagtacaaga caaactcttc accgttgtag tcgttgatgg   240
tattggtggt gacgacatcc ttggtgtgca tgcactggtg agtcactgtt gtactcggcg   300
```

<210> SEQ ID NO 97
<211> LENGTH: 104
<212> TYPE: DNA
<213> ORGANISM: Zea mays

<400> SEQUENCE: 97

```
ggacaacaag caccttcttg ccttgcaagg cctcccttcc ctatggtagc cacttgagtg      60
gatgacttca ccttaaagct atcgattccc taagtgccag acat                     104
```

<210> SEQ ID NO 98
<211> LENGTH: 80
<212> TYPE: DNA
<213> ORGANISM: Zea mays

<400> SEQUENCE: 98

```
ctcttcaccg ttgtagtcgt tgatggtatt ggtggtgacg acatccttgg tgtgcatgca      60
ctggtgagtc actgttgtac                                                 80
```

<210> SEQ ID NO 99
<211> LENGTH: 184
<212> TYPE: DNA
<213> ORGANISM: artificial sequence
<220> FEATURE:
<223> OTHER INFORMATION: Synthetic DNA element

<400> SEQUENCE: 99

```
ggacaacaag caccttcttg ccttgcaagg cctcccttcc ctatggtagc cacttgagtg      60
gatgacttca ccttaaagct atcgattccc taagtgccag acatctcttc accgttgtag    120
tcgttgatgg tattggtggt gacgacatcc ttggtgtgca tgcactggtg agtcactgtt    180
gtac                                                                 184
```

<210> SEQ ID NO 100
<211> LENGTH: 184
<212> TYPE: DNA
<213> ORGANISM: artificial sequence
<220> FEATURE:
<223> OTHER INFORMATION: Synthetic DNA element

<400> SEQUENCE: 100

```
ctcttcaccg ttgtagtcgt tgatggtatt ggtggtgacg acatccttgg tgtgcatgca      60
ctggtgagtc actgttgtac ggacaacaag caccttcttg ccttgcaagg cctcccttcc    120
ctatggtagc cacttgagtg gatgacttca ccttaaagct atcgattccc taagtgccag    180
acat                                                                 184
```

<210> SEQ ID NO 101
<211> LENGTH: 80
<212> TYPE: DNA
<213> ORGANISM: artificial sequence
<220> FEATURE:
<223> OTHER INFORMATION: Synthetic DNA element

<400> SEQUENCE: 101

```
ggacaacaag caccttcttg ccttgcagta ttggtggtga cgacatcctt ggtgtgcatg      60
cactggtgag tcactgttgt                                                 80
```

<210> SEQ ID NO 102
<211> LENGTH: 251
<212> TYPE: DNA
<213> ORGANISM: Zea mays

<400> SEQUENCE: 102

```
gaggaaaccg aaaccacatc acatccatac agtggcgaaa gacacagtag ggctaagtat      60
tgcggctttg gtagttgtca tatctaaact tttgatagtc ttatatgtta gagtactcgt    120
tagggttttg attgtctcct gtgtatttac cctctcgcac ttattgtaat gggcctggcc    180
```

```
caactatcga gtgtatcaaa caacgccgcc caacccccact caagggttag ggtttcccac    240
attatatctt c                                                         251
```

<210> SEQ ID NO 103
<211> LENGTH: 121
<212> TYPE: DNA
<213> ORGANISM: Zea mays

<400> SEQUENCE: 103

```
gtagggctaa gtattgcggc tttggtagtt gtcatatcta aactttttgat agtcttatat    60 gttagagtac tcgttagggt tttgattgtc tcctgtgtat ttaccctctc gcacttattg   120
t                                                                   121
```

<210> SEQ ID NO 104
<211> LENGTH: 216
<212> TYPE: DNA
<213> ORGANISM: artificial sequence
<220> FEATURE:
<223> OTHER INFORMATION: Synthetic DNA element

<400> SEQUENCE: 104

```
acacgtggac aacaagcacc ttcttgcctt gcagtattgg tggtgacgac atccttggtg    60
tgcatgcact ggtgagtcac tgttgtgtag ggctaagtat tgcggctttg gtagttgtca   120 tatctaaaact tttgatagtc ttatatgtta gagtactcgt tagggttttg attgtctcct   180
gtgtatttac cctctcgcac ttattgtcct gcagga                             216
```

<210> SEQ ID NO 105
<211> LENGTH: 25
<212> TYPE: DNA
<213> ORGANISM: Zea mays

<400> SEQUENCE: 105

```
accaaagccg caatacttag cccta                                          25
```

<210> SEQ ID NO 106
<211> LENGTH: 24
<212> TYPE: DNA
<213> ORGANISM: Zea mays

<400> SEQUENCE: 106

```
accaaagccg caatacttag ccct                                           24
```

<210> SEQ ID NO 107
<211> LENGTH: 24
<212> TYPE: DNA
<213> ORGANISM: Zea mays

<400> SEQUENCE: 107

```
accaaagccg caatacttag ccct                                           24
```

<210> SEQ ID NO 108
<211> LENGTH: 22
<212> TYPE: DNA
<213> ORGANISM: Zea mays

<400> SEQUENCE: 108

```
caaagccgca atacttagcc ct                                             22
```

<210> SEQ ID NO 109

```
<211> LENGTH: 22
<212> TYPE: DNA
<213> ORGANISM: Zea mays

<400> SEQUENCE: 109
caaagccgca atacttagcc ct                                              22

<210> SEQ ID NO 110
<211> LENGTH: 23
<212> TYPE: DNA
<213> ORGANISM: Zea mays

<400> SEQUENCE: 110
accaaagccg caatacttag ccc                                             23

<210> SEQ ID NO 111
<211> LENGTH: 24
<212> TYPE: DNA
<213> ORGANISM: Zea mays

<400> SEQUENCE: 111
ggctaagtat tgcggctttg gtag                                            24

<210> SEQ ID NO 112
<211> LENGTH: 24
<212> TYPE: DNA
<213> ORGANISM: Zea mays

<400> SEQUENCE: 112
gacaactacc aaagccgcaa tact                                            24

<210> SEQ ID NO 113
<211> LENGTH: 23
<212> TYPE: DNA
<213> ORGANISM: Zea mays

<400> SEQUENCE: 113
gatatgacaa ctaccaaagc cgc                                             23

<210> SEQ ID NO 114
<211> LENGTH: 24
<212> TYPE: DNA
<213> ORGANISM: Zea mays

<400> SEQUENCE: 114
tagatatgac aactaccaaa gccg                                            24

<210> SEQ ID NO 115
<211> LENGTH: 21
<212> TYPE: DNA
<213> ORGANISM: Zea mays

<400> SEQUENCE: 115
gatatgacaa ctaccaaagc c                                               21

<210> SEQ ID NO 116
<211> LENGTH: 24
<212> TYPE: DNA
<213> ORGANISM: Zea mays

<400> SEQUENCE: 116
atcaaaagtt tagatatgac aact                                            24
```

```
<210> SEQ ID NO 117
<211> LENGTH: 24
<212> TYPE: DNA
<213> ORGANISM: Zea mays

<400> SEQUENCE: 117
ttgtcatatc taaacttttg atag                                          24

<210> SEQ ID NO 118
<211> LENGTH: 24
<212> TYPE: DNA
<213> ORGANISM: Zea mays

<400> SEQUENCE: 118
acgagtactc taacatataa gact                                          24

<210> SEQ ID NO 119
<211> LENGTH: 21
<212> TYPE: DNA
<213> ORGANISM: Zea mays

<400> SEQUENCE: 119
agtactctaa catataagac t                                             21

<210> SEQ ID NO 120
<211> LENGTH: 24
<212> TYPE: DNA
<213> ORGANISM: Zea mays

<400> SEQUENCE: 120
gtcttatatg ttagagtact cgtt                                          24

<210> SEQ ID NO 121
<211> LENGTH: 24
<212> TYPE: DNA
<213> ORGANISM: Zea mays

<400> SEQUENCE: 121
tcttatatgt tagagtactc gtta                                          24

<210> SEQ ID NO 122
<211> LENGTH: 24
<212> TYPE: DNA
<213> ORGANISM: Zea mays

<400> SEQUENCE: 122
atcaaaaccc taacgagtac tcta                                          24

<210> SEQ ID NO 123
<211> LENGTH: 24
<212> TYPE: DNA
<213> ORGANISM: Zea mays

<400> SEQUENCE: 123
agacaatcaa aaccctaacg agta                                          24

<210> SEQ ID NO 124
<211> LENGTH: 24
<212> TYPE: DNA
<213> ORGANISM: Zea mays

<400> SEQUENCE: 124
gagacaatca aaaccctaac gagt                                          24
```

```
<210> SEQ ID NO 125
<211> LENGTH: 24
<212> TYPE: DNA
<213> ORGANISM: Zea mays

<400> SEQUENCE: 125
caggagacaa tcaaaaccct aacg                                              24

<210> SEQ ID NO 126
<211> LENGTH: 24
<212> TYPE: DNA
<213> ORGANISM: Zea mays

<400> SEQUENCE: 126
acaggagaca atcaaaaccc taac                                              24

<210> SEQ ID NO 127
<211> LENGTH: 24
<212> TYPE: DNA
<213> ORGANISM: Zea mays

<400> SEQUENCE: 127
cacaggagac aatcaaaacc ctaa                                              24

<210> SEQ ID NO 128
<211> LENGTH: 24
<212> TYPE: DNA
<213> ORGANISM: Zea mays

<400> SEQUENCE: 128
acacaggaga caatcaaaac ccta                                              24

<210> SEQ ID NO 129
<211> LENGTH: 24
<212> TYPE: DNA
<213> ORGANISM: Zea mays

<400> SEQUENCE: 129
acacaggaga caatcaaaac ccta                                              24

<210> SEQ ID NO 130
<211> LENGTH: 23
<212> TYPE: DNA
<213> ORGANISM: Zea mays

<400> SEQUENCE: 130
cacaggagac aatcaaaacc cta                                               23

<210> SEQ ID NO 131
<211> LENGTH: 21
<212> TYPE: DNA
<213> ORGANISM: Zea mays

<400> SEQUENCE: 131
caggagacaa tcaaaaccct a                                                 21

<210> SEQ ID NO 132
<211> LENGTH: 23
<212> TYPE: DNA
<213> ORGANISM: Zea mays

<400> SEQUENCE: 132
acacaggaga caatcaaaac cct                                               23
```

<210> SEQ ID NO 133
<211> LENGTH: 24
<212> TYPE: DNA
<213> ORGANISM: Zea mays

<400> SEQUENCE: 133
gggttttgat tgtctcctgt gtat                                             24

<210> SEQ ID NO 134
<211> LENGTH: 22
<212> TYPE: DNA
<213> ORGANISM: Zea mays

<400> SEQUENCE: 134
acacaggaga caatcaaaac cc                                               22

<210> SEQ ID NO 135
<211> LENGTH: 24
<212> TYPE: DNA
<213> ORGANISM: Zea mays

<400> SEQUENCE: 135
aatacacagg agacaatcaa aacc                                             24

<210> SEQ ID NO 136
<211> LENGTH: 18
<212> TYPE: DNA
<213> ORGANISM: Zea mays

<400> SEQUENCE: 136
tgattgtctc ctgtgtat                                                    18

<210> SEQ ID NO 137
<211> LENGTH: 24
<212> TYPE: DNA
<213> ORGANISM: Zea mays

<400> SEQUENCE: 137
gattgtctcc tgtgtattta ccct                                             24

<210> SEQ ID NO 138
<211> LENGTH: 24
<212> TYPE: DNA
<213> ORGANISM: Zea mays

<400> SEQUENCE: 138
gagagggtaa atacacagga gaca                                             24

<210> SEQ ID NO 139
<211> LENGTH: 24
<212> TYPE: DNA
<213> ORGANISM: Zea mays

<400> SEQUENCE: 139
tctcctgtgt atttaccctc tcgc                                             24

<210> SEQ ID NO 140
<211> LENGTH: 23
<212> TYPE: DNA
<213> ORGANISM: Zea mays

<400> SEQUENCE: 140

```
<210> SEQ ID NO 141
<211> LENGTH: 23
<212> TYPE: DNA
<213> ORGANISM: Zea mays

<400> SEQUENCE: 141
cgagagggta aatacacagg aga                                          23

<210> SEQ ID NO 142
<211> LENGTH: 23
<212> TYPE: DNA
<213> ORGANISM: Zea mays

<400> SEQUENCE: 142
tctcctgtgt atttaccctc tcg                                          23

<210> SEQ ID NO 143
<211> LENGTH: 24
<212> TYPE: DNA
<213> ORGANISM: Zea mays

<400> SEQUENCE: 143
ctcctgtgta tttaccctct cgca                                         24

<210> SEQ ID NO 144
<211> LENGTH: 21
<212> TYPE: DNA
<213> ORGANISM: Zea mays

<400> SEQUENCE: 144
cgagagggta aatacacagg a                                            21

<210> SEQ ID NO 145
<211> LENGTH: 24
<212> TYPE: DNA
<213> ORGANISM: Zea mays

<400> SEQUENCE: 145
tacaataagt gcgagagggt aaat                                         24

<210> SEQ ID NO 146
<211> LENGTH: 24
<212> TYPE: DNA
<213> ORGANISM: Zea mays

<400> SEQUENCE: 146
tacaataagt gcgagagggt aaat                                         24

<210> SEQ ID NO 147
<211> LENGTH: 23
<212> TYPE: DNA
<213> ORGANISM: Zea mays

<400> SEQUENCE: 147
acaataagtg cgagagggta aat                                          23

<210> SEQ ID NO 148
<211> LENGTH: 23
<212> TYPE: DNA
<213> ORGANISM: Zea mays

<400> SEQUENCE: 148
```

```
tacaataagt gcgagagggt aaa                                              23

<210> SEQ ID NO 149
<211> LENGTH: 22
<212> TYPE: DNA
<213> ORGANISM: Zea mays

<400> SEQUENCE: 149
acaataagtg cgagagggta aa                                               22

<210> SEQ ID NO 150
<211> LENGTH: 21
<212> TYPE: RNA
<213> ORGANISM: artificial sequence
<220> FEATURE:
<223> OTHER INFORMATION: Synthetic RNA element

<400> SEQUENCE: 150
acagugacuc accagugcau g                                                21

<210> SEQ ID NO 151
<211> LENGTH: 24
<212> TYPE: RNA
<213> ORGANISM: artificial sequence
<220> FEATURE:
<223> OTHER INFORMATION: Synthetic RNA element

<400> SEQUENCE: 151
caaggcaaga aggugcuugu uguc                                             24

<210> SEQ ID NO 152
<211> LENGTH: 21
<212> TYPE: DNA
<213> ORGANISM: Artificial Sequence
<220> FEATURE:
<223> OTHER INFORMATION: synthetic DNA element

<400> SEQUENCE: 152
catgcactgg tgagtcactg t                                                21

<210> SEQ ID NO 153
<211> LENGTH: 21
<212> TYPE: DNA
<213> ORGANISM: Artificial Sequence
<220> FEATURE:
<223> OTHER INFORMATION: synthetic DNA element

<400> SEQUENCE: 153
acagtgactc accagtgcat g                                                21

<210> SEQ ID NO 154
<211> LENGTH: 24
<212> TYPE: DNA
<213> ORGANISM: Artificial Sequence
<220> FEATURE:
<223> OTHER INFORMATION: synthetic DNA element

<400> SEQUENCE: 154
aagctattga ttccctaagt gcca                                             24
```

US 11,560,574 B2

METHODS AND COMPOSITIONS FOR SELECTIVE REGULATION OF PROTEIN EXPRESSION

CROSS REFERENCE TO RELATED APPLICATIONS

This application is a continuation of U.S. application Ser. No. 15/726,363, filed Oct. 5, 2017 (pending), which application is a divisional of U.S. application Ser. No. 14/720,052, filed May 22, 2015, now U.S. Pat. No. 9,816,106, which application is a continuation of U.S. application Ser. No. 13/538,670, filed Jun. 29, 2012, now U.S. Pat. No. 9,139,838 which application claims the benefit of priority of U.S. Provisional Patent Application 61/504,102, which was filed on Jul. 1, 2011, each of which is incorporated herein by reference in its entirety.

INCORPORATION OF SEQUENCE LISTING

The sequence listing contained in the file named "MONS294US.txt", which is 40.5 kilobytes (size as measured in Microsoft Windows®) and was created on Jun. 15, 2012, is filed herewith by electronic submission and is incorporated by reference herein.

FIELD OF THE INVENTION

The invention relates generally to the fields of agriculture, plant breeding, and molecular biology. More specifically, the invention relates to methods and compositions for selectively suppressing recombinant protein expression in the male reproductive tissue of transgenic plants and uses thereof.

BACKGROUND OF THE INVENTION

Hybrid seed, that is, seed produced by hybridization or cross-fertilization of closely related plants, can be grown into progeny hybrid plants possessing a desirable combination of traits not possessed by either parent plant. Hybrid plants can display superior agronomic characteristics, including improvement of plant size, yield, nutritional composition, disease resistance, herbicide tolerance, stress tolerance, climatic adaptation, and other desirable traits. Efficient hybrid seed production requires that a plant's own pollen not be permitted to self-fertilize the plant.

In hybrid seed production, pollen production and/or shed may be prevented in a female parent plant in order to facilitate cross-pollination of the female rather than self-pollination. Such prevention may be achieved by, for example, manual removal of the pollen-containing structures (e.g., manual or mechanical detasseling in corn), use of a genetic means of pollination control (e.g., cytoplasmic male sterile, nuclear male sterile), and/or use of a chemical agent.

SUMMARY OF THE INVENTION

The invention relates generally to methods of selectively suppressing recombinant protein expression in the male reproductive tissue of transgenic plants, recombinant DNA constructs useful in such methods, as well as transgenic plants, cells, and seeds containing such recombinant DNA constructs. The recombinant DNA constructs and the transgenic plants, cells, and seeds containing such constructs provide a greatly improved way to use herbicides for inducing male sterility in transgenic plants for the production of hybrid seed.

In one aspect, the invention provides a recombinant DNA construct that includes a protein-coding sequence encoding a recombinant protein and a male tissue-specific siRNA (mts-siRNA) element operably linked to the protein-coding sequence. In one embodiment, the mts-siRNA element is included within the 3' untranslated region of the protein-coding sequence. In another embodiment, the mts-siRNA element is located between the protein-coding sequence and a polyadenylation sequence which is part of a 3' untranslated region. In another embodiment, the mts-siRNA element includes at least one mts-siRNA sequence. In another embodiment, the mts-siRNA element includes at least one mts-siRNA sequence selected from the group consisting of SEQ ID NO: 1-56 and 105-149. In another embodiment, the mts-siRNA element is selected from the group consisting of SEQ ID NO: 57-94 and 96-104. In another embodiment, the expression of the recombinant protein in a transgenic plant confers at least vegetative herbicide tolerance to the plant. In another embodiment, the recombinant protein is a glyphosate-tolerant EPSPS.

Another aspect of the invention provides a method of making a recombinant DNA construct including identifying an mts-siRNA element including at least one mts-siRNA sequence and operably linking the mts-siRNA element to a protein-coding sequence, for instance a DNA sequence encoding a recombinant protein. In one embodiment, the mts-siRNA element includes at least one mts-siRNA sequence selected from the group consisting of SEQ ID NO: 1-56 and 105-149 or is at least one mts-siRNA element selected from the group consisting of SEQ ID NO: 57-94 and 96-104. In another embodiment, the mts-siRNA element is tassel-specific.

In a further aspect, the invention provides a transgenic plant including a recombinant DNA construct of the invention, as well as a seed, cell, or part of the transgenic plant. In one embodiment, the plant is a monocotyledonous plant. In another embodiment, the plant is a maize (*Zea mays*) plant.

In a further aspect, the invention also provides a method of selectively suppressing the expression of a recombinant protein in a male reproductive tissue of a transgenic plant by expressing in the transgenic plant a recombinant DNA construct that includes a protein-coding sequence operably linked to a DNA sequence including an mts-siRNA element. In one embodiment, the mts-siRNA element includes at least one mts-siRNA sequence. In another embodiment, the male reproductive tissue is a tassel of a maize plant. In another embodiment, the mts-siRNA element includes at least one mts-siRNA sequence selected from the group consisting of SEQ ID NO: 1-56 and 105-149. In another embodiment, the mts-siRNA element is at least one element selected from the group consisting of SEQ ID NO: 57-94 and 96-104. In another embodiment, the expression of the recombinant protein in a transgenic plant confers at least vegetative herbicide tolerance to the plant. In another embodiment, the recombinant protein is a glyphosate-tolerant EPSPS.

The invention also provides a method of inducing male sterility in a transgenic plant, including the step of applying herbicide to a transgenic plant that has in its genome a recombinant DNA construct comprising a protein-coding sequence operably linked to a DNA sequence including an mts-siRNA element that confers at least vegetative herbicide tolerance to the transgenic plant, wherein the herbicide is applied during the development of the male reproductive tissue of the transgenic plant thereby inducing male-sterility in the transgenic plant. In one embodiment, the transgenic plant is a maize plant. In another embodiment, the herbicide application prevents at least pollen shed or anther extrusion in the treated transgenic plant. In another embodiment, the development stage of the male reproductive tissue during which herbicide is applied is a stage selected from the group consisting of the V4, V5, V6, V7, V8, V9, V10, V11, V12, V13, and V14 stage of maize plant development. In another embodiment, the herbicide is selected from the group consisting of acetyl coenzyme A carboxylase (ACCase) inhibitors, acetolactate synthase (ALS) inhibitors, photosystem II (PSII) inhibitors, protoporphyrinogen oxidase (PPO) inhibitors, 4-hydroxyphenyl dioxygenase (HPPD) inhibitors, 5-enolypyruvyl shikimate 3-phosphate synthase (EPSPS) inhibitors, glutamine synthetase (GS) inhibitors, and synthetic auxins. In another embodiment, the herbicide is glyphosate and the recombinant protein is a glyphosate-tolerant EPSPS.

The invention also provides a method of producing hybrid seed including applying an effective amount of an herbicide to a transgenic plant including in its genome a recombinant DNA construct comprising a protein-coding sequence operably linked to a DNA sequence including an mts-siRNA element, wherein the herbicide is applied during the development of the male reproductive tissue of the transgenic plant thereby inducing male sterility in the transgenic plant; fertilizing the transgenic plant with pollen from a second plant; and harvesting hybrid seed from the transgenic plant. In one embodiment, the transgenic plant is maize. An effective amount of an herbicide is a dose of herbicide sufficient to render a transgenic plant comprising a recombinant DNA construct of the invention male sterile (an effective dose). In another embodiment, the herbicide is glyphosate and the recombinant protein is a glyphosate-tolerant EPSPS. In another embodiment, the glyphosate is applied during the development at an effective dose of about 0.125 pounds acid equivalent per acre to about 8 pounds acid equivalent per acre. Other specific embodiments of the invention are disclosed in the following detailed description. Throughout this specification and the claims, unless the context requires otherwise, the word "comprise" and its variations, such as "comprises" and "comprising", will be understood to imply the inclusion of a stated integer, element, or step or group of integers, elements, or steps, but not the exclusion of any other integer, element, or step or group of integers, elements, or steps.

BRIEF DESCRIPTION OF THE DRAWINGS

FIG. 7 depicts transgenic maize plants generated from constructs containing a CP4-EPSPS/mts-siRNA element expression cassette, which were vegetatively tolerant to glyphosate and had induced male-sterility with late application of glyphosate, as described in Example 7.

FIG. 8 depicts data for one year of field trials measuring Male Fertility Rating (MFR) following late glyphosate spray.

FIG. 9 depicts field trial results measuring the number of plants per plot with male-sterility measured by anther extrusion through S90, at S90+3, and at S90+6 under two different glyphosate spray treatment regimens (Trt 2 and Trt 3) for NK603 (CP4-EPSPS transgenic maize), MON87427 (CP4-EPSPS transgenic maize with glyphosate-inducible male-sterility), and four events from construct 3, as described in Example 5.

FIG. 10 depicts results of pollen viability studies as described in Example 5. FIGS. 10A and 10B show an example of late breaking anther extrusion in tassel from a sterility sprayed construct 3 event. The box in FIG. 10A is the portion magnified in FIG. 10B. An example of late breaking anther extrusion is circled in FIG. 10B. Alexander staining of pollen from sterility-sprayed, late breaking extruded anther of sprayed construct 3 events shows only non-viable pollen (translucent light blue, irregular shape pollen grains) (FIG. 10C). Pollen from non-sprayed construct 3 anthers was fully viable and appears opaque, dark purple and spherical with Alexander stain (FIG. 10D).

FIG. 13 depicts pollen grain analysis from F1 hybrid plants, as described in Example 7. The panels show Alexander staining results of pollen from three different F1 hybrid crosses: non-transgenic female x MON88017 male; MON87427 female x MON88017 male; and construct 3 event female x MON88017 male. Tassel fertility was functionally restored in F1 hybrids produced from construct 3 event plants using MON88017 pollen.

FIG. 14 depicts schematic drawings of embodiments of recombinant DNA constructs (shown in 5' to 3' direction from left to right) including (top) a protein-coding sequence (e.g., DNA encoding a glyphosate-resistant EPSPS) operably linked to a DNA sequence comprising an mts-siRNA element (e.g., one or more selected from the group consisting of SEQ ID NO: 57-94 and 96-104) (top). In a non-limiting specific embodiment (bottom) the recombinant DNA construct includes a promoter operably linked to, in order, an intron, a transit peptide, CP4-EPSPS encoded by SEQ ID NO: 95, an mts-siRNA element (SEQ ID NO: 81), and a 3'UTR.

DETAILED DESCRIPTION OF THE INVENTION

Recombinant DNA Constructs

Figure 1:
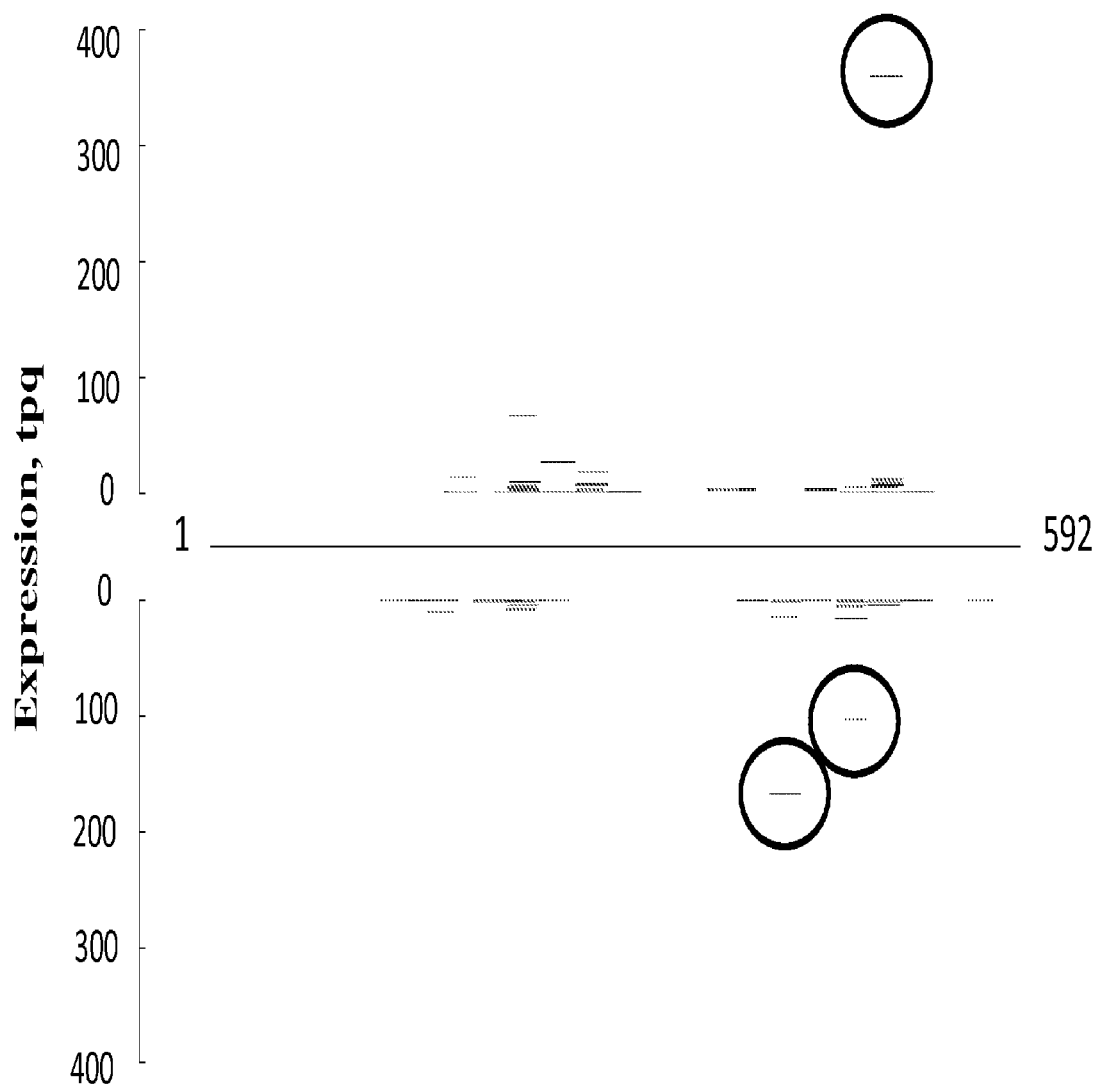
FIG. 1 depicts mapping of mts-siRNA sequences on an mts-siRNA element (SEQ ID NO: 85), as described in Example 1. The X-axis from left to right represents the orientation of the mts-siRNA element with the top strand represented in the top half of the chart and the bottom strand represented in the bottom half of the chart; the nucleotide position from 5' to 3' orientation is shown from left to right on the top and from right to left on the bottom. The mts-siRNA sequences are shown in their relative alignment positions. The Y-axis represents the relative abundance of the mts-siRNA expressed in tassel tissue as transcripts per quarter million sequences (tpq). The mts-siRNA that were highly represented in the library are circled.

The invention provides compositions and methods for selectively suppressing recombinant protein expression in a male reproductive tissue of a transgenic plant and uses thereof. In one aspect, the invention provides a recombinant DNA construct that includes a protein-coding sequence operably linked to a DNA sequence including an mts-siRNA element, i.e. a chimeric transgene including a protein-coding sequence encoding the recombinant protein and at least one mts-siRNA element operably linked to the protein-coding sequence. In one embodiment, such recombinant DNA constructs are useful for selectively suppressing the expression of a recombinant protein in a male reproductive tissue of a transgenic plant. In one aspect, the invention provides a recombinant DNA molecule comprising the recombinant DNA construct and methods of use thereof. Nucleic acid sequences can be provided as DNA or as RNA, as specified; disclosure of one necessarily defines the other, as is known to one of ordinary skill in the art. Furthermore, disclosure of a given nucleic acid sequence necessarily defines the exact complement of that sequence, as is known to one of ordinary skill in the art.

A "male tissue-specific siRNA" or "mts-siRNA" is a small RNA (sRNA) of about 18 to about 26 nucleotides (e.g., 18, 19, 20, 21, 22, 23, 24, 25 or 26 nucleotides) enriched or specifically expressed in the male reproductive tissue(s) (e.g., male inflorescence) of a plant, i.e., having an male tissue-specific expression pattern. Male tissue-specific siRNA are naturally occurring in plants and can be detected using techniques known in the art, such as low molecular weight northern analysis. A DNA sequence that is complementary to an mts-siRNA is referred to herein as an "mts-siRNA sequence". Examples of mts-siRNA sequences for endogenous plant mts-siRNA are provided as SEQ ID NO: 1-56 and 105-149. In an embodiment, an mts-siRNA sequence is the exact DNA complement (with no mismatches) to a given mts-siRNA. In other embodiments, an mts-siRNA sequence varies by 1-3 nucleotide mismatches compared to a given mts-siRNA and nonetheless has sufficient complementarity to bind or hybridize, e.g., under typical physiological conditions, to that mts-siRNA. "Complementarity" refers to the capability of nucleotides on one polynucleotide strand to base-pair with nucleotides on another polynucleotide strand according to the standard Watson-Crick complementarity rules (i e., guanine pairs with cytosine (G:C) and adenine pairs with either thymine (A:T) or uracil (A:U); it is possible for intra-strand hybridization to occur between two or more complementary regions of a single polynucleotide. When included in a recombinant DNA construct as described herein, an mts-siRNA is capable of RNAi-mediated suppression or disruption of the expression of a gene and/or protein.

At least one, at least two, at least three, or more than three mts-siRNA sequences can be clustered together or even overlap within a single DNA molecule. Such a DNA molecule is referred to herein as a "male tissue-specific siRNA element" or "mts-siRNA element" and is defined as including at least one, at least two, at least three, or more than three mts-siRNA sequences within an about 500 nucleotide sequence window. An mts-siRNA element can be any length, such as about 20 nucleotides (nt), about 25 nt, about 30 nt, about 40 nt, about 50 nt, about 60 nt, about 70 nt, about 80 nt, about 100 nt, about 150 nt, about 200 nt, about 250 nt, about 300 nt, about 350 nt, about 400 nt, about 450 nt, about 500 nt, about 550 nt, or about 600 nt.

A recombinant DNA construct of the invention is a DNA molecule including at least a protein-coding sequence operably linked to a DNA sequence including an mts-siRNA element. The term "recombinant" refers to a molecule or a cell or organism that man-made through genetic engineering and as such is the product of human activity and would not otherwise normally occur in nature. As used herein, a recombinant DNA construct is a recombinant DNA molecule including two or more heterologous DNA sequences. The term "heterologous" refers to the relationship between two or more nucleic acid or protein sequences that are derived from different sources (e.g., from different locations in a genome, or from different species). In one example, a promoter and a protein-coding DNA sequence are heterologous with respect to each other if the promoter is not the native promoter of the protein-coding DNA sequence. In another example, a protein-coding sequence is heterologous with respect to an mts-siRNA element if such a combination is not normally found in nature, such as a plant mts-siRNA element operably linked to a gene for herbicide tolerance, such as CP4-EPSPS. In addition, a particular sequence can be "heterologous" with respect to a cell or organism into which it is introduced (i.e., a sequence that does not naturally occur in that particular cell or organism).

The term "operably linked" refers to two polynucleotide molecules linked in manner so that one can affect the expression of the other. For example, a first polynucleotide molecule is operably linked with a second polynucleotide molecule where the polynucleotide molecules are so arranged that the first polynucleotide molecule can affect the expression of the second polynucleotide molecule. The two polynucleotide molecules can be part of a single contiguous polynucleotide molecule and can be adjacent or separated. For example, an mts-siRNA element is operably linked to a protein-coding sequence if, after transcription in male reproductive tissue cell, the presence of the mts-siRNA element results in the suppression of recombinant protein expression in the cell. Operable linkage of the protein-coding sequence and the mts-siRNA element can be achieved, for example, through incorporation of an mts-siRNA element adjacent to the protein-coding sequence (such as located 5' or 3' to the protein-coding sequence, but not necessarily in contiguous linkage), in or adjacent to an untranslated region (UTR) of the recombinant DNA construct (such as located in or next to the 5' UTR or the 3' UTR), and/or after the protein-coding sequence and before the polyadenylation signal. In one embodiment, one or more mts-siRNA elements are located between the protein-coding sequence and the polyadenylation sequence, i.e., 3' to and adjacent to the protein-coding sequence. In another embodiment, one or more mts-siRNA elements are located between the stop codon of the protein-coding sequence and the polyadenylation sequence. In another embodiment, one or more mts-siRNA elements are located within the 3' UTR sequence adjacent to the protein-coding sequence.

The DNA sequence of the mts-siRNA element can be varied by using different combinations and locations of individual mts-siRNA sequences and/or by incorporating 1-3 nucleotide mismatches in an mts-siRNA element (relative to a given mts-siRNA sequence). Examples of mts-siRNA elements are provided herein as SEQ ID NO: 57-94 and 96-104 and in the working Examples. An mts-siRNA element can function in either direction, i.e., it is non-directional, and as such can be used in either the 5' to 3' orientation or in the 3' to 5' orientation in a recombinant DNA construct.

Mts-siRNA elements, mts-siRNA sequences, and mts-siRNAs can be identified by methods known to those skilled in the art, for example through bioinformatic analysis of plant sRNA and cDNA libraries. An example of such an identification method is provided in the Examples below. In particular, mts-siRNA and mts-siRNA sequences can be identified from sRNA libraries. The identified mts-siRNA sequences can be compared to cDNA and/or genomic sequence collections to identify mts-siRNA elements (i.e., regions of DNA including at least one, at least two, at least three, or more than three mts-siRNA sequences within a 500 nucleotide sequence window), which are useful for developing recombinant DNA constructs as described herein.

In some embodiments, these mts-siRNA elements are synthesized or modified in vitro to contain more, fewer, or different mts-siRNA sequences and/or to rearrange the relative position of one or more mts-siRNA sequence(s), where such a modification is beneficial in increasing or decreasing the effect of the mts-siRNA element. Methods for synthesizing or for in vitro modification of an mts-siRNA element and determining the optimal variation for the desired level of suppression are known by those of skill in the art. Chimeric mts-siRNA elements can also be designed using methods known to those of skill in the art, such as by inserting additional desired mts-siRNA sequences internally in an mts-siRNA element or by linking additional mts-siRNA sequences 5' or 3' to an mts-siRNA element. Non-limiting embodiments of a chimeric mts-siRNA element include mts-siRNA elements having about 80 nt, about 100 nt, about 150 nt, about 200 nt, about 250 nt, or about 300 nt of SEQ ID NO: 86; about 80 nt, about 100 nt, about 150 nt, about 200 nt, about 250 nt, or about 300 nt of SEQ ID NO: 87; and/or about 80 nt, about 100 nt, about 150 nt, about 200 nt, about 250 nt, about 300 nt, about 350 nt, about 400 nt, about 450 nt, about 500 nt, or about 550 nt of SEQ ID NO: 85. Additional embodiments are provided in the working Examples.

The recombinant DNA construct can be used to selectively suppress expression of the recombinant protein in male reproductive tissues of a transgenic plant expressing the construct, i.e., resulting in expression in at least vegetative tissues but not in male reproductive tissues. As used herein, "expression of a recombinant protein" refers to the production of a recombinant protein from a protein-coding sequence and the resulting transcript (mRNA) in a cell. As used herein the term "suppressing" means reducing; for example, suppressing the expression of a recombinant protein means reducing the level of recombinant protein produced in a cell, e.g., through RNAi-mediated post-transcriptional gene suppression.

Selective suppression of recombinant protein as used herein refers to a reduction of recombinant protein production in a cell or tissue as compared to a reference cell or tissue by at least about 75%, at least about 80%, at least about 85%, at least about 90%, at least about 95%, or at least about 99%. A reference cell or tissue can be, e.g., a vegetative cell or tissue from the same or a similar transgenic plant expressing the recombinant protein, or e.g., a vegetative cell or tissue from a transgenic plant having a similar transgene for expressing the recombinant protein but lacking the mts-siRNA element. Suppression of protein expression can be determined using any technique known to one skilled in the art, such as by directly measuring protein accumulation in a cell or tissue sample using a technique such as ELISA or western blot analysis, by measuring enzymatic activity of the protein, or by phenotypically determining protein expression. In one embodiment, selective suppression of recombinant protein refers to sufficient reduction in expression of a recombinant protein capable of conferring herbicide tolerance in the male tissue of a transgenic plant, resulting in a detectable phenotype of altered male fertility in a transgenic plant to which herbicide was applied as a sterility spray. The detection of altered male fertility in such a transgenic plant would therefore indicate the selective suppression of the recombinant protein.

As used herein, the term "protein-coding sequence" refers to a polynucleotide molecule having a nucleotide sequence that encodes a polypeptide or protein sequence. i.e., a polynucleotide sequence encoding a recombinant protein. Depending upon conditions, the nucleotide sequence may or may not be actually translated into a polypeptide molecule in a cell. The boundaries of a protein-coding sequence are commonly delineated by a translation start codon at the 5'-terminus and a translation stop codon at the 3'-terminus. A protein-coding sequence of the invention includes, but is not limited to, a protein-coding sequence that provides a desirable characteristic associated with plant morphology, physiology, growth and development, yield, nutritional enhancement, disease or pest resistance, herbicide tolerance, or environmental or chemical tolerance. In one embodiment, a protein-coding sequence of the invention encodes a recombinant protein that when expressed in a transgenic plant confers herbicide tolerance at least in a cell and/or tissue where the expressed protein occurs; selective suppression of the herbicide tolerance protein in male reproductive tissue of the transgenic plant in conjunction with timely application of the herbicide results in at least reduced male fertility or in male sterility. Such inducible male-sterility combined with vegetative herbicide tolerance can be used to increase the efficiency with which hybrid seed is produced, for example by eliminating or reducing the need to physically emasculate the maize plant used as a female in a given cross during hybrid seed production. Herbicide-inducible male-sterility systems have been described, for instance in U.S. Pat. No. 6,762,344 and U.S. Patent Publication 2011/0126310. Examples of herbicides useful in practicing the invention include, but are not limited to, acetyl coenzyme A carboxylase (ACCase) inhibitors (e.g., fops and dims), acetolactate synthase (ALS) inhibitors (e.g., sulfonylureas (SUs) and imidazolinones (IMIs)), photosystem II (PSII) inhibitors (e.g., traiazines and phenyl ethers), protoporphyrinogen oxidase (PPO) inhibitors (e.g., flumioxazsin and fomesafen), 4-hydroxyphenyl pyruvate dioxygenase (HPPD) inhibitors (e.g., isoxaflutole and triketones such as mesotrione), 5-enolpyruvyl shikimate 3-phosphate synthase (EPSPS) inhibitors (e.g., glyphosate), glutamine synthetase (GS) inhibitors (e.g., glufosinate and phosphinothricin), synthetic auxins (e.g., 2,4-D and dicamba). Examples of protein-coding sequences and/or recombinant proteins for use in practicing the invention include but are not limited to genes encoding recombinant proteins conferring tolerance to HPPD inhibitors (such as herbicide-insensitive HPPD), genes encoding recombinant proteins conferring tolerance to glufosinate (such as pat and bar), genes encoding recombinant proteins conferring tolerance to glyphosate (such as the glyphosate-tolerant EPSPS known as CP4-EPSPS, provided herein as SEQ ID NO: 95), and genes encoding recombinant proteins conferring tolerance to dicamba (such as dicamba monooxygenase (DMO)).

Recombinant DNA constructs of the invention are made by techniques known in the art and in various embodiments are included in plant transformation vectors, plasmids, or plastid DNA. Such recombinant DNA constructs are useful for producing transgenic plants and/or cells and as such can be also contained in the genomic DNA of a transgenic plant, seed, cell, or plant part. This invention therefore includes embodiments wherein the recombinant DNA construct is located within a plant transformation vector, or on a biolistic particle for transforming a plant cell, or within a chromosome or plastid of a transgenic plant cell, or within a transgenic cell, transgenic plant tissue, transgenic plant seed, transgenic pollen grain, or a transgenic or partially transgenic (e.g., a grafted) plant. A vector is any DNA molecule that may be used for the purpose of plant transformation, i.e., the introduction of DNA into a cell. Recombinant DNA constructs of the invention can, for example, be inserted into a plant transformation vector and used for plant transformation to produce transgenic plants, seeds, and cells. Methods for constructing plant transformation vectors are well known in the art. Plant transformation vectors of the invention generally include, but are not limited to: a suitable promoter for the expression of an operably linked DNA, an operably linked recombinant DNA construct, and a polyadenylation signal (which may be included in a 3'UTR sequence). Promoters useful in practicing the invention include those that function in a plant for expression of an operably linked polynucleotide. Such promoters are varied and well known in the art and include those that are inducible, viral, synthetic, constitutive, temporally regulated, spatially regulated, and/or spatio-temporally regulated. Additional optional components include, but are not limited to, one or more of the following elements: 5' UTR, enhancer, cis-acting element, intron, signal sequence, transit peptide sequence, and one or more selectable marker genes. In one embodiment, a plant transformation vector comprises a recombinant DNA construct.

The recombinant DNA constructs and plant transformation vectors of this invention are made by any method suitable to the intended application, taking into account, for example, the type of expression desired, the protein-coding sequence (and thus herbicide tolerance) desired, and convenience of use in the plant in which the recombinant DNA construct is to be expressed. General methods useful for manipulating DNA molecules for making and using recombinant DNA constructs and plant transformation vectors are well known in the art and described in detail in, for example, handbooks and laboratory manuals including Sambrook and Russell, "Molecular Cloning: A Laboratory Manual" (third edition), Cold Spring Harbor Laboratory Press, NY, 2001. The recombinant DNA constructs of the invention can be modified by methods known in the art, either completely or in part, e.g., for increased convenience of DNA manipulation (such as restriction enzyme recognition sites or recombination-based cloning sites), or for including plant-preferred sequences (such as plant-codon usage or Kozak consensus sequences), or to include sequences useful for recombinant DNA construct design (such as spacer or linker sequences). In certain embodiments, the DNA sequence of the recombinant DNA construct includes a DNA sequence that has been codon-optimized for the plant in which the recombinant DNA construct is to be expressed. For example, a recombinant DNA construct to be expressed in a plant can have all or parts of its sequence codon-optimized for expression in a plant by methods known in the art. The recombinant DNA constructs of the invention can be stacked with other recombinant DNA for imparting additional traits (e.g., in the case of transformed plants, traits including herbicide resistance, pest resistance, cold germination tolerance, water deficit tolerance) for example, by expressing or suppressing other genes.

Transgenic Plant Cells and Transgenic Plants

An aspect of the invention includes transgenic plant cells, transgenic plant tissues, and transgenic plants or seeds which include a recombinant DNA construct of the invention. A further aspect of the invention includes artificial or recombinant plant chromosomes which include a recombinant DNA construct of the invention. Suitable methods for transformation of host plant cells for use with the current invention include virtually any method by which DNA can be introduced into a cell (e.g., where a recombinant DNA construct is stably integrated into a plant chromosome) and are well known in the art. An exemplary and widely utilized method for introducing a recombinant DNA construct into plants is the *Agrobacterium* transformation system, which is well known to those of skill in the art. Transgenic plants can be regenerated from a transformed plant cell by the methods of plant cell culture. A transgenic plant homozygous with respect to a transgene can be obtained by sexually mating (selfing) an independent segregant transgenic plant that contains a single exogenous gene sequence to itself, for example an F0 plant, to produce F1 seed. One fourth of the F1 seed produced will be homozygous with respect to the transgene. Plants grown from germinating F1 seed can be tested for heterozygosity, typically using a SNP assay or a thermal amplification assay that allows for the distinction between heterozygotes and homozygotes (i.e., a zygosity assay).

The invention provides a transgenic plant having in its genome a recombinant DNA construct of the invention, including, without limitation, alfalfa, cotton, maize, canola, rice, soybean, and wheat, among others. The invention also provides transgenic plant cells, plant parts, and progeny of such a transgenic plant. As used herein "progeny" includes any plant, seed, plant cell, and/or plant part produced from or regenerated from a plant, seed, plant cell, and/or plant part that included a recombinant DNA construct of the invention. Transgenic plants, cells, parts, and seeds produced from such plants can be homozygous or heterozygous for the recombinant DNA construct of the invention.

Further included in this invention are embodiments wherein the recombinant DNA construct is in a commodity product produced from a transgenic plant, seed, or plant part of this invention; such commodity products include, but are not limited to harvested parts of a plant, crushed or whole grains or seeds of a plant, or any food or non-food product comprising the recombinant DNA construct of this invention.

Methods of Inducing Male-Sterility in Transgenic Plants and of Producing Hybrid Seed Another aspect of the invention includes a method of inducing male-sterility in a transgenic plant including applying an effective amount of an herbicide to a transgenic plant including a recombinant DNA construct that includes a protein-coding sequence encoding a recombinant protein that confers herbicide tolerance to the transgenic plant operably linked to a DNA sequence including an mts-siRNA element that confers at least vegetative herbicide tolerance to the transgenic plant, wherein the herbicide application is carried out during the development of the male reproductive tissue of the transgenic plant thereby inducing male-sterility in the transgenic plant.

In one embodiment, the transgenic plant is a maize plant. In one embodiment, the herbicide application prevents at least pollen shed or anther extrusion. In one embodiment, the development of the male reproductive tissue is a stage selected from the group consisting of the V4, V5, V6, V7, V8, V9, V10, V11, V12, V13, and V14 stage of maize plant development.

In one embodiment, the herbicide is selected from the group consisting of acetyl coenzyme A carboxylase (ACCase), acetolactate synthase (ALS) inhibitors, photosystem II (PSII) inhibitors, protoporphyrinogen oxidase (PPO) inhibitors, 4-hydroxyphenyl pyruvate dioxygenase (HPPD) inhibitors, 5-enolypyruvyl shikimate 3-phosphate synthase (EPSPS) inhibitors, glutamine synthetase (GS) inhibitors, and synthetic auxins. In one embodiment, the herbicide is glyphosate and the recombinant protein is a glyphosate-tolerant EPSPS.

A further aspect of the invention includes a method of producing hybrid seed including: (a) herbicide application to a transgenic plant including a recombinant DNA construct including a protein-coding sequence encoding a recombinant protein that confers herbicide tolerance to the transgenic plant operably linked to a DNA sequence including an mts-siRNA element, wherein the herbicide application is carried out during the development of the male reproductive tissue of the transgenic plant thereby inducing male-sterility in the transgenic plant; (b) fertilizing the transgenic plant with pollen from a second plant; and (c) harvesting hybrid seed from the transgenic plant. In one embodiment, the transgenic plant is maize. In one embodiment, the herbicide is glyphosate and the recombinant protein is a glyphosate-tolerant EPSPS. In one embodiment, the glyphosate is applied during the development at an effective dose of about 0.125 pounds acid equivalent per acre to about 8 pounds acid equivalent per acre.

Yet another aspect of the invention includes hybrid seed harvested from a male-sterile transgenic plant that has been fertilized with pollen from a second plant, wherein the male-sterile transgenic plant includes a recombinant DNA construct including a protein-coding sequence encoding a recombinant protein that confers herbicide tolerance to the transgenic plant operably linked to a DNA sequence including an mts-siRNA element, and wherein the transgenic plant has been induced to be male-sterile by application of an effective amount of herbicide during the development of the male reproductive tissue of the transgenic plant. In one embodiment, the hybrid seed is hybrid transgenic maize seed. In one embodiment, the herbicide is glyphosate and the recombinant protein is a glyphosate-tolerant EPSPS. In one embodiment, the glyphosate is applied during the development at an effective dose of about 0.125 pounds acid equivalent per acre to about 8 pounds acid equivalent per acre. In one embodiment, the herbicide application prevents at least pollen shed or anther extrusion. In one embodiment, the development of the male reproductive tissue is a stage selected from the group consisting of the V4, V5, V6, V7, V8, V9, V10, V11, V12, V13, and V14 stage of maize plant development.

EXAMPLES

Example 1

This example describes identification of mts-siRNAs and mts-siRNA elements. Bioinformatic analysis of sequencing data from multiple maize small RNA libraries identified a group of small RNAs (sRNAs) that were enriched or specifically expressed in maize tassel. The relative abundance of these mts-siRNAs in maize tassels ranged from about 50 to 631 transcripts per quarter million sequences, which is the normalized abundance. These sRNAs are identified as siRNAs because of their length (18-26 nucleotides) and their likely origin from a dsRNA precursor. Because of their expression pattern, the male tissue-specific siRNAs are referred to as "mts-siRNAs". As used herein, an "expression pattern" is any pattern of differential DNA, RNA, or protein expression. For example, a tassel-specific expression pattern refers to specific or enriched expression of a DNA, RNA, or protein in a tassel tissue and/or cell. Examples of the corresponding DNA sequence for mts-siRNAs, referred to herein as "mts-siRNA sequences", are provided as SEQ ID NO: 1-56 and 105-149.

These mts-siRNA sequences were then compared with cDNA sequence collections. A sequence comparison of the mts-siRNA against a maize unigene collection (compiled cDNA sequences) using BLAST yielded the surprising result that a large number of mts-siRNA clustered together, and were even overlapping, within a DNA region found in several closely related, but unique, cDNA sequences. The group of cDNA sequences all contained such a region, although the DNA sequence of the region varied due to different combinations and locations of individual mts-siRNA sequences and/or 1-3 nucleotide mismatches to individual mts-siRNA sequences. Such a region defined as having at least one mts-siRNA sequence within a nucleotide sequence window, is referred to herein as a "mts-siRNA element". In various embodiments, the nucleotide sequence window includes at least about 20 contiguous nucleotides (nt) (e.g., at least 18, 19, 20, 21, 22, 23, or 24 nt), at least about 25 nt, at least about 30 nt, at least about 40 nt, at least about 50 nt, at least about 100 nt, or at least about 150 nt. Examples of the DNA sequence for mts-siRNA elements are provided herein as SEQ ID NO: 57-94 and 96-104. An mts-siRNA element can have more than one mts-siRNA sequence, for example, at least two, at least three, at least four, at least five, or more than five mts-siRNA sequences within a given nucleotide sequence window. Two or more mts-siRNA sequences within a given mts-siRNA element may overlap because at least a portion of their nucleotide sequences are identical (see Table 5 for examples of mts-siRNAs that have overlapping nucleotide sequences).

Bioinformatic analysis indicated that multiple mts-siRNAs could be generated from the same RNA transcript, for example a transcript produced from one of the cDNA sequences described above as including an mts-siRNA element. Many of the mts-siRNAs were also found to have 1-3 mismatches when compared to mts-siRNA elements from across the group of closely related cDNA sequences. This is believed to indicate that these mts-siRNAs are generated from multiple, closely-related transcripts, resulting in a large, closely-related group of mts-siRNAs. Thus, an RNA transcript produced from a cDNA including an mts-siRNA element (containing multiple mts-siRNA sequences) would be complementary to, and therefore capable of hybridizing to, multiple mts-siRNAs and/or their complements. Thus, a naturally occurring mts-siRNA has an RNA sequence that is either a perfect or near-perfect complement to an mts-siRNA sequence (e.g., where the mts-siRNA has an RNA sequence with no more than approximately 1-3 mismatches relative to the mts-siRNA sequence); by extension that same mts-siRNA has an RNA sequence that is a perfect or near-perfect complement to a segment of an mts-siRNA element.

A sequence similarity search of the mts-siRNAs against a maize genomic DNA database using BLAST identified multiple loci with significant similarity to the mts-siRNA element. These loci were then analyzed for open reading frames (ORFs), but the identified putative polypeptides were not found to have significant homology to any known protein. Bioinformatic analysis of the mts-siRNA producing cDNA sequences indicated that there was no significant sequence homology at the nucleotide level to any known plant gene. These data suggest that mts-siRNAs could be produced from such loci by processing of dsRNA formed between transcripts of opposite polarity or by processing of dsRNA from aberrant transcripts due to RNA-dependent RNA polymerase activity. It also possible that mts-siRNAs are processed from internal secondary dsRNA structures that can be formed in some mts-siRNAs producing transcripts.

Reverse-transcription of the mts-siRNAs provided mts-siRNA sequences which were mapped onto one of the mts-siRNA elements (SEQ ID NO: 87). This is presented in FIG. 1 with the X-axis representing the nucleotide position from 5' to 3' orientation from left to right on the top and from right to left on the bottom. The relative abundance of the mts-siRNA is given as transcripts per quarter million sequences (tpq) plotted on the Y-axis. As can be seen from FIG. 1, a few mts-siRNAs (circled) are highly represented in the tassel-specific sRNA library (Y-axis). The predicted mts-siRNA sequences are also non-uniformly distributed across the mts-siRNA element (X-axis).

Example 2

This example illustrates endogenous tassel expression analysis of mts-siRNAs. The native in planta expression patterns of the mts-siRNAs were analyzed using several different methods. These analyses confirmed that the sRNAs that hybridize to mts-siRNA elements are enriched in and/or specifically expressed in tassels across maize germplasms (i.e., the mts-siRNAs are enriched in and/or specifically expressed in tassels), and that in an embodiment, an mts-siRNA is enriched in and/or specifically expressed in the pollen grain at the uninucleate microspore stage of pollen development.

To demonstrate in planta tassel-specific accumulation of the mts-siRNA, three representative mts-siRNA sequences (SEQ ID NO: 26 (1372590), SEQ ID NO: 8 (648011), SEQ ID NO: 33 (410590)) were used to design probes for low molecular weight (LMW) northern blot analysis of sRNAs prepared from either maize or rice. For these experiments, total RNA was extracted from plant tissue using TRIzol® reagent (Invitrogen, Carlsbad, Calif.). RNA (7.5 µg) from each sample was denatured at 95° C. for 5 minutes before separation on a 17% PAGE gel containing 7 M urea in 0.5× TBE buffer (Allen et al. (2004) Nature Genetics 36:1282-1290). Following electrophoresis, the gel was blotted onto a Nytran SuPerCharge® membrane (Whatman-Schleicher & Schuell, Florham Park, N.J.) using Trans-Blot® SD Semi-Dry Electrophoretic Transfer Cell (Bio-Rad, Hercules, Calif.) according to the manufacturer's protocol. The resulting blot was crosslinked at 1200 microjoules/cm$^2$×100 in a Stratalinker® 1800 (Stratagene, Cedar Creek, Tex.). To prepare the probes, an RNA probe template was generated by PCR and contained the T7 promoter on one end and one of the small RNA sequences on the opposite end. The sRNA sequences incorporated into the RNA probe template included: [1] Gma-miR159a (miRBase.org accession number MI0001773), which was used as a control for loading; [2] sR1372590 (SEQ ID NO: 26); [3] sR648011 (SEQ ID NO: 8); and [4] sR410590 (SEQ ID NO: 33). The RNA probes were transcribed using T7 RNA polymerase, and labelled with digoxigenin (DIG) using the DIG Northern Starter Kit (Roche, Indianapolis, Ind.), according to the manufacturer's protocol. Hybridization was performed with 100 ng of the DIG-labelled probe in PerfectHyb™ hybridization buffer (Sigma, St. Louis, Mo.) at 38° C. for 16 hrs. Detection was performed with the DIG Northern Starter Kit according to the manufacturer's protocol, before exposure to Kodak® Biomax™ XAR film (Sigma, St. Louis, Mo.). The samples tested included all, or a subset of the following: maize leaf from plants grown under nitrogen stress; maize shoot, root or endosperm from plants grown under cold stress; maize leaf and root from plants grown under drought stress; maize silk; maize young tassel; maize mature tassel; unpollinated maize kernels; maize embryo—24 days after pollination (DAP); maize kernels—22 DAP; mature maize kernels; maize embryo—mature (dry) kernels; maize endosperm—dry; rice grain; and rice seedling. The results obtained with the LMW northern analysis using at least three different mts-siRNA probes (sR1372590, sR648011, and sR410590) showed signal only in the lanes corresponding to the young tassel and mature tassel lanes, confirming the bioinformatic analysis and the conclusion that the mts-siRNA expression is highly enriched in or specific to tassel tissue.

Figure 2:
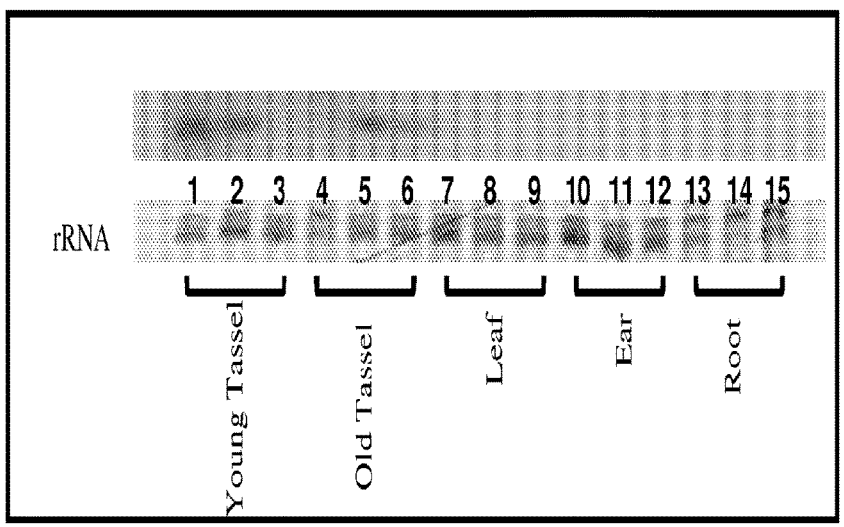
FIG. 2 depicts Northern blot analysis to measure tassel-specific sRNA expression, as described in Example 2.

The tissue specificity and accumulation of sRNAs that would recognize an mts-siRNA element was assessed across a wide spectrum of maize germplasm using LMW northern analysis. For this analysis an mts-siRNA element (SEQ ID NO: 87, which contains multiple mts-siRNA sequences) was selected. This mts-siRNA element includes the three mts-siRNA sequences used to design the siRNA probes sR1372590, sR648011, and sR410590, allowing these probes to be used for the LMW northern analysis of the maize germplasm samples. For these experiments, RNA was prepared from twenty different maize inbred lines with diverse genetic backgrounds, e.g., with relative maturity rating from 83 to 120 (Table 1). For three of these inbred lines (91DUA6, 01DKD2, and LH244), tissue was collected from young tassel, old tassel, leaf, ear, and root. Table 1 provides the corresponding V-stage and tassel size at collection of young tassel and old tassel. Total RNA was extracted using TRIzol® solution. LMW RNA was isolated with mirVana™ miRNA isolation kit (cat. no. AM1560, Ambion, Austin, Tex.). LMW northern analysis was done using a Bio-Rad Criterion™ Precast 15% TBE-urea acrylamide gel (cat. no. 345-0092, BioRad, Hercules, Calif.). The gel was blotted onto a positive charged membrane (cat. no. 11209272, Roche Applied Systems, Mannheim, Germany). Probes were labelled with either (1) 32-P-random priming, or (2) with DIG DNA using Roche PCR labeling kit, or (3) with DIG RNA probe as described above. All probes used to probe the northern blots were the reverse complement to the endogenous transcript or the cDNA sequence of the mts-siRNA element. The presence of sRNA that hybridized to the transgenic mts-siRNA element was specific to tassel; no signal was detected for leaf, ear, or root for any of the three inbred maize genotypes 91DUA6, 01DKD2, and LH244 (FIG. 2).

To determine the temporal expression pattern during tassel development of sRNAs which would recognize an mts-siRNA element (SEQ ID NO: 87), LMW northern analysis was done. RNA was prepared from young and old tassel from different maize inbred lines, see Table 1. The RNA preparation and LMW northern techniques were essentially as described above.

TABLE 1

Inbred germplasm, maturity rating, and tassel development stage

| Inbred | Maturity rating | young tassel | | old tassel | |
|---|---|---|---|---|---|
| | | Stage | Tassel size (inches) | Stage | Tassel size (inches) |
| C3SUD402 | 108 | V9 | 5 | V12 | 10 |
| HIQA202 | 113 | V9-10 | 4.5 | V13 | 13 |
| BEBE788 | 83 | V10-11 | 10 | V13 | 7.5 |
| BIQA207 | 103 | V10 | 7 | V11 | 9.5 |
| DIDA404 | 112 | V10 | 2.5-3 | V11 | 9.5 |
| 5DA92 | 107 | V10-11 | 5.7 | V12 | 11 |
| DIDA406 | 109 | V10 | 6.5 | V12 | 9 |
| 80DJD5 | 114 | V10 | 6.5 | V11 | 10 |
| JEDO115 | 120 | V9 | 2.5 | V11-12 | 10 |
| FIDA240 | 116 | V9-10 | 2.5 | V12 | 11 |
| BIQA347 | 99 | V9-10 | 3.5 | V11-12 | 10.5-11 |
| HOQA203 | 105 | V10-11 | 5.5 | V12-13 | 11 |
| 91DUA6 | 90 | V10-11 | 10 | V12-13 | 10 |
| BIDA345 | 95 | V10 | 5 | V12-13 | 10 |
| 01DKD2 | 111 | V9-10 | 5 | V13 | 10.5-11 |
| DIDA403 | 108 | V10 | 2.5-3 | V12 | 10.5-11 |
| 64DJD1 | 105 | V9-10 | 2.5-3 | V12 | 10.5-11 |
| DIQA423 | 108 | V9-10 | 3 | V12 | 9.5 |
| BIQA208 | 102 | V10 | 5.5 | V13 | 9.5 |
| LH244 | 111 | V9-10 | 1-2.5 | V13 | 10 |

Figure 4:
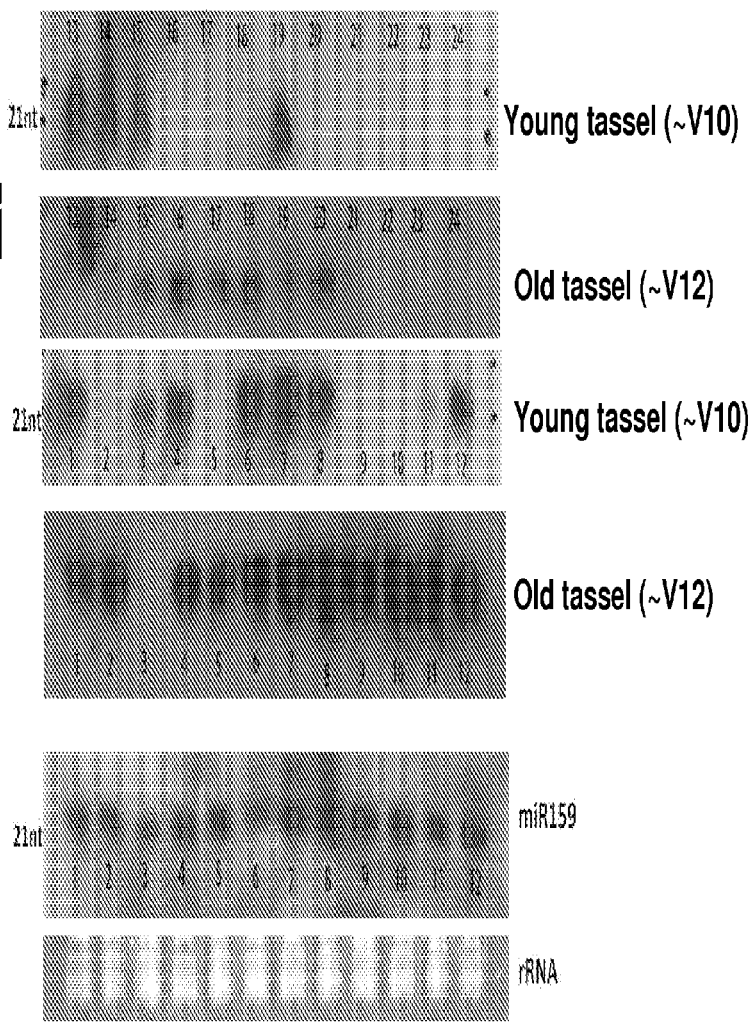
FIG. 4 depicts Northern blot analysis of tassel maturity temporal expression of an mts-siRNA element (SEQ ID NO: 87) using RNA from different inbred germplasm, as described in Example 2.

As seen in FIG. 4, a DIG-labelled RNA probe corresponding to the reverse complement of an mts-siRNA element (SEQ ID NO: 87) hybridized to sRNA in both young and old tassel, with the exception of young tassel that was 2.5 inches to 3 inches in length: lanes 5 (inbred DIDA404), 9 (inbred JEDO115), 10 (inbred FIDA240), 16 (inbred DIDA403), 17 (inbred 64DJD1), 18 (inbred DIQ423), and 20 (inbred LH244). Additionally, this experiment confirmed no detection of sRNA hybridizing to the mts-siRNA element from samples of leaf (lanes 21 and 22) or ear (lanes 23 and 24) from the inbreds BIQA208 and LH244. Collectively these data indicate that the sRNAs that hybridize to the mts-siRNA element are specifically expressed in the tassel from each inbred genotype tested when the tassel is greater than about 3.5 inches.

Figure 5:
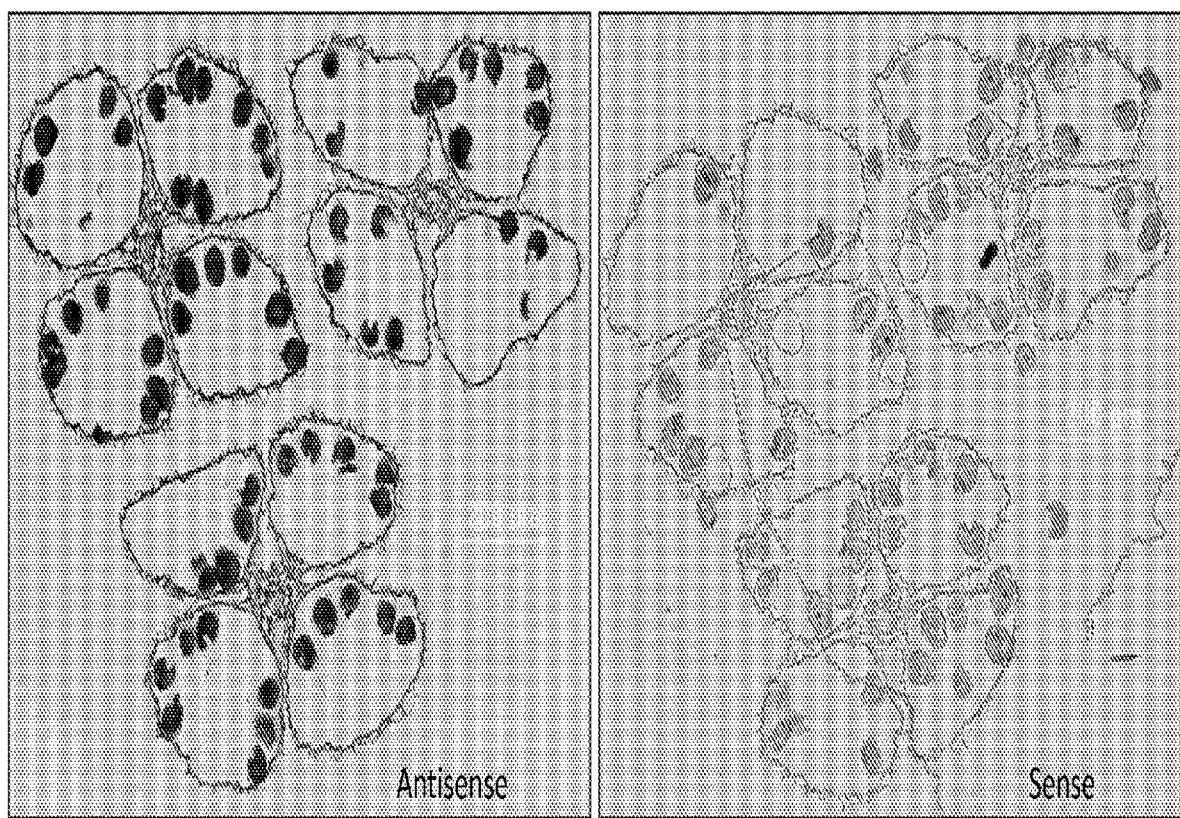
FIG. 5 depicts in situ localization of siRNA expression in mature anther using antisense (left panel) or sense (right panel) probes for an mts-siRNA sequence (sR648011, SEQ ID NO: 8), as described in Example 2

In situ hybridization analysis was done to investigate cell specific expression of an mts-siRNA sequence (sR648011, SEQ ID NO: 8). In maize anthers, microspores are produced through meiosis and develop into mature pollen. Maize microsporegenesis can be roughly divided into the following stages: meiosis of sporogenous cells, release of tetrads as free microspores, mitosis of uninucleate microspores to produce tricellular pollen, and mature pollen grains. For these experiments, maize tassel before anthesis obtained from maize plants grown under standard conditions in a greenhouse was used. Locked Nucleic Acid (LNA) probes (Integrated DNA Technologies, Coralville, Iowa) were used as indicated below with the position of the LNA indicated by a '+' symbol. The antisense probe was designed to detect the mts-siRNA for sR648011 (SEQ ID NO: 8) (5'-Biotin-CAT+GCA+CTG+GTG+AGT+CAC+TGT-3'), while the sense probe was the reverse complement of the antisense probe (5'-Biotin-ACA+GTG+ACT+CAC+CAG+TGC+ATG-3') for use as a negative control. The LNA probes allow high stringent washes and therefore ensure highly specific hybridization (Válóczi et al., 2006; Nuovo et al., 2009). All probes were biotin labelled. The samples of maize tassel were fixed in 4% paraformaldehyde in 1×PBS at 4° C. for 36 h, and then dehydrated at 4° C. through a graded ethanol:H$_2$O series. The tassels were then placed in 75% EtOH and 25% Histoclear (National Diagnostics, Atlanta, Ga.) for 1.5 h, 50% EtOH and 50% Histoclear for 1.5 h, 25% EtOH and 75% Histoclear for 1.5 h, and 100% Histoclear for 3×1.5 h, all at 25° C. Next, the Histoclear was gradually replaced with molten paraplast at 50° C., and the tassels were transferred into molds and stored at 4° C. before sectioning. The paraffin-embedded tassels were sectioned on a microtome to 8 μm thickness. A series of sections were made from the same anthers and adjacent sections were then used for probing with the sense or antisense probe, respectively. Prehybridization and hybridization were conducted at 42° C. and washing at 55° C. Detection of the biotin-labelled LNA probes annealed with the transcripts was with a 1 to 400 dilution of Anti-Biotin-Alkaline Phosphatase (AP) and BM Purple AP Substrate (Roche Applied Science, Indianapolis, Ind.). Images were captured from a camera on an Olympus microscope (Center Valley, P.A.). Sections from the same anthers were divided into two groups—one was used for the antisense probe (FIG. 5, left panel) and the other for the sense probe (FIG. 5, right panel). The hybridization signal (dark purple) was detected only on the sections that were hybridized with the antisense probe but not on those that were incubated with the sense probe (FIG. 5). The strong signal obtained with the antisense probe indicates that this mts-siRNA was abundant (highly expressed) in the pollen grain at the uninucleate microspore stage of pollen development.

Example 3

Figure 3:
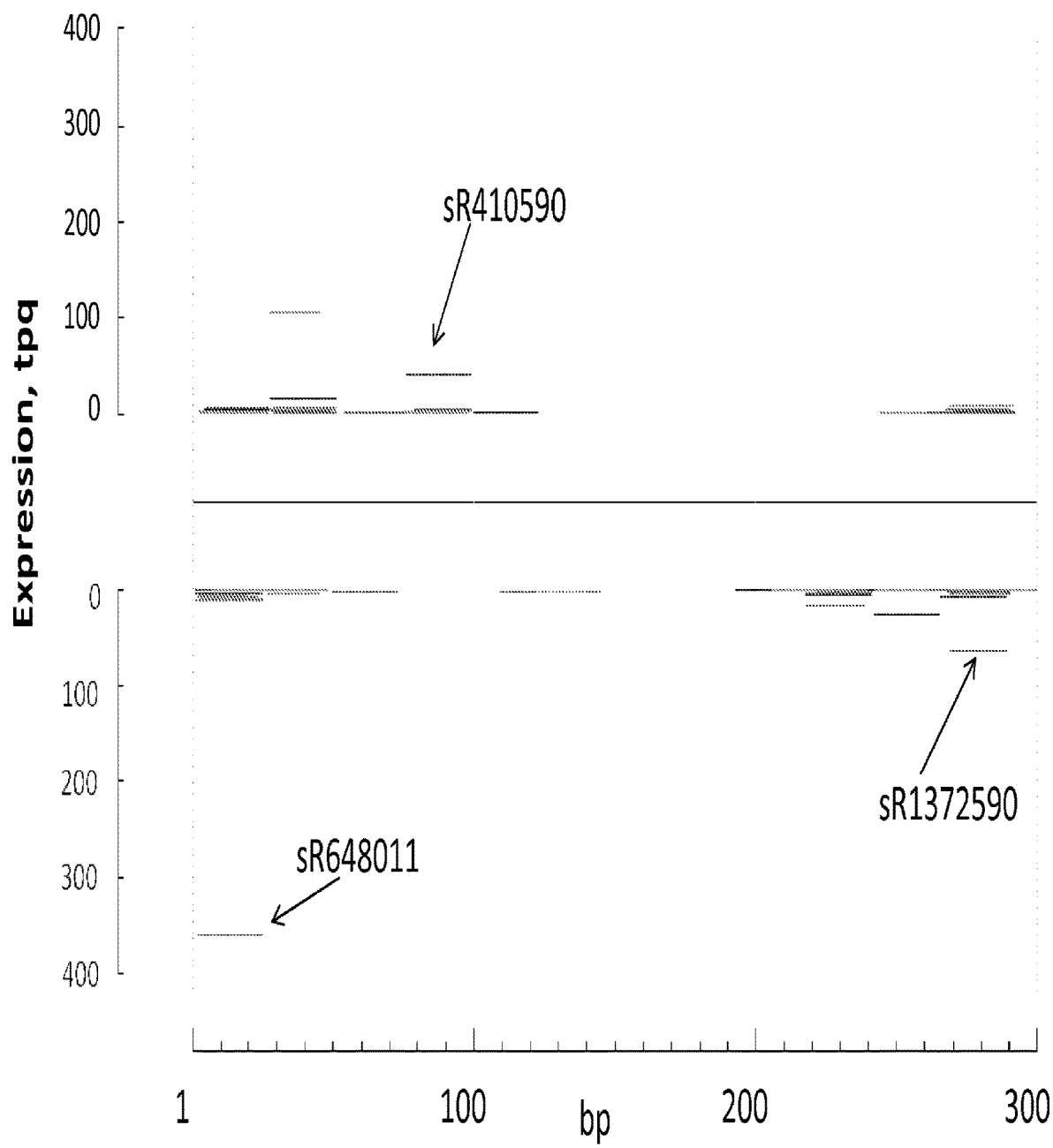
FIG. 3 depicts mapping of mts-siRNA sequences on an mts-siRNA element (SEQ ID NO: 87), as described in Examples 2 and 8. The X-axis from left to right represents the orientation of the mts-siRNA element with the top strand represented in the top half of the chart and the bottom strand represented in the bottom half of the chart; the nucleotide position from 5' to 3' orientation is shown from left to right on the top and from right to left on the bottom. The mts-siRNA sequences are shown in their relative alignment positions. The three mts-siRNA sequences used to design three specific probes (sR648011 (SEQ ID NO: 8), sR1372590 (SEQ ID NO: 26), and sR410590 (SEQ ID NO: 33)) are indicated.

This example illustrates plant transformation constructs and transgenic plant production. An mts-siRNA element was incorporated into the 3'UTR of a transgene expression cassette and used to produce transgenic maize plants to test the effect of the element on transgene expression in transgenic plants. An mts-siRNA element (SEQ ID NO: 87) was inserted into the 3'UTR of a CP4-EPSPS transgene expression cassette for maize transformation. This mts-siRNA element was selected because it has an abundance of mts-siRNA sequences in it (FIG. 3), including sequences for three of the siRNA probes (sR1372590, sR648011 and sR410590) used for the LMW northern analysis in Example 2. This mts-siRNA element also allowed testing the effect of mts-siRNA mismatches. The mts-siRNA element tested here (SEQ ID NO: 87) has a one nucleotide change (C$\Delta$T: AAGCTATTGATTCCCTAAGTGCCA) compared to one of the underlying mts-siRNA sequences (SEQ ID NO: 33, used to design Probe sR410590). The mts-siRNA element was inserted in the transgene cassette in the reverse complement orientation relative to its position in the endogenous cDNA, but the element is believed to function similarly in both orientations because tassel-specific siRNA molecules complementary to either strand of the mts-siRNA element can be found in maize tassel (FIGS. 1 and 3).

Several CP4-EPSPS/mts-siRNA element expression cassettes were constructed (Table 2) and used to transform maize plants. Different combinations of expression elements were tested in the CP4-EPSPS/mts-siRNA element expression cassettes. Expression elements such as promoters, leaders, introns, chloroplast transit peptides, and 3'UTR's needed for efficient and stable expression of a transgene are well known in the art. The CP4-EPSPS/mts-siRNA element expression cassettes were designed to include one of two separate promoters; operably linked to a DNA of one of two separate leaders; operably linked to a DNA of one of two introns; operably linked to one of two DNA molecules encoding the same chloroplast transit peptide (CTP); operably linked to a DNA molecule derived from the aroA gene from the *Agrobacterium* sp. strain CP4 and encoding the CP4-EPSPS protein; operably linked to DNA encoding an mts-siRNA element; operably linked to one of two 3'UTR DNA molecules. Construct 4 contained the wildtype CP4-EPSPS gene and all the other vectors contained a plant codon optimized version of the CP4-EPSPS gene. Constructs 3, 5, and 6 (Table 2) were designed to determine if an mts-siRNA element incorporated into the 3'-UTR would produce plants with tassel-specific sensitivity to glyphosate and vegetative glyphosate tolerance. Constructs 4 and 7 are control constructs, lacking an mts-siRNA element.

TABLE 2

Plant transformation constructs

| Construct | Promoter | Leader | Intron | CTP | Transgene | mts-siRNA | 3'UTR |
|---|---|---|---|---|---|---|---|
| 3 | A | A | A | A | CP4 | SEQ ID NO: 87 | A |
| 4 | A | A | A | A | CP4 | ** | A |
| 5 | B | B | B | B | CP4 | SEQ ID NO: 87 | A |
| 6 | B | B | B | B | CP4 | SEQ ID NO: 87 | B |
| 7 | B | B | B | B | CP4 | ** | A |

Transgenic maize plants transformed with one of each of the five expression cassettes were produced using well-known methods. Briefly, maize cells were transformed by *Agrobacterium*-mediated transformation with one each of the constructs listed in Table 2 (individually) and regenerated into intact maize plants. Individual plants were selected from the population of plants that showed integrity of the transgene expression cassette and resistance to glyphosate. Rooted plants with normal phenotypic characteristics were selected and transferred to soil for growth and further assessment. R0 plants were transferred to soil for growth, sprayed with 0.75 lb/acre glyphosate at V3-V4 followed by 0.75 lb/acre glyphosate at V7-V9, and then cross-pollinated with pollen from non-transgenic maize plants of the same germplasm (for constructs 3, 5, and 6 events) or self-pollinated (for constructs 4 and 7 events) to produce R1 seed. Plants were then selected by a combination of analytical techniques, including TaqMan, PCR analysis, and vegetative tolerance to herbicide spray and a reduced (desired) male fertility rating following herbicide (glyphosate) spray.

Example 4

This example illustrates methods of analyzing transgenic plants in a greenhouse. Transgenic plants transformed with the CP4-EPSPS/mts-siRNA element expression cassettes were analyzed for vegetative glyphosate tolerance and male fertility. Transgenic plants generated from constructs containing the CP4-EPSPS/mts-siRNA element expression cassettes were found to have vegetative tolerance to glyphosate and induced male-sterility with late application of glyphosate.

R0 plants were grown in duplicates in the green house and left unsprayed or sprayed with 0.75 lb/acre glyphosate at the (early) V6 stage followed by 0.75 lb/acre glyphosate at the (late) V9 stage. (FIG. 7 and Table 3) The R0 events tested were multi-copy events. All R0 plants that were unsprayed had normal anther extrusion and fully fertile pollen as determined by Alexander staining. All R0 plants that were sprayed had vegetative tolerance to glyphosate. R0 plants produced from constructs 4 and 7, which did not contain the mts-siRNA element, did not show tassel sensitivity to glyphosate or induced male-sterility. R0 plants produced from constructs 3, 5, and 6, which did contain the mts-siRNA element, showed tassel sensitivity to glyphosate and induced male-sterility; these plants had no or very few anther extrusions and >99% of the pollen was non-viable as determined by Alexander staining.

TABLE 3

Glyphosate spray data

| Construct | Early Glyphosate Spray Vegetative Tolerance | Late Glyphosate Spray Induced Male-sterility |
|---|---|---|
| 3 | Yes | Yes |
| 4 | Yes | No |
| 5 | Yes | Yes |
| 6 | Yes | Yes |
| 7 | Yes | No |

These observations demonstrated that the presence of the mts-siRNA element in the 3'UTR of a transgene cassette led to tassel-specific transgene silencing of the transgene. Tassel-specific loss of the mRNA transcript produced by CP4-EPSPS/mts-siRNA element expression cassette resulted in tassels which were sensitive to glyphosate, producing a plant with induced male-sterility, while the other tissues of the plant were glyphosate tolerant, producing vegetative glyphosate tolerance and good female fertility.

Immunolocalization was then used to measure CP4-EPSPS protein in the transgenic plant tissues. Tassel was obtained from plants transformed with construct 3 or construct 4 and from non-transgenic maize (LH198). The plants were grown in a greenhouse with 14 hours of light at 80° F.

and 8 hours of dark at 70° F. One seed was planted per pot. The pots were randomly arranged on the greenhouse floor. Plants were watered as necessary and fertilized with 20-20-20 mixture of nitrogen, potassium and phosphorus, respectively. Plants from construct 3 or construct 4 were sprayed with glyphosate at 0.75 lb/acre at the V2 stage to confirm vegetative tolerance to glyphosate. Young tassels were harvested at V10-V11 for anther tissues at microspore mother cell and free microspore stages; mature tassels were harvested at the T7 stage, 1-2 days before pollen shedding, for anther tissues with fully-developed pollen. Anthers were removed from the tassel spikelet using dissecting forceps and immediately fixed in 3.7% formaldehyde in phosphate buffered saline (PBS) under gentle vacuum. After washing in PBS, tissues were placed in embedding medium and frozen immediately. Frozen tissue blocks were stored at −80° C. until sectioned in −20° C. microtome and collected on the charged slides.

Figure 6B:
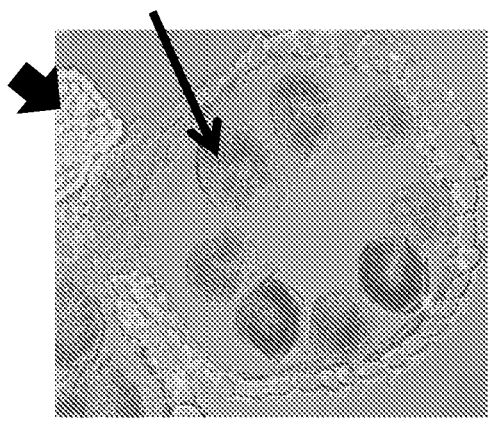
FIG. 6 depicts CP4-EPSPS protein localization in anthers from unsprayed plants transgenic for construct 3 (FIG. 6A) or construct 4 (FIG. 6B), as described in Example 4. Construct 3 transgenic maize plants contain a CP4-EPSPS/mts-siRNA element expression cassette. Construct 4 plants are a control.
Figure 6A:
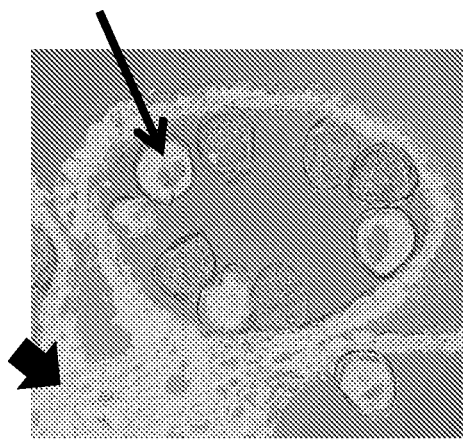
Figure 7D:
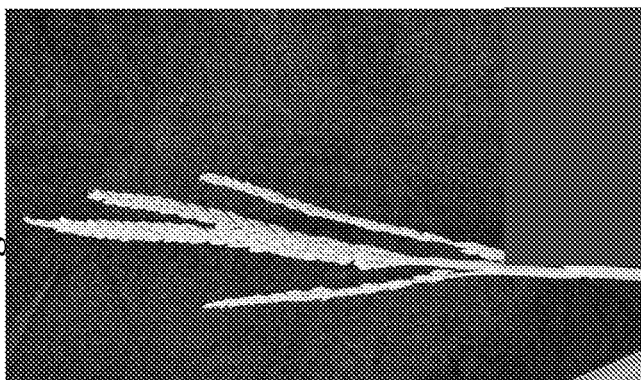
FIG. 7D shows tassels from sprayed transgenic plants.
Figure 7E:
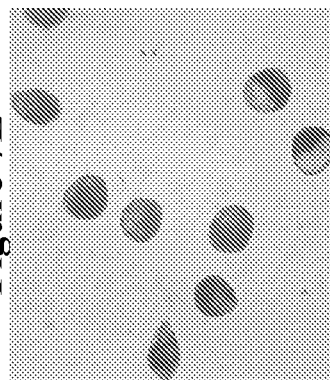
FIG. 7E shows pollen grains from sprayed transgenic plants.
Figure 7B:
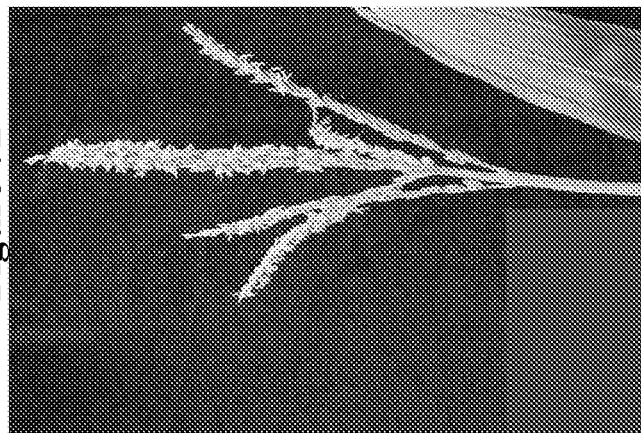
FIG. 7B shows tassels from unsprayed transgenic plants.
Figure 7C:
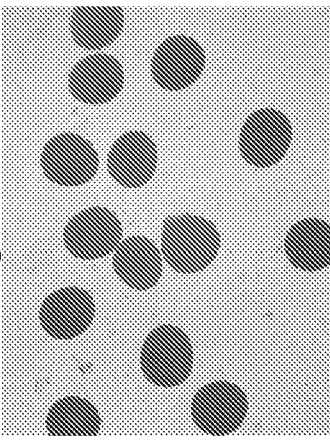
FIG. 7C shows pollen grains from unsprayed transgenic plants.
Figure 7A:
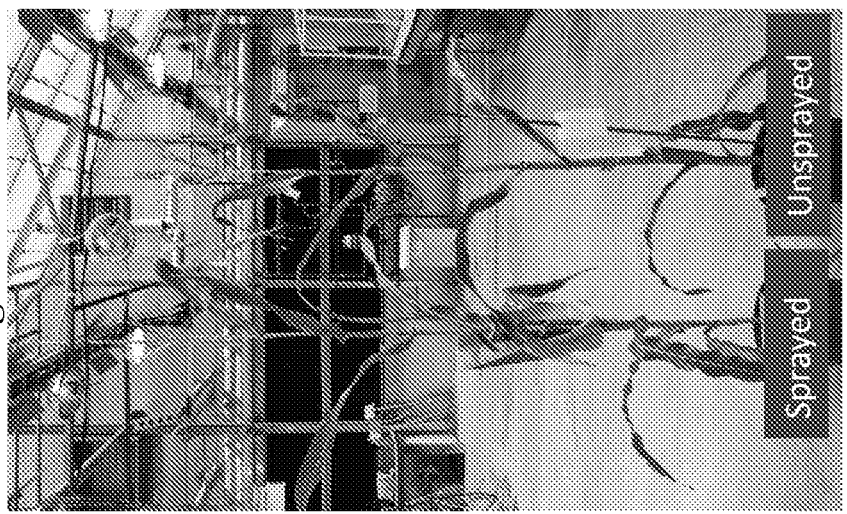
FIG. 7A shows glyphosate-sprayed and unsprayed transgenic maize plants.

Tissue sections were blocked with blocking agent (10% normal goat serum, 5% bovine serum albumin, 0.1% Triton X-100 in PBS) for 2 hours. Sections were incubated with anti-CP4-EPSPS antibody (1/500 in PBS). After washing the sections three times in PBS, tissue sections were incubated with the secondary antibody, goat anti-mouse IgG conjugated with Alexa fluorophore 488 (Invitrogen, Eugene, Oreg.). For a negative control, CP4-EPSPS antibody incubation was omitted. As a positive control, an antibody to α-tubulin (Sigma, St. Louis, Mo.), a cytoskeletal protein expressed in most cell types, was substituted for the CP4-EPSPS antibody on separate sections. Both primary and secondary antibodies were incubated at room temperature for 2-4 hours and then further incubated overnight at 4° C. After washing, the tissues were imaged with Zeiss Laser Scanning Microscope (LSM) 510 META confocal microscope using a 488 nm laser for excitation and 500-550 nm for emission filter set. The same imaging parameter was applied throughout the samples including controls. Fluorescent and bright field images were scanned from each section, and merged using LSM software afterward to show structural information. A strong signal was obtained with the anti-CP4-EPSPS antibody in filament tissue (FIG. 6A, short arrow) and pollen (FIG. 6A, long arrow) in mature tassel from plants generated with construct 4 (FIG. 6A), lacking the mts-siRNA element. The plant in FIG. 6A is hemizygous for the transgene cassette, therefore only about 50% of the pollen showed the positive CP4-EPSPS signal. In contrast, a strong signal was obtained with the anti-CP4-EPSPS antibody only in filament tissue (FIG. 6B, short arrow) and no signal was seen in pollen (FIG. 6B, long arrow) in mature tassel from plants generated with construct 3 containing the mts-siRNA element (FIG. 6B). The positive control antibody (anti-alpha-tubulin) showed signal in pollen within the mature tassel from plants generated from either construct 4 or construct 3. The data for the negative controls showed the expected absence of signal. The data for the conventional non-transgenic control showed the expected absence of signal from staining with the anti-CP4-EPSPS antibody and positive signal with staining with the anti-alpha-tubulin antibody. These data indicate that no or very few transcripts from the transformation cassette containing the mts-siRNA element are translated in the pollen, but that the transcript was translated in the vegetative filament tissue. The loss of CP4-EPSPS protein expression in pollen correlates to the observed tassel-specific glyphosate sensitivity in plants generated from construct 3.

Example 5

This example illustrates transgenic plant field trial testing for male fertility or sterility. Thirteen confirmed single-copy R1-R3 transgenic plant events generated by transformation with the CP4-EPSPS/mts-siRNA element expression cassette (construct 3) were tested in field trials for efficacy of the expression cassette. In the first year, thirteen events were tested at one field location. In the second year, eight events were tested at four field locations. In the third year, four events were tested in four field locations. During the three years of field trials, the average male fertility rating (MFR) for events generated from construct 3 was near or below MFR 2, which is considered the industry standard for male-sterility.

Figure 8B:
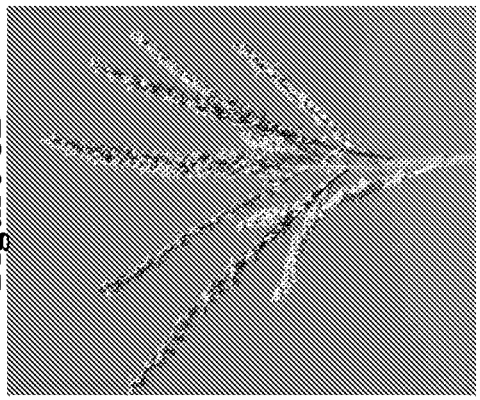
FIG. 8B depicts a tassel from a plant treated with a weed-only spray treatment.
Figure 8C:
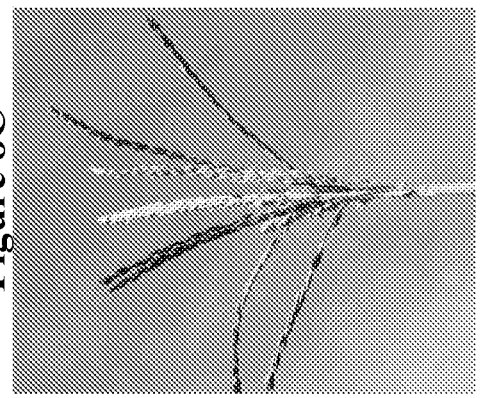
FIG. 8C depicts a tassel from a plant treated with a late glyphosate spray treatment for inducing male-sterility.
Figure 8A:
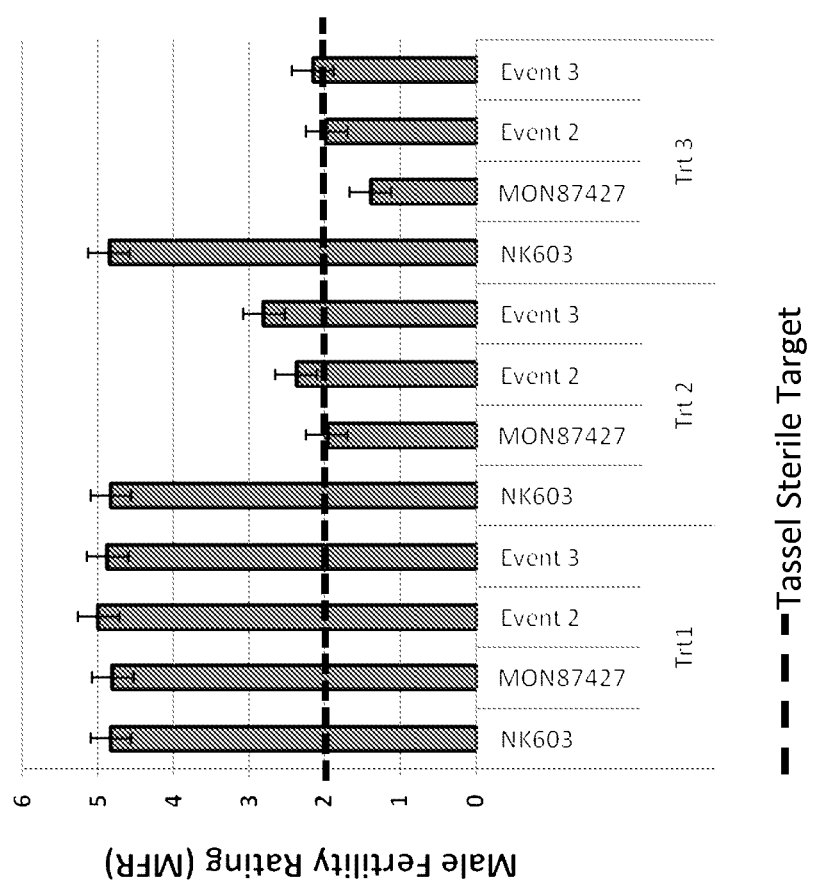
FIG. 8A shows average MFR produced under three different glyphosate spray treatment regimens (Trt 1, Trt 2, and Trt 3) for NK603 (CP4-EPSPS transgenic maize), MON87427 (CP4-EPSPS transgenic maize with glyphosate-inducible male-sterility), and two events from construct 3, as described in Example 5; the dashed line indicates the industry standard for male-sterility, MFR 2.

The data for one year of efficacy field trials is presented in FIG. 8, with the average MFR produced under three different glyphosate spray treatment regimens presented in the graph (FIG. 8A) for NK603 (CP4-EPSPS transgenic maize), MON87427 (CP4-EPSPS transgenic maize with glyphosate-inducible male-sterility), and two events from construct 3. Photos of tassel from plants grown during this particular efficacy field trial illustrate fertile tassel when the plants were sprayed with glyphosate at 0.75 lb/acre only at V3 (FIG. 8B); and sterile tassel (no or minimal anther extrusion) on plants sprayed with glyphosate 0.75 lb/acre at V3 followed by 0.75 lb/acre at V8 followed by 0.75 lb/acre at V10 (FIG. 8C). For this field trial, the spray regimens were: treatment 1 consisted of 0.75 lb/acre glyphosate at V3 (weed control); treatment 2 consisted of 0.75 lb/acre glyphosate at V3 (weed control) followed by 0.75 lb/acre at V8 followed by 0.75 lb/acre at V10; treatment 3 consisted of 0.75 lb/acre glyphosate at V3 (weed control) followed by 1.25 lb/acre at V8 followed by 1.25 lb/acre at V10. The later two sprays (i.e., V8 and V10) are referred to as sterility sprays. These results indicate that with only weed control glyphosate spray treatment 1 all plants (NK603, MON87427, and construct 3 events) were male fertile. With glyphosate sterility spray treatment 2, NK603 plants had a MFR=5, MON87427 were sterile with a MFR=2, and events 2 and 3 of construct 3 were partially male-fertile with a MFR<3. With glyphosate sterility spray treatment 3, NK603 plants had a MFR=5, MON87427 were male-sterile with a MFR<2, and events 2 and 3 of construct 3 were male-sterile with a MFR near or below a score of 2.

Although the average MFR was near or at a score of 2, anther extrusion was observed in glyphosate treated construct 3 events at S90+3 and S90+6 (FIG. 9). For these data, four separate construct 3 events were compared to MON87427 and NK603 plants for two glyphosate spray regimens: treatment 2 consisted of 1.5 lb/acre glyphosate at V2/V3 (weed control) followed by 0.75 lb/acre glyphosate at growing degree units (GDU) 875 (~V8) followed by 0.75 lb/acre glyphosate at GDU 1025 (~V10) and treatment 3 consisted of 1.5 lb/acre glyphosate at V2/V3 (weed control), followed by 1.25 lb/acre glyphosate at GDU 875 (~V8) followed by 1.25 lb/acre glyphosate at GDU 1025 (~V10). The number of plants per plot (68-74 plants/plot) showing anther extrusion were scored at S90, S90+3 and S90+6, where S90 is the day when 90% of the plants in the field are showing silk; S90+3 is 3 days after S90; and S90+6 is 6 days after S90. As seen in the FIG. 9, at S90 there were 70(±15) NK603 plants per plot showing anther extrusion for both glyphosate treatment regimens. In contrast, for the MON87427 and the four construct 3 events, there was 1(±12) plant per plot showing anther extrusion at S90 for both glyphosate treatment regimens. At S90+3 and S90+6, there were 30(±12) to 70(±12) plants per plot for the four construct 3 events showing anther extrusion with either glyphosate treatment regimen, nearing that seen for NK603. The anther extrusion for the MON87427 event remained at the S90 level for both S90+3 and S90+6 time points, and for each glyphosate treatment regimens. Any plants with ≥1 extruded anther were scored as positive for anther extrusion. This late anther extrusion, i.e. S90+3 and S90+6, occurs at a time of maize development when there is a maximum growth height of the tassel and there is sufficient distance to allow machine cutting of the tassel with minimal injury to the top two leaves of the maize plant, hence minimal impact on inbred yield. Also, anther extrusion at S90+3 or later is considered to have little impact on seed purity.

Analysis of pollen viability was conducted to determine if the low level, but consistent anther extrusion observed at S90+3 to S90+6 was an indication of potential late breaking male fertility. FIGS. 10A and 10B illustrate an example of late breaking anther extrusion in tassel from a sterility sprayed construct 3 event. The box in FIG. 10A is the portion magnified in FIG. 10B. An example of late breaking anther extrusion is circled in FIG. 10B. To determine pollen viability, pollen was gathered from late breaking extruded anther and stained with Alexander stain, FIG. 10C. Pollen was also gathered from non-sprayed construct 3 events on the same day and stained with Alexander stain as a comparison, FIG. 10D. The results of this Alexander staining shows only non-viable pollen (translucent light blue, irregular shape pollen grains) from the late breaking anthers of sprayed construct 3 events (FIG. 10C). Fully viable pollen appears opaque, dark purple and spherical with Alexander stain (FIG. 10D). In addition to staining pollen collected from individually isolated late breaking extruded anther, pollination bags were placed on some sprayed construct 3 events to determine pollen shed. No noticeable pollen was shed into these pollination bags, which failed to generate any seed when used to cross pollinate recipient ears. This result suggested that there was no pollen shed from the late extruding anthers or that any pollen shed is non-viable.

Collectively, these data indicate that although there is low level anther extrusion from sterility sprayed construct 3 events, these extruded anthers do not shed viable pollen.

Example 6

Figure 11:
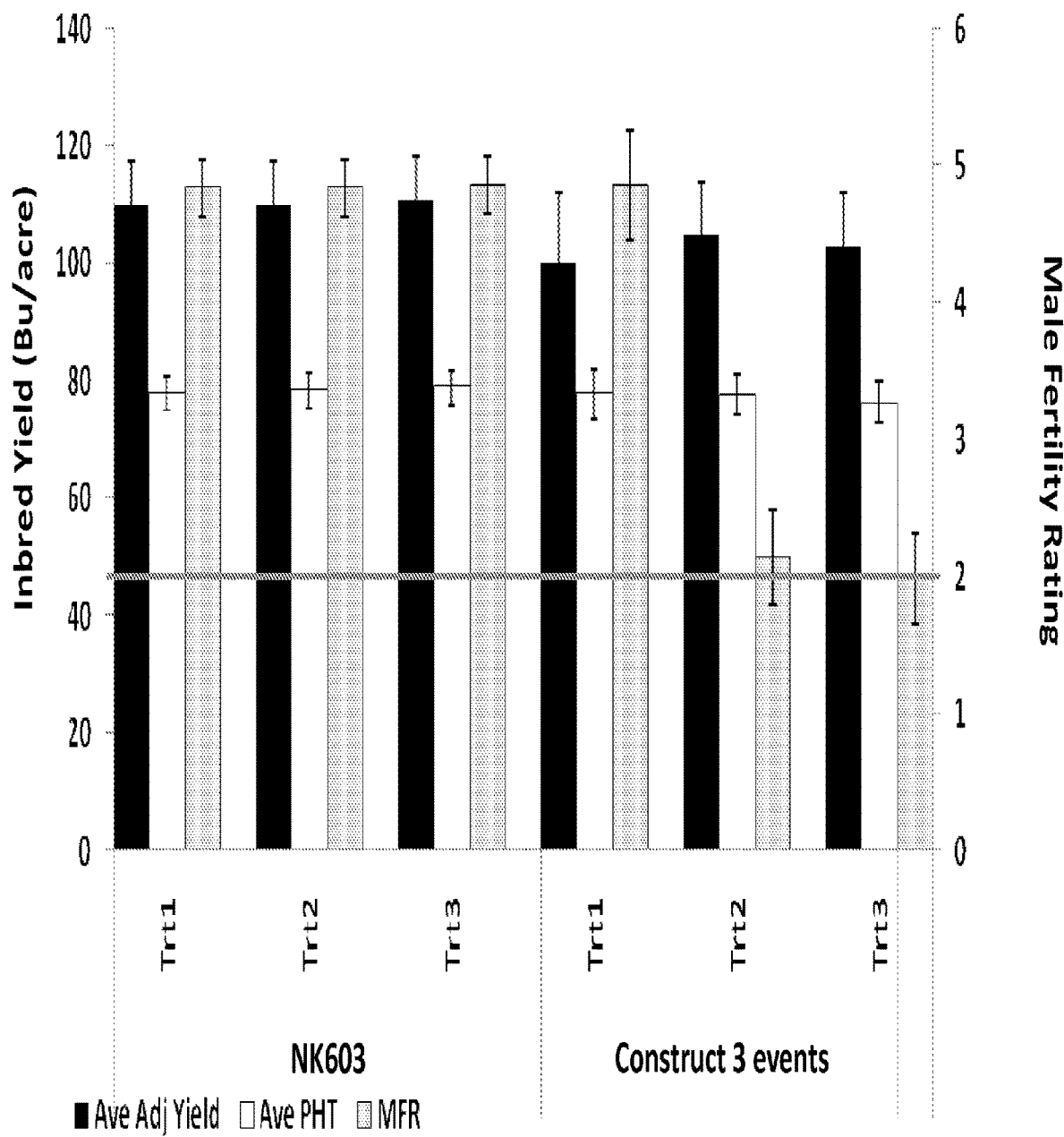
FIG. 11 depicts results of field trial testing of NK603 plants and construct 3 events for inbred grain yield and male fertility, as described in Example 6. Inbred yield was measured as bushels/acre (Bu/acre) and induced male-sterility was measured as Male Fertility Rating (MFR). The horizontal bar indicates the industry standard for male-sterility, MFR 2. Trt 1, Trt 2, and Trt 3 refer to treatment regimens 1, 2, and 3.

This example illustrates transgenic plant field trials testing for yield. Construct 3 R2 plants were tested for inbred and hybrid yield. For inbred yield, construct 3 R2 plants were tested in four field locations for yield, vegetative tolerance to glyphosate spray, and male-sterility with glyphosate spray. For these field trials, four events from construct 3 were planted in plots of 68-74 plants/plot. The spray treatments were: treatment 1 consisted of 1.5 lb/acre glyphosate at V3 (weed control); treatment 2 consisted of 1.5 lb/acre glyphosate at V3 followed by 0.75 lb/acre at V8 followed by 0.75 lb/acre at V11; treatment 3 consisted of 1.5 lb/acre glyphosate at V3 followed by 1.25 lb/acre at V8 followed by 1.25 lb/acre at V11. As can be seen in FIG. 11, the construct 3 events at all three glyphosate treatment regimens showed good vegetative tolerance (white bars) as measured by plant height and good inbred yield (black bars) as measured as bushels (Bu)/acre. These same events were fully male-fertile when treated with only the weed control glyphosate treatment regimen (treatment 1), but were male-sterile with a MFR score of equal to or less than 2 (gray bars) when treated with glyphosate treatment regimens 2 or 3. The horizontal bar on FIG. 11 indicates the industry standard for sterility, MFR 2. NK603 is provided for comparison. The measures of yield of inbred grain for construct 3 events and NK603 with glyphosate spray are provided in Table 4, where MST=% moisture of the grain, TWT=test weight (a density rating, typically pounds per bushel), and S50D is number of days to 50% silking of the ears in the plot. There was no significant difference (nd) measured in yield for any of the four construct 3 events tested with either glyphosate treatment 2 or 3 compared to the NK603 control.

TABLE 4

Inbred grain yield measures

Comparison of Treatments 2 and 3 to Treatment 1

| Events | MST | TWT | S50D |
|---|---|---|---|
| cNK603 | nd | nd | nd |
| Event 1 | nd | nd | nd |
| Event 2 | nd | nd | nd |
| Event 4 | nd | nd | nd |
| Event 3 | nd | nd | nd |

Figure 12:
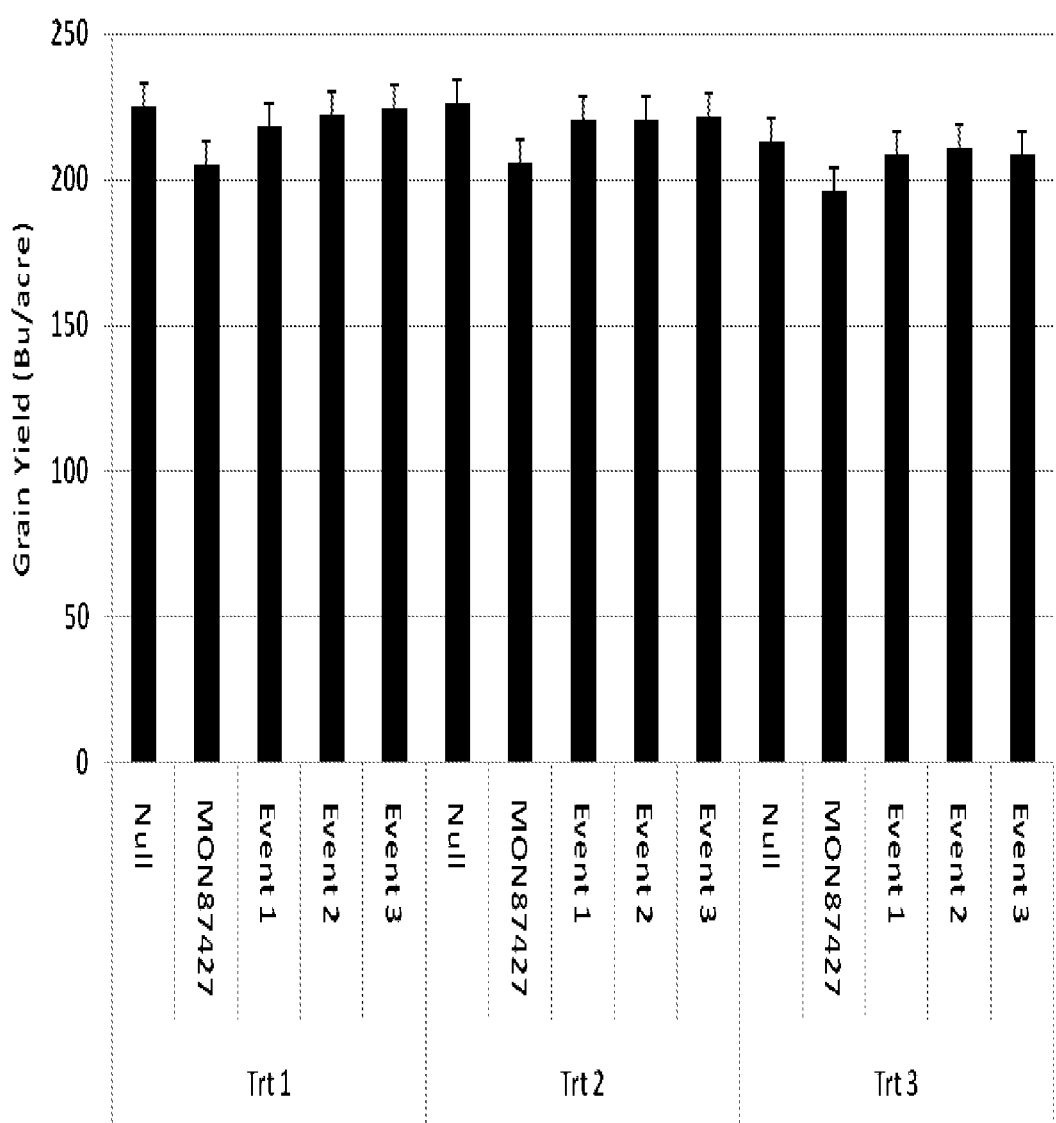
FIG. 12 depicts results of field trial testing of a non-transgenic female inbred (Null), line MON87427, and three events from construct 3, all in the same genetic background, which were cross pollinated with a male MON810/MON88017 tester to generate F1 hybrid seed. Hybrid grain yield was measured as bushels/acre (Bu/acre). Trt 1, Trt 2, and Trt 3 refer to treatment regimens 1, 2, and 3.

For F1 hybrid grain yield, construct 3 R3 events were tested in four field locations. For these hybrid yield field trials, a non-transgenic female inbred (Null), line MON87427, and three events from construct 3, all in the same genetic background, were cross pollinated with a male MON810/MON88017 tester to generate F1 hybrid seed. The F1 hybrid seed generated from each of these crosses was planted in standard plots of 68-74 plants/plot. The spray treatments consisted of treatment 1 of no glyphosate spray; treatment 2 of 2.25 lb/acre glyphosate at V4 followed by 2.25 lb/acre at V7; treatment 3 of 2.25 lb/acre glyphosate at V4 followed by 2.25 lb/acre at V7 followed by 2.25 lb/acre at V10. The F1 plants were open pollinated to generate F2 grain, which is the yield measured in bushels/acre (Bu/acre). All three construct 3 events showed equivalent F1 hybrid grain yield at all glyphosate treatment regimens when compared to the control crosses of NullxMON810/MON88017 and MON87427xMON810/MON88017 (FIG. 12).

Example 7

This example illustrates male fertility restoration in F1 hybrid plants. F1 hybrid plants generated from a cross of construct 3 events as the female parent were tested for male fertility. Three different F1 hybrid crosses were set-up: non-transgenic female x MON88017 male; MON87427 female x MON88017 male; and construct 3 event female x MON88017 male. The F1 hybrid seed was harvested from each of the three crosses, planted in a field, and sprayed with glyphosate at 1.125 lb/acre at V4 followed by 1.125 lb/acre at V10. Male fertility in F1 was assessed by male fertility rating (MFR) and by Alexander viability staining of the pollen. For each of the crosses, the MFR of the F1 hybrid plants was 5, or fully fertile. The Alexander viability staining showed 50% of the pollen produced by the F1 hybrid of each of the crosses was viable, as expected. (FIG. 13) These data indicate that male fertility can be functionally restored in F1 hybrid plants produced from glyphosate-inducible male-sterile transgenic plants transformed with a CP4-EPSPS/mts-siRNA element expression cassette.

Example 8

This example illustrates variant and chimeric mts-siRNA element construction. Individual mts-siRNA were mapped onto an mts-siRNA element as presented in FIG. 3; the X-axis indicates the nucleotide position from 5' to 3' orientation from left to right on the top and from right to left on the bottom, and the Y-axis indicates the relative abundance of the mts-siRNA is indicated as transcripts per quarter million sequences (tpq). The mts-siRNAs were also non-uniformly distributed across the mts-siRNA element (X-axis).

Using this information, variants of an mts-siRNA element and/or chimeras produced using one or more mts-siRNA element(s) were engineered to contain more (or fewer) total mts-siRNA sequences (optionally or alternatively, one or more mts-siRNA sequence(s) is added or deleted), resulting in more (or less) silencing of an operably linked protein-coding sequence. Such variants or chimeric mts-siRNA elements are useful for increasing or decreasing the selective suppression of the expression of a recombinant protein in a male reproductive tissue of a transgenic plant.

Examples of variants and chimeras of mts-siRNA elements were constructed using fragments of SEQ ID NO: 87. The first variant (SEQ ID NO: 88) was constructed using a 104 nucleotide fragment from the 5'-end of SEQ ID NO: 87. The second variant (SEQ ID NO: 89) was constructed using an 80 nucleotide fragment from the 3'-half of SEQ ID NO: 87. Chimeric mts-siRNA elements were constructed by joining one fragment (SEQ ID NO: 88) to another fragment (SEQ ID NO: 89) to form new chimeric mts-siRNA elements (SEQ ID NO: 90 and SEQ ID NO: 91). Additional chimeric mts-siRNA elements were constructed by joining three individual mts-siRNA contained within SEQ ID NO: 87: a first chimera (SEQ ID NO: 92) was constructed by joining mts-siRNA sequences SEQ ID NO: 26, 27, and 8; a second chimera (SEQ ID NO: 93) was constructed by joining mts-siRNA sequences SEQ ID NO: 10, 33, and 5; a third chimera (SEQ ID NO: 94) was constructed by joining mts-siRNA sequences SEQ ID NO: 26, 10, and 33. These variants and chimeras can be operably linked to protein-coding sequences to produce recombinant DNA constructs (see FIG. 14) that can be tested in plants and plant cells for selective suppression of a recombinant protein encoded by the protein-coding sequence in a male reproductive tissue of a transgenic plant.

Example 9

This example illustrates design of variant and chimeric mts-siRNA elements. Variant and chimeric mts-siRNA elements were designed based on a 300-nucleotide (nt) long mts-siRNA element having SEQ ID NO: 81, which is similar to the 300-nucleotide mts-siRNA elements having SEQ ID NO: 82 and 87. A highly conserved consensus sequence for mts-siRNA elements SEQ ID NO: 81, 82, and 87 is provided by SEQ ID NO: 96. Individually, each of these are also useful as an mts-siRNA element or as the basis of designing variant or chimeric mts-siRNA elements, e.g., by selecting fragments of an mts-siRNA element identified from genomic sequence or cDNAs, such as fragments including at least one mts-siRNA sequence, and combining or concatenating such fragments.

Two fragments within SEQ ID NO: 81 were selected; fragment A (SEQ ID NO: 97) contained 104 contiguous nucleotides from the 5' region (positions 1-104) of SEQ ID NO: 81 and fragment B (SEQ ID NO: 98) contained 80 contiguous nucleotides from the 3' region (positions 215-294) of SEQ ID NO: 81; it is clear that either fragment A (SEQ ID NO: 97) or fragment B (SEQ ID NO: 98) individually are mts-siRNA elements containing at least one mts-siRNA sequence. The location of fragments A and B (indicated by underlined text) is shown in the following full sequence of SEQ ID NO: 81, which also indicates the location of mts-siRNA sequences (indicated by italicized text; italicized segments of greater than 18 contiguous nucleotides can include more than one overlapping mts-siRNA sequences) found to map to this mts-siRNA element:

(SEQ ID NO: 81)
GGACAACAAGCACCTTCTTGCCTTGCAAGGCCTCCCTTCCCTATGGTAGC

CACTTGAGTGGATGACTTCACCTTAAAGCTATCGATTCCCTAAGTGCCAG

ACATAATAGGCTATACATTCTCTCTGGTGGCAACAATGAGTCATTTTGGT

TGGTGTGGTAGTCTATTATTGAGTTTGTTTTGGCACCGTACTCCCATGGA

GAGTACAAGACAAACTCTTCACCGTTGTAGTCGTTGATGGTATTGGTGGT

GACGACATCCTTGGTGTGCATGCACTGGTGAGTCACTGTTGTACTCGGCG.

Variant mts-siRNA elements were designed using the "A" and "B" fragments, including an "A+B" mts-siRNA element (SEQ ID NO: 99) and a "B+A" mts-siRNA element (SEQ ID NO: 100). A chimeric element (SEQ ID NO: 101) was designed to include the mts- mts-siRNA sequences (shown above in italicized text in SEQ ID NO: 81) that were found to map to the mts-siRNA element (SEQ ID NO: 81).

Similarly, a 251-nt long mts-siRNA element (SEQ ID NO: 102) and a 121-nt long mts-siRNA element (SEQ ID NO: 103, a fragment of SEQ ID NO: 102, i.e., the contiguous segment located at nucleotide positions 47-167 of SEQ ID NO: 102) were identified from maize genomic sequence (Zm_B73_CR10::Segment{75361491 . . . 753617421}) as tassel-specific and corresponding to mts-siRNAs from young tassel (maize LH244, library 347; individually identified mts-siRNAs in some cases overlap over much of their sequence and vary by only a few nucleotides; see Table 5). Based on SEQ ID NO: 102 and 103 a chimeric mts-siRNA element (SEQ ID NO: 104) was designed.

TABLE 5 mts-siRNAs mapped to SEQ ID NO: 103

| library ID | sRNA ID (specific to each library) | map start* | map end* | strand | expression (tpq for lib9, raw counts for others) | SEQ ID NO: | Sequence (as DNA equivalent) |
|---|---|---|---|---|---|---|---|
| 347 | 710618 | 48 | 72 | −1 | 1 | 105 | ACCAAAGCCGCAATACTTAGCCCTA |
| 347 | 325 | 49 | 72 | −1 | 667 | 106 | ACCAAAGCCGCAATACTTAGCCCT |
| 9 | 75221 | 49 | 72 | −1 | 14.0375 | 107 | ACCAAAGCCGCAATACTTAGCCCT |
| 9 | 79587 | 49 | 70 | −1 | 1.7547 | 108 | CAAAGCCGCAATACTTAGCCCT |

TABLE 5-continued mts-siRNAs mapped to SEQ ID NO: 103

| library ID | sRNA ID (specific to each library) | map start* | map end* | strand | expression (tpq for lib9, raw counts for others) | SEQ ID NO: | Sequence (as DNA equivalent) |
|---|---|---|---|---|---|---|---|
| 347 | 1443964 | 49 | 70 | -1 | 1 | 109 | CAAAGCCGCAATACTTAGCCCT |
| 347 | 1798947 | 50 | 72 | -1 | 1 | 110 | ACCAAAGCCGCAATACTTAGCCC |
| 9 | 993198 | 51 | 74 | 1 | 5.264 | 111 | GGCTAAGTATTGCGGCTTTGGTAG |
| 346 | 2511625 | 56 | 79 | -1 | 1 | 112 | GACAACTACCAAAGCCGCAATACT |
| 347 | 1978935 | 62 | 84 | -1 | 1 | 113 | GATATGACAACTACCAAAGCCGC |
| 347 | 955660 | 63 | 86 | -1 | 1 | 114 | TAGATATGACAACTACCAAAGCCG |
| 347 | 1183103 | 64 | 84 | -1 | 1 | 115 | GATATGACAACTACCAAAGCC |
| 347 | 36752 | 73 | 96 | -1 | 12 | 116 | ATCAAAAGTTTAGATATGACAACT |
| 347 | 151532 | 75 | 98 | 1 | 4 | 117 | TTGTCATATCTAAACTTTTGATAG |
| 347 | 1372 | 97 | 120 | -1 | 197 | 118 | ACGAGTACTCTAACATATAAGACT |
| 347 | 316040 | 97 | 117 | -1 | 2 | 119 | AGTACTCTAACATATAAGACT |
| 347 | 1310155 | 98 | 121 | 1 | 1 | 120 | GTCTTATATGTTAGAGTACTCGTT |
| 347 | 26503 | 99 | 122 | 1 | 15 | 121 | TCTTATATGTTAGAGTACTCGTTA |
| 347 | 490490 | 109 | 132 | -1 | 2 | 122 | ATCAAAACCCTAACGAGTACTCTA |
| 347 | 1125767 | 114 | 137 | -1 | 1 | 123 | AGACAATCAAAACCCTAACGAGTA |
| 347 | 442804 | 115 | 138 | -1 | 2 | 124 | GAGACAATCAAAACCCTAACGAGT |
| 347 | 965720 | 118 | 141 | -1 | 1 | 125 | CAGGAGACAATCAAAACCCTAACG |
| 345 | 1549424 | 119 | 142 | -1 | 1 | 126 | ACAGGAGACAATCAAAACCCTAAC |
| 347 | 311196 | 120 | 143 | -1 | 2 | 127 | CACAGGAGACAATCAAAACCCTAA |
| 347 | 190 | 121 | 144 | -1 | 1018 | 128 | ACACAGGAGACAATCAAAACCCTA |
| 346 | 591709 | 121 | 144 | -1 | 2 | 129 | ACACAGGAGACAATCAAAACCCTA |
| 347 | 363241 | 121 | 143 | -1 | 2 | 130 | CACAGGAGACAATCAAAACCCTA |
| 347 | 1603891 | 121 | 141 | -1 | 1 | 131 | CAGGAGACAATCAAAACCCTA |
| 347 | 135176 | 122 | 144 | -1 | 4 | 132 | ACACAGGAGACAATCAAAACCCT |
| 347 | 48157 | 123 | 146 | 1 | 9 | 133 | GGGTTTTGATTGTCTCCTGTGTAT |
| 347 | 1866298 | 123 | 144 | -1 | 1 | 134 | ACACAGGAGACAATCAAAACCC |
| 347 | 1707358 | 124 | 147 | -1 | 1 | 135 | AATACACAGGAGACAATCAAAACC |
| 347 | 1788406 | 129 | 146 | 1 | 1 | 136 | TGATTGTCTCCTGTGTAT |
| 347 | 519539 | 130 | 153 | 1 | 2 | 137 | GATTGTCTCCTGTGTATTTACCCT |
| 347 | 383791 | 133 | 156 | -1 | 2 | 138 | GAGAGGGTAAATACACAGGAGACA |
| 347 | 273115 | 135 | 158 | 1 | 2 | 139 | TCTCCTGTGTATTTACCCTCTCGC |
| 345 | 1244664 | 135 | 157 | -1 | 1 | 140 | CGAGAGGGTAAATACACAGGAGA |
| 346 | 1460995 | 135 | 157 | -1 | 1 | 141 | CGAGAGGGTAAATACACAGGAGA |
| 347 | 697148 | 135 | 157 | 1 | 1 | 142 | TCTCCTGTGTATTTACCCTCTCG |
| 347 | 1716970 | 136 | 159 | 1 | 1 | 143 | CTCCTGTGTATTTACCCTCTCGCA |
| 347 | 839648 | 137 | 157 | -1 | 1 | 144 | CGAGAGGGTAAATACACAGGA |

TABLE 5-continued mts-siRNAs mapped to SEQ ID NO: 103

| library ID | sRNA ID (specific to each library) | map start* | map end* | strand | expression (tpq for lib9, raw counts for others) | SEQ ID NO: | Sequence (as DNA equivalent) |
|---|---|---|---|---|---|---|---|
| 347 | 8578 | 145 | 168 | -1 | 38 | 145 | TACAATAAGTGCGAGAGGGTAAAT |
| 9 | 519321 | 145 | 168 | -1 | 8.7734 | 146 | TACAATAAGTGCGAGAGGGTAAAT |
| 347 | 423280 | 145 | 167 | -1 | 2 | 147 | ACAATAAGTGCGAGAGGGTAAAT |
| 347 | 377787 | 146 | 168 | -1 | 2 | 148 | TACAATAAGTGCGAGAGGGTAAA |
| 9 | 444803 | 146 | 167 | -1 | 1.7547 | 149 | ACAATAAGTGCGAGAGGGTAAA |

*nucleotide position within SEQ ID NO: 103

Example 10

This example illustrates vectors and transgenic plant cells, tissues, and plants containing recombinant DNA constructs including a protein-coding sequence encoding a recombinant protein and an mts-siRNA element operably linked to the protein-coding sequence.

A plant transformation vector comprising a recombinant DNA construct is used for Agrobacterium-mediated transformation of maize cells. This transformation vector includes DNA for Agrobacterium-mediated transfer of T-DNA, an expression cassette (promoter operably linked to a DNA sequence of interest), a selectable marker expression cassette (for convenient selection of the transformed maize cells or plants), and DNA for maintenance of the vector in E. coli (e.g., an E. coli origin of replication sequence). In one embodiment, the transformation vector includes an expression cassette comprising a recombinant DNA construct flanked by right and left border sequences from Agrobacterium, wherein the recombinant DNA construct includes the herbicide tolerance transgene CR-AGRtu.aroA-CP4.nat (provided as SEQ ID NO: 95) as the DNA sequence encoding a recombinant protein. The herbicide tolerance transgene CR-AGRtu.aroA-CP4.nat is operably linked to the mt-siRNA provided as SEQ ID NO: 81 as the DNA sequence encoding an mts-siRNA element.

Transformation vectors for expressing different recombinant DNA constructs are constructed by inserting a polynucleotide including an mts-siRNA element (e.g., SEQ ID NO: 57-94 or 97-104) into the plant transformation vector. The mts-siRNA element is inserted adjacent to the DNA sequence encoding a recombinant protein or within the 3' untranslated region of the DNA sequence encoding a recombinant protein. Such plant transformation vectors are useful for making transgenic plants that can be induced to be male-sterile by the application of herbicide.

Methods for transformation of plants are well-known in the art. For example, maize plants of a transformable line are grown in the greenhouse and ears are harvested when the embryos are 1.5 to 2.0 mm in length. Ears are surface sterilized with 80% ethanol, followed by air drying. Immature embryos are isolated from individual kernels from sterilized ears. Prior to inoculation of maize cells, individual cultures of Agrobacterium each containing a transformation vector for expressing at least one of the recombinant DNA constructs of this invention are grown overnight at room temperature. Immature maize embryo cell cultures are inoculated with Agrobacterium, incubated at room temperature with Agrobacterium for 5 to 20 minutes, co-cultured with Agrobacterium for 1 to 3 days at 23 degrees Celsius in the dark, transferred to a selection medium and cultured for approximately 2 weeks to allow embryogenic callus to develop. Embryogenic callus is transferred to a culture medium containing 100 mg/L paromomycin and subcultured at about two week intervals. Multiple events of transformed plant cells are recovered 6 to 8 weeks after initiation of selection.

Transgenic maize plants are regenerated from transgenic plant cell callus for each of the multiple transgenic events resulting from transformation and selection, by placing transgenic callus of each event on a medium to initiate shoot and root development into plantlets which are transferred to potting soil for initial growth in a growth chamber at 26 degrees Celsius, followed by growth on a mist bench before transplanting to pots where plants are grown to maturity. The regenerated plants are self-fertilized. First generation ("R1") seed is harvested. Plants grown from the R1 seed ("R2" plants) are used to produce progeny.

Example 11

This example illustrates methods of selecting mts-siRNA sequences and mts-siRNA elements for use in recombinant DNA constructs including a protein-coding sequence encoding a recombinant protein and an mts-siRNA element operably linked to the protein-coding sequence.

One method of verifying efficacy of an mts-siRNA element for selectively suppressing the expression of a recombinant protein in a male reproductive tissue of a transgenic plant involves use of a protoplast assay wherein plant cell protoplasts are co-transformed with: (a) a vector containing a recombinant DNA construct including a protein-coding sequence and a mts-siRNA element operably linked to the protein-coding sequence; and (b) RNA(s) having the sequence of the siRNA(s) corresponding to the mts-siRNA element(s) (or alternatively, the mts-siRNA sequence(s)), wherein the level of expression of the recombinant protein is expected to be inversely proportional to the degree to which the mts-siRNA element is cleaved by the RNA(s).

This is illustrated by the following non-limiting example. The assay was carried out on two mts-siRNA sequences (corresponding to two siRNAs found to be highly expressed in maize tassel). In brief, maize leaf protoplasts were co-transformed with: (a) a plasmid (3 micrograms/320,000 cells) containing a recombinant DNA construct including a protein-coding sequence encoding a recombinant protein (CP4-EPSPS, SEQ ID NO: 95) and an mts-siRNA element (SEQ ID NO: 81), and (b) a first dsRNA with a first strand having the sequence SEQ ID NO: 150 in 5' to 3' direction and a second strand being the complement of the first, and a second dsRNA with a first strand having the sequence SEQ ID NO: 151 in 5' to 3' direction and a second strand being the complement of the first. The dsRNAs (from Integrated DNA Technologies, Inc., Coralville, Iowa) were tested at 0, 5, 25, or 50 nanograms/320,000 cells, with the total RNA used in each co-transformation assay adjusted with "filler" RNA consisting of either miRNA395 (as the mature 21-mer, provided as dsRNA) or yeast tRNA to 50 nanograms/320,000 cells. The level of CP4-EPSPS protein was determined by ELISA and used to evaluate the ability of the tested dsRNAs to suppress expression of the recombinant protein. Results are provided in Table 6.

TABLE 6

Level of CP4-EPSPS protein

| dsRNA tested | dsRNA (ng) | filler RNA (ng) | CP4-EPSPS protein (ng/mg total protein) |
|---|---|---|---|
| none (control) | 0 | 50 | 317 |
| SEQ ID NO: 150 | 5 | 45 | 294 |
|  | 25 | 25 | 167* |
|  | 50 | 0 | 114* |
| SEQ ID NO: 151 | 5 | 45 | 315 |
|  | 25 | 25 | 223* |
|  | 50 | 0 | 91* |

*statistically significant from control

Each of the dsRNAs (SEQ ID NO: 150 and 151) strongly suppressed CP4-EPSPS expression (indicated by decreased CP4-EPSPS protein accumulation) when co-transformed with the plasmid containing the recombinant DNA construct including the CP4-EPSPS protein-coding sequence and mts-siRNA element. The observed suppression of CP4-EPSPS was dose-dependent on the amount of dsRNAs and independent of the type of filler RNA. Suppression of CP4-EPSPS was not observed in control samples co-transformed with filler RNA in place of the test dsRNAs.

Example 12

This example illustrates recombinant DNA constructs, vectors, and transformed plants of the invention. Vectors and transformation methods similar to those described in Example 10 were used to produce stably transformed maize plants containing in their genome a recombinant DNA construct including a protein-coding sequence operably linked to a DNA sequence comprising an mts-siRNA element. Six combinations of construct design/mts-siRNA element were tested (see Table 7). Plants were sprayed twice (at V5 and V8) with 0.75 lb ae/A Roundup WeatherMAX®. Results are provided in Table 7. For each construct design/mts-siRNA element combination, about 20 plants were left unsprayed for comparison to glyphosate-sprayed plants. Unsprayed plants all shed pollen and had good male fertility (data not shown). The maize plants transformed with construct design B exhibited more pronounced male-sterility than the maize plants transformed with construct design A. Construct designs (5' to 3', left to right) were Construct A is promoter A/intron A/transit peptide A/CP4-EPSPS (SEQ ID NO: 95)/mts-siRNA element/3'UTR and Construct B is promoter B/intron B/transit peptide B/CP4-EPSPS/mts-siRNA element/3'UTR. As used below, "n.m." means not measured. The male fertility rating (MFR) scale is: 5=anther emergence is normal, pollen volume is the same as unsprayed plots but may or may not shed pollen; 4=anther emergence 50% of normal, but are shedding slightly or not shedding normal amounts of pollen; 3=tassel looks normal but there is sporadic anther extrusion (>10 anthers per tassel) and little or no pollen being shed; 2.5=no pollen shed, anthesis is greatly reduced (<10 anthers per tassel) or is very late (1 week) relative to the end of silking; 2=no pollen shed, no anthesis or anthesis is very late (1 week) relative to end of silking; and 1=no pollen shed, tassel has abnormal stick phenotype or anthesis is delayed two or more weeks after silking. S90 is when 90% plants have silk ready for pollination and S90+3 is 3 days after S90.

TABLE 7

Construct design/mts-siRNA element spray data

| Construct design* | mts-siRNA element SEQ ID NO: | Vegetative damage | Pollen shedding at S90 | MFR at S90 to S90 + 2 | % abnormal pollen |
|---|---|---|---|---|---|
| A | 97 | No | No | 5 | 100% |
| A | 97 | No | No | 2.5 | 100% |
| A | 97 | No | No | 2 | 100% |
| A | 98 | No | Yes | 5 | n.m. |
| A | 98 | No | No | 3 | 60% |
| A | 98 | No | No | 5 | 70% |
| A | 98 | No | No | 2.5 | 100% |
| A | 104 | No | No | 4 | n.m. |
| A | 104 | No | No | 2 | 50% |
| A | 104 | No | No | 2.5 | 100% |
| B | 101 | No | No | 2 | n.m. |
| B | 101 | No | No | 2.5 | 100% |
| B | 101 | No | No | 4 | n.m. |
| B | 101 | No | No | 2 | n.m. |
| B | 101 | No | No | 2.5 | n.m. |
| B | 101 | No | No | 2.5 | 100% |
| B | 101 | No | No | 2 | 100% |
| B | 101 | No | No | 2.5 | 100% |
| B | 101 | No | No | 2.2 | n.m. |
| B | 101 | No | No | 3 | 20% |
| B | 101 | No | No | 2 | 100% |
| B | 97 | No | No | 2.5 | n.m. |
| B | 97 | No | No | 2 | 100% |
| B | 97 | No | No | 2.5 | 100% |
| B | 97 | No | No | 4 | 100% |
| B | 97 | No | No | 2 | n.m. |
| B | 98 | No | No | 2 | 100% |
| B | 98 | No | No | 2.5 | 100% |
| B | 98 | No | No | 2 | n.m. |
| B | 98 | No | No | 2.5 | n.m. |

All of the materials and methods disclosed and claimed herein can be made and used without undue experimentation as instructed by the above disclosure. The above examples are included to demonstrate embodiments of the invention. It should be appreciated by those of skill in the art that the techniques disclosed in the examples represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. All such similar substitutes and modifications apparent to those skilled in the art are deemed to be within the spirit, scope and concept of the invention as defined by the appended claims.

What is claimed is:

1. A recombinant DNA construct comprising a protein-coding sequence operably linked to a polynucleotide sequence comprising a maize male tissue-specific siRNA (mts-siRNA) element comprising at least one DNA sequence complementary to an mts-siRNA specifically expressed in male reproductive tissue, wherein said maize mts-siRNA element comprises a fragment of a nucleotide sequence selected from the group consisting of SEQ ID NOs: 1-94 and 96-149, wherein said fragment comprises at least 18 contiguous nucleotides, and wherein the presence of said fragment in said maize mts-siRNA element selectively suppresses expression of said protein-coding sequence in a male reproductive tissue cell.

2. The recombinant DNA construct of claim 1, wherein the expression of said protein-coding sequence in a transgenic plant confers at least vegetative herbicide tolerance to said plant.

3. The recombinant DNA construct of claim 2, wherein said protein-coding sequence encodes a glyphosate-tolerant EPSPS.

4. A method of making a recombinant DNA construct comprising operably-linking a polynucleotide sequence comprising a maize mts-siRNA element comprising at least one DNA sequence complementary to an mts-siRNA specifically expressed in male reproductive tissue, wherein said maize mts-siRNA element comprises a fragment of a nucleotide sequence selected from the group consisting of SEQ ID NOs:1-94 and 96-149, wherein said fragment comprises at least 18 contiguous nucleotides, and wherein the presence of said fragment in said maize mts-siRNA element selectively suppresses expression of said protein-coding sequence in a male reproductive tissue cell to a protein-coding sequence.

5. The method of claim 4, wherein said mts-siRNA element is tassel-specific.

6. A transgenic plant having in its genome the recombinant DNA construct of claim 1.

7. A seed, progeny, or plant part of the transgenic plant of claim 6.

8. The transgenic plant of claim 6, wherein said transgenic plant is a monocotyledonous plant.

9. The transgenic plant of claim 6, wherein said transgenic plant is a maize plant.

10. A method of selectively suppressing the expression of a recombinant protein in a male reproductive tissue of a transgenic plant comprising expressing in said transgenic plant a recombinant DNA construct of claim 1.

11. The method of claim 10, wherein said male reproductive tissue is a tassel of a maize plant.

12. The method of claim 10, wherein said mts-siRNA element comprises a fragment of at least 18 contiguous nucleotides from at least three nucleotide sequences selected from the group consisting of SEQ ID NOs:1-94 and 96-149.

13. The method of claim 10, wherein the expression of said recombinant protein in a transgenic plant confers at least vegetative herbicide tolerance to said plant.

14. The method of claim 13, wherein said recombinant protein is a glyphosate-tolerant EPSPS.

15. A method of inducing male-sterility in a transgenic plant comprising applying an effective amount of an herbicide to a transgenic plant comprising a recombinant DNA construct of claim 1, wherein said herbicide application is carried out during the development of the male reproductive tissue of said transgenic plant thereby inducing male-sterility in said transgenic plant.

16. The method of claim 15, wherein said transgenic plant is a maize plant.

17. The method of claim 15, wherein said herbicide application prevents at least pollen shed or anther extrusion.

18. The method of claim 15, wherein said development of the male reproductive tissue is a stage selected from the group consisting of the V4, V5, V6, V7, V8, V9, V10, V11, V12, V13, and V14 stage of maize plant development.

19. The method of claim 15, wherein said herbicide is selected from the group consisting of acetyl coenzyme A carboxylase (ACCase) inhibitors, acetolactate synthase (ALS) inhibitors, photosystem II (PSII) inhibitors, protoporphyrinogen oxidase (PPO) inhibitors, 4-hydroxyphenyl pyruvate dioxygenase (HPPD) inhibitors, 5-enolypyruvyl shikimate 3-phosphate synthase (EPSPS) inhibitors, glutamine synthetase (GS) inhibitors, and synthetic auxins.

20. The method of claim 15, wherein said herbicide is glyphosate and said recombinant protein is a glyphosate-tolerant EPSPS.

21. A method of producing hybrid seed comprising:
a. applying an effective amount of herbicide to a transgenic plant comprising a recombinant DNA construct of claim 1, wherein said herbicide application is carried out during the development of the male reproductive tissue of said transgenic plant thereby inducing male-sterility in said transgenic plant;
b. fertilizing said transgenic plant with pollen from a second plant; and
c. harvesting hybrid seed from said transgenic plant.

22. The method of claim 21, wherein said transgenic plant is maize.

23. The method of claim 21, wherein said herbicide is glyphosate and said recombinant protein is a glyphosate-tolerant EPSPS.

24. The method of claim 23, wherein said glyphosate is applied during said development at an effective dose of about 0.125 pounds acid equivalent per acre to about 8 pounds acid equivalent per acre.

25. Hybrid seed harvested from a male-sterile transgenic plant that has been fertilized with pollen from a second plant, wherein said male-sterile transgenic plant comprises a recombinant DNA construct of claim 1 and has been induced to be male-sterile by application of an effective amount of herbicide during the development of the male reproductive tissue of said transgenic plant.

26. The recombinant DNA construct of claim 1, wherein said maize mts-siRNA element comprises a fragment of at least 18 contiguous nucleotides of the nucleotide sequence of SEQ ID NO:88.

27. The recombinant DNA construct of claim 1, wherein said maize mts-siRNA element comprises a fragment of at least 18 contiguous nucleotides of the nucleotide sequence of SEQ ID NO:89.

* * * * *